US008017648B2

(12) United States Patent
Castro et al.

(10) Patent No.: US 8,017,648 B2
(45) Date of Patent: Sep. 13, 2011

(54) METHODS OF USE OF CYCLOPAMINE ANALOGS

(75) Inventors: Alfredo C. Castro, Winchester, MA (US); Michael J. Grogan, Winchester, MA (US); Karen J. McGovern, Groton, MA (US); Martin Tremblay, Melrose, MA (US)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 788 days.

(21) Appl. No.: 11/965,675

(22) Filed: Dec. 27, 2007

(65) Prior Publication Data

US 2010/0286180 A1 Nov. 11, 2010

Related U.S. Application Data

(60) Provisional application No. 60/878,018, filed on Dec. 28, 2006, provisional application No. 60/941,596, filed on Jun. 1, 2007.

(51) Int. Cl.
*A61K 31/35* (2006.01)
*A61K 31/27* (2006.01)
*A61K 31/54* (2006.01)
*A61K 31/56* (2006.01)

(52) U.S. Cl. .......... 514/455; 514/47; 514/169; 514/222; 514/226; 514/261; 514/262; 514/278

(58) Field of Classification Search .................. 514/455, 514/47, 169, 222, 226.2, 261, 262, 2, 278
See application file for complete search history.

(56) References Cited

U.S. PATENT DOCUMENTS

| | | | |
|---|---|---|---|
| 6,238,876 B1 | 5/2001 | Altaba | |
| 6,291,516 B1 | 9/2001 | Dudek et al. | |
| 6,432,970 B2 | 8/2002 | Beachy et al. | |
| 6,867,216 B1 | 3/2005 | Beachy et al. | |
| 7,098,196 B1 | 8/2006 | Beachy et al. | |
| 7,230,004 B2 | 6/2007 | Adams et al. | |
| 7,291,626 B1 | 11/2007 | Beachy et al. | |
| 7,407,967 B2 | 8/2008 | Adams et al. | |
| 7,812,164 B2 | 10/2010 | Austad et al. | |
| 7,875,628 B2 | 1/2011 | Adams et al. | |
| 2003/0114393 A1 | 6/2003 | Liscovitch et al. | |
| 2003/0162870 A1 | 8/2003 | Kimura et al. | |
| 2004/0072913 A1 | 4/2004 | Tas et al. | |
| 2004/0072914 A1 | 4/2004 | Tas et al. | |
| 2004/0110663 A1 | 6/2004 | Dudek et al. | |
| 2004/0126359 A1 | 7/2004 | Lamb et al. | |
| 2004/0127474 A1 | 7/2004 | Dudek et al. | |
| 2006/0094660 A1 | 5/2006 | Thomson | |
| 2006/0128639 A1 | 6/2006 | Beachy | |
| 2006/0142245 A1 | 6/2006 | Beachy et al. | |
| 2007/0009530 A1 | 1/2007 | Altaba et al. | |
| 2007/0231828 A1 | 10/2007 | Beachy et al. | |
| 2007/0281040 A1 | 12/2007 | Weichselbaum et al. | |
| 2008/0019961 A1 | 1/2008 | Wicha et al. | |
| 2008/0057071 A1 | 3/2008 | Watkins et al. | |
| 2008/0058298 A1 | 3/2008 | Beachy et al. | |
| 2008/0095761 A1 | 4/2008 | Beachy et al. | |
| 2008/0118493 A1 | 5/2008 | Beachy et al. | |
| 2008/0269272 A1 | 10/2008 | Adams et al. | |
| 2008/0293754 A1 | 11/2008 | Austad et al. | |
| 2009/0012109 A1 | 1/2009 | Austad et al. | |
| 2009/0216022 A1 | 8/2009 | Austad et al. | |

FOREIGN PATENT DOCUMENTS

| | | |
|---|---|---|
| WO | WO-95/18856 | 7/1995 |
| WO | WO-96/17924 | 6/1996 |
| WO | WO-00/41545 | 7/2000 |
| WO | WO-01/27135 | 4/2001 |
| WO | WO-01/49279 | 7/2001 |
| WO | WO-02/30462 | 4/2002 |
| WO | WO-2005/013800 | 2/2005 |
| WO | WO-2005/032343 | 4/2005 |
| WO | WO-2005/042700 | 5/2005 |
| WO | WO-2006/026430 | 3/2006 |
| WO | WO-2007/123511 | 11/2007 |
| WO | WO-2008/083248 | 7/2008 |
| WO | WO-2008/083252 | 7/2008 |
| WO | WO-2008/089123 | 7/2008 |

OTHER PUBLICATIONS

International Search Report for PCT/US07/88990, mailed on Aug. 1, 2008, 2 pages.
Written Opinion of the International Searching Authority for PCT/US07/88990, mailed on Aug. 1, 2008, 8 pages.
International Search Report for PCT/US07/88995, mailed on Aug. 1, 2008, 2 pages.
Written Opinion of the International Searching Authority for PCT/US07/88995, mailed on Aug. 1, 2008, 6 pages.
Voituriez et al., Adv. Synth. Catal. (2006) 348:2363-2370.
Alexandre et al., Genes and Development (1996) 10:2003-2013. Bale and Yu, Human Molecular Genetics (2001) 10:757-762.
Belloni et al., Nature Genetics (1996) 14:353-356.
Berge et al, Journal of Pharmaceutical Sciences (1977) 66:1-19.
Berman et al., Nature (2003) 425:846-851.
Berman et al., Science (2002) 297:1559-1561.
Chen et al., Genes and Development (2002) 16:2743-2748.
Cooper et al., Science (1998) 280:1603-1607.
Fan et al., Endocrinology (2004) 145:3961-3970.
International Search Report for PCT/US05/30406, published as WO/2006/026430, mailed on Apr. 4, 2006, 2 pages.

(Continued)

*Primary Examiner* — Andrew D. Kosar
(74) *Attorney, Agent, or Firm* — Fish & Richardson P.C.

(57) ABSTRACT

The invention provides methods for treating various conditions using derivatives of cyclopamine having the following formula:

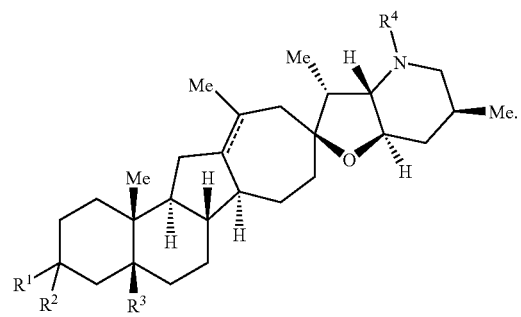

21 Claims, No Drawings

OTHER PUBLICATIONS

Karhadker et al., Nature (2004) 431:707-712.
Kitajima et al., Heterocycles (1981) 15:791-796.
Kubo et al., Cancer Research (2004) 64:6071-6074.
Lee et al., Journal of Agricultural and Food Chemistry (2003) 51(3):582-586.
Lewis and Veltmaat, Journal of Mammary Gland Biology and Neoplasia (2004) 2:165-181.
Ma et al., Carcinogenesis (2005) 10:1698-1705.
Nakamura et al., Biochemical and Biophysical Research Communications (1997) 237:465-469.
Patil et al., Cancer Biology & Therapy (2006) 5:111-117.
Peacock et al., PNAS USA (2007) 104:4048-4053.
Pietsch et al, Cancer Research (1997) 57:2085-2088.
Quirk et al., Cold Spring Harbor Symposium Quant. Biol. (1997) 62:217-226.
Rahman et al., Phytochemistry (1991) 1:368-370.
Reifenberger et al., Cancer Research (1998) 58:1798-1803.
Sheng et al., Molecular Cancer (2004) 3:29-42.
Sicklick et al, Carcinogenesis (2006) 27:748-757.
Supplementary Partial European Search Report for EP 05791140.6, mailed Nov. 26, 2007, 7 pages.
TAS and AVCI, Dermatology (2004) 209:126-131.
Thayer et al., Nature (2003) 425:851-856.
Van Der Horst et al., Bone (2003) 33:899-910.
Watkins et al., Nature (2003) 422:313-317.
Williams et al., PNAS USA (2003) 100:4616-4621.
Xie et al., Nature (1998) 391:90-92.
Aboulkassim, Tahar O. et al., "Alteration of the Patched locus in Superficial Bladder Cancer", Oncogene, vol. 22, (2003), pp. 2967-2971.
Bar, Elis E. et al., "Cyclopamine-Mediated Hedgehog Pathway Inhibition Depletes Stem-Like Cancer Cells in Gliobastoma", Stem Cells, vol. 25, (2007), pp. 2524-2533.
Bhattacharya, Resham et al., "Role of Hedgehog Signaling in Ovarian Cancer", Clin. Cancer Research, vol. 14, No. 23, (2008), pp. 7659-7666.
Clement, Virginie et al., "HEDGEHOD-GLI1 Signaling Regulates Human Glioma Growth, Cancer Stem Cell Self-Renewal and Tumorigenicity", Current Biology, vol. 17, (2007), pp. 1-8.
Cutcliffe, Colleen et al., Clear Cell Sarcoma of the Kidney: Up-regulation of Neural Markers with Activation of the Sonic Hedgehog and Akt Pathways, Human Cancer Biology, vol. 11, No. 22, (2005), pp. 7986-7994.
Dierks, Christine et al., "Essential Role of Stromally induced hedgehog signaling in B-cell malignancies", Nature Medicine, (2007), pp. 1-8.
Dierks, Christine et al., "Expansion of Bcr-Abl-Positive Leukemic Stem Cells is Dependent on Hedgehog Pathway Activation", Cancer Cell, vol. 14, (2008), pp. 238-249.
Dormeyer, Wilma et al., "Plasma Membrane Proteomics of Human Embryonic Stem Cells and Human Embryonal Carcinoma Cells", Journal of Proteome Research, vol. 7, (2008), pp. 2936-2951.
Ehtesham, M. et al., "Ligand dependent activation of the hedgehog pathway in glioma progenitor cells", Ongogene (2007), pp. 1-10.
Feldmann, Georg et al., "Blockade of Hedgehog Signaling Inhibits Pancreatic Cancer Invasion and Metastases: A New Paradigm for Combination Therapy in Solid Cancers", Cancer Research, vol. 67, No. 5, (2007), pp. 2187-2196.
Geng, Ling et al., "Hedgehod signaling in the murine melanoma microenvironment", Angiogenesis, vol. 10, (2007) pp. 259-267.
Hegde, Ganapati V. et al., Hedgehog-Induced Survival of B-Cell Chronic Lymphocytic Leukemia Cells in a Stromal Cell Microenvironment: A Potential New Therapeutic Target, Mol. Cancer Res., vol. 6, (2008), pp. 1928-1936.
Ji, Zhenyu et al., "PKA, Not EPAC, Suppresses Hedgehog Activity and Regulates Glucocorticoid Sensitivity in Acute Lymphoblastic Leukemia Cells", Journal of Biological Chemistry, (2007), pp. 1-19.
Lindemann, Ralph K., "Stroma-Initiated Hedgehog Signaling Takes Center Stage in B-Cell Lymphoma", Cancer Research, vol. 68, No. 4, (2008), pp. 961-964.
Ma, Xiao-Li et al., "Study of Sonic Hedgehod signaling pathway related molecules in gastric carcinoma", World Journal of Gastroenterology, vol. 12, No. 25, (2006), pp. 3965-3969.
Manna, Joseph D. et al, "Metabolite Identification of IPI-609, a Novel and Potent Inhibitor of the Hedgehog Pathway, in Different Species", (2008), 1 page.
Masamune, T. et al., "Syntheses and NMR Spectra of 22,27-IMINO-17,23-Oxidojervane Derivatives", Tetrahedron, vol. 23, (1967), pp. 1591-1612).
Ohta, Miki et al., p53-Independent Negative Regulation of p21/Cyclin-Dependent Kinase-Interacting Protein 1 by the Sonic Hedgehog-Glioma-Associated Oncogene 1 Pathway in Gastric Carcinoma Cells, Cancer Research, vol. 65, No. 23, (2005), pp. 10822-10829.
Pasca Di Magliano, Marina et al., "Hedgehog Signalling in Cancer Formation and Maintenance", Nature Reviews/Cancer, vol. 3, (2003), pp. 903-911.
Rubin, Lee L. et al., "Targeting the Hedgehog Pathway in Cancer", Nature Reviews/Drug Discovery, vol. 5, (2006), pp. 1026-1033.
Saldanha, Gerald, "The Hedgehog signalling pathway and cancer", Journal of Pathology, vol. 193, (2001), pp. 427-432.
Shiotani, A. et al., "Sonic hedgehog and CDX2 expression in the stomach", J. Gastroenterol. Hepatol., (2008), S161-S166, (publication abstract only enclosed—1 page).
Sims-Mourtada, Jennifer et al., "Hedgehog: an Attribute to Tumor Regrowth after Chemoradiotherapy and a Target to Improve Radiation Response", Clinical Cancer Research, vol. 12, No. 21, (2006), pp. 6565-6572.
Stecca, Barbara et al., "Melanomas require HEDGEHOG-GLI signaling regulated by interactions between GLI1 and the RAS-MEK/AKT pathways", Proceedings of the National Academy of Sciences of the United States of America (PNAS), vol. 104, No. 14, (2007), pp. 5895-5900.
Steg, Adam et al., "Multiple Gene Expression Analyses in Paraffin-Embedded Tissues by TaqMan Low-Density Array", J. Molecular Diagnostics, vol. 8, (2006), pp. 76-83.
Taipale, Jussi et al., "Effects of oncogenic mutations in Smoothened and Patched can be reversed by cyclopamine", Nature, vol. 406, (2000), pp. 1005-1009.
Thievessen, I. et al., J. Cell Physiol., "Hedgehog signaling in normal urothelial cells and urothelial carcinoma cell lines", vol. 203, No. 2, (2005), pp. 372-377, (publication abstract only enclosed—1 page).
Travaglione, Veronica et al., "A novel Hh pathway inhibitor, IPI-926, delays recurrence post-chemotherapy in a primary human SCLC xenograft model #4611", Apr. 2008,1 page.
Tremblay, Martin R., "Semisynthetic Cyclopamine Analogues as Potent and Orally Bioavailable Hedgehog Pathway Antagonists", Journal of Medicinal Chemistry, vol. 51, (2008), pp. 6646-6649.
Wunder, Jay S. et al., "Opportunities for improving the therapeutic ratio for patients with sarcoma", Lancet Oncology, vol. 8, (2007), pp. 513-524.
Yang, Hai-Su and Hinds, Philip W., "pRb-mediated control of epithelial cell proliferation and Indian Hedgehog expression in mouse intestinal development", BMC Developmental Biology, vol. 7, No. 6, (2007), pp. 1-12.
Yoshizaki, Ayumi et al., "Expressionsl of sonic hedgehog, patched, smoothened and Gli-1 in human intestinal stromal tumors and their correlation with prognosis", World Journal of Gastroenterology, vol. 12, No. 35, (2006), pp. 5687-5691.
Zhao, Chen et al., Hedgehog signalling is essential for maintenance of cancer stem cells in myeloid leukaemia, Nature Letters, (Jan. 2009), pp. 1-5.
Extended European Search Report including the supplementary European Search Report and European Search Opinion that was issued in connection with EP 07870001.0 (mail date of search report: Dec. 2, 2010), 11 pages.
Extended European Search Report including the supplementary European Search Report and European Search Opinion that was issued in connection with EP 07870006.9 (mail date of search report: Dec. 2, 2010), 7 pages.

METHODS OF USE OF CYCLOPAMINE ANALOGS

RELATED APPLICATIONS

This application claims priority to U.S. Ser. No. 60/878,018, filed 28 Dec. 2006, and U.S. Ser. No. 60/941,596, filed 1 Jun. 2007, both of which are hereby incorporated by reference in their entirety.

GOVERNMENT FUNDING

Some of the work described herein was done with government support under grant number K23 CA107040, awarded by the NIH/NCI. The government may have certain rights in the invention.

BACKGROUND OF THE INVENTION

The present invention generally relates to methods for antagonizing the hedgehog pathway and for treating various conditions using cyclopamine analogs.

Inhibition of the hedgehog pathway in certain cancers has been shown to result in inhibition of tumor growth. For example, anti-hedgehog antibodies have been shown to antagonize the function of the hedgehog pathway and inhibit the growth of tumors. Small molecule inhibition of hedgehog pathway activity has also been shown to result in cell death in a number of cancer types.

Research in this area has focused primarily on the elucidation of hedgehog pathway biology and the discovery of new hedgehog pathway inhibitors. Although inhibitors of the hedgehog pathway have been identified, there still exists the need to identify more potent inhibitors of the hedgehog pathway.

PCT publication WO 2006/026430 published 9 Mar. 2006 and assigned to the same assignee as the present application, discloses a wide variety of cyclopamine analogs, focusing on those with unsaturation in the A or B ring. In the present application, the surprisingly potent analogs contain completely saturated A and B rings.

SUMMARY OF THE INVENTION

The present invention relates to methods for treating hyperproliferative disorders and conditions mediated by the hedgehog pathway.

In one aspect, the invention relates to a method for treating a hyperproliferative disorder. The method includes administering to a subject an effective amount of a compound having the formula:

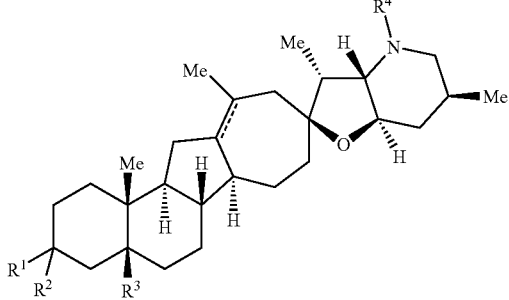

or a pharmaceutically acceptable salt thereof;

where $R^1$ is H, alkyl, —OR, amino, sulfonamido, sulfamido, —OC(O)$R^5$, —N($R^5$)C(O)$R^5$, or a sugar;

$R^2$ is H, alkyl, alkenyl, alkynyl, aryl, cycloalkyl, nitrile, or heterocycloalkyl;

or $R^1$ and $R^2$ taken together form =O, =S, =N(OR), =N(R), =N(NR$_2$), =C(R)$_2$;

$R^3$ is H, alkyl, alkenyl, or alkynyl;

$R^4$ is H, alkyl, alkenyl, alkynyl, aryl, cycloalkyl, heterocycloalkyl, aralkyl, heteroaryl, heteroaralkyl, haloalkyl, —OR$^5$, —C(O)R$^5$, —CO$_2$R$^5$, —SO$_2$R$^5$, —C(O)N(R$^5$)(R$^5$), —[C(R)$_2$]$_q$—R$^5$, —[(W)—N(R)C(O)]$_q$R$^5$, —[(W)—C(O)]$_q$R$^5$, —[(W)—C(O)O]$_q$R$^5$, —[(W)—OC(O)]$_q$R$^5$, —[(W)—SO$_2$]$_q$R$^5$, —[(W)—N(R$^5$)SO$_2$]$_q$R$^5$, —[(W)—C(O)N(R$^5$)]$_q$R$^5$, —[(W)—O]$_q$R$^5$, —[(W)—N(R)]$_q$R$^5$, —W—NR$^5_3$$^+$X$^-$ or —[(W)—S]$_q$R$^5$; where each W is independently for each occurrence a diradical;

each q is independently for each occurrence 1, 2, 3, 4, 5, or 6;

X$^-$ is a halide;

each R is independently H, alkyl, alkenyl, alkynyl, aryl, cycloalkyl or aralkyl;

each $R^5$ is independently for each occurrence H, alkyl, alkenyl, alkynyl, aryl, cycloalkyl, heterocycloalkyl, aralkyl, heteroaryl, heteroaralkyl or —[C(R)$_2$]$_p$—R$^6$;

wherein p is 0-6; or where any two occurrences of $R^5$ on the same substituent can be taken together to form a 4-8 membered optionally substituted ring which contains 0-3 heteroatoms selected from N, O, S, and P;

each $R^6$ is independently hydroxyl, —N(R)COR, —N(R)C(O)OR, —N(R)SO$_2$(R), —C(O)N(R)$_2$, —OC(O)N(R)(R), —SO$_2$N(R)(R), —N(R)(R), —COOR, —C(O)N(OH)(R), —OS(O)$_2$OR, —S(O)$_2$OR, —OP(O)(OR)(OR), —NP(O)(OR)(OR), or —P(O)(OR)(OR).

In some embodiments, when $R^2$, $R^3$, and $R^4$ are H; $R^1$ is not hydroxyl or a sugar.

In some embodiments, when $R^4$ is hydroxyl, then $R^1$ is not a sugar or hydroxyl, and $R^1$ and $R^2$ together are not C=O.

In some embodiments, $R^1$ is sulfonamido.

The condition can be selected from the group consisting of skin cancers, cancers of the central nervous system, cancers of the gastrointestinal tract, cancers of the pulmonary system, genitourinary cancers, breast cancer, hepatocellular cancer, brain cancers, and cancers of the hematopoietic system.

In another aspect, the invention relates to a method of treating a condition mediated by the hedgehog pathway. The method includes administering to a subject an effective amount of a compound having the formula:

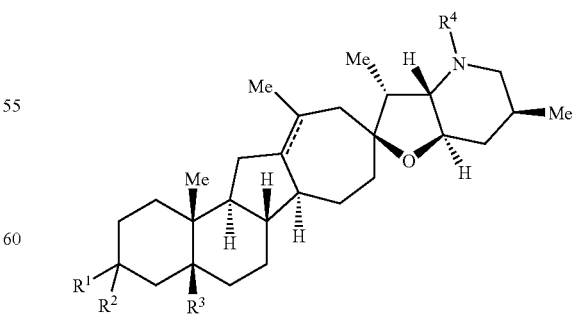

or a pharmaceutically acceptable salt thereof;
where $R^1$ is H, alkyl, —OR, amino, sulfonamido, sulfamido, —OC(O)R$^5$, —N(R$^5$)C(O)R$^5$, or a sugar;

$R^2$ is H, alkyl, alkenyl, alkynyl, aryl, cycloalkyl, nitrile, or heterocycloalkyl;

or $R^1$ and $R^2$ taken together form =O, =S, =N(OR), =N(R), =N(NR$_2$), =C(R)$_2$;

$R^3$ is H, alkyl, alkenyl, or alkynyl;

$R^4$ is H, alkyl, alkenyl, alkynyl, aryl, cycloalkyl, heterocycloalkyl, aralkyl, heteroaryl, heteroaralkyl, haloalkyl, —OR$^5$, —C(O)R$^5$, —CO$_2$R$^5$, —SO$_2$R$^5$, —C(O)N(R$^5$)(R$^5$), —[C(R)$_2$]$_q$—R$^5$, —[(W)—N(R)C(O)]$_q$R$^5$, —[(W)—C(O)]$_q$R$^5$, —[(W)—C(O)O]$_q$R$^5$, —[(W)—OC(O)]$_q$R$^5$, —[(W)—SO$_2$]$_q$R$^5$, —[(W)—N(R$^5$)SO$_2$]$_q$R$^5$, —[(W)—C(O)N(R$^5$)]$_q$R$^5$, —[(W)—O]$_q$R$^5$, —[(W)—N(R)]$_q$R$^5$, —W—NR$^5_3$$^+$X$^-$ or —[(W)—S]$_q$R$^5$;

where each W is independently for each occurrence a diradical; each q is independently for each occurrence 1, 2, 3, 4, 5, or 6;

X$^-$ is a halide;

each R is independently H, alkyl, alkenyl, alkynyl, aryl, cycloalkyl or aralkyl;

each $R^5$ is independently for each occurrence H, alkyl, alkenyl, alkynyl, aryl, cycloalkyl, heterocycloalkyl, aralkyl, heteroaryl, heteroaralkyl or —[C(R)$_2$]$_p$—R$^6$;

wherein p is 0-6; or where any two occurrences of $R^5$ on the same substituent can be taken together to form a 4-8 membered optionally substituted ring which contains 0-3 heteroatoms selected from N, O, S, and P;

each $R^6$ is independently hydroxyl, —N(R)COR, —N(R)C(O)OR, —N(R)SO$_2$(R), —C(O)N(R)$_2$, —OC(O)N(R)(R), —SO$_2$N(R)(R), —N(R)(R), —COOR, —C(O)N(OH)(R), —OS(O)$_2$OR, —S(O)$_2$OR, —OP(O)(OR)(OR), —NP(O)(OR)(OR), or —P(O)(OR)(OR).

In some embodiments, when $R^2$, $R^3$, and $R^4$ are H; $R^1$ is not hydroxyl or a sugar.

In some embodiments, when $R^4$ is hydroxyl, then $R^1$ is not a sugar or hydroxyl, and $R^1$ and $R^2$ together are not C=O.

In some embodiments, $R^1$ is sulfonamido.

The condition can be selected from the group consisting of skin cancers, cancers of the central nervous system, cancers of the gastrointestinal tract, cancers of the pulmonary system, genitourinary cancers, breast cancer, hepatocellular cancer, brain cancers, and cancers of the hematopoietic system. Specific examples include small cell lung cancer, pancreatic cancer, medulloblastoma, multiple myeloma, leukemia, myelodysplastic syndrome, non-Hodgkin's lymphoma, and Hodgkin's disease. The compound may be administered orally, intravenously, or topically.

In another aspect, the invention relates to a method of antagonizing the hedgehog pathway in a subject. The method includes administering to the subject an effective amount of a compound having the formula:

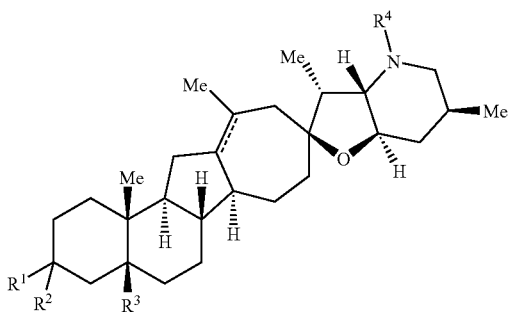

or a pharmaceutically acceptable salt thereof;

wherein $R^1$ is H, alkyl, —OR, amino, sulfonamido, sulfamido, —OC(O)R$^5$, —N(R$^5$)C(O)R$^5$, or a sugar;

$R^2$ is H, alkyl, alkenyl, alkynyl, aryl, cycloalkyl, nitrile, or heterocycloalkyl;

or $R^1$ and $R^2$ taken together form =O, =S, =N(OR), =N(R), =N(NR$_2$), =C(R)$_2$;

$R^3$ is H, alkyl, alkenyl, or alkynyl;

$R^4$ is H, alkyl, alkenyl, alkynyl, aryl, cycloalkyl, heterocycloalkyl, aralkyl, heteroaryl, heteroaralkyl, haloalkyl, —OR$^5$, —C(O)R$^5$, —CO$_2$R$^5$, —SO$_2$R$^5$, —C(O)N(R$^5$)(R$^5$), —[C(R)$_2$]$_q$—R$^5$, —[(W)—N(R)C(O)]$_q$R$^5$, —[(W)—C(O)]$_q$R$^5$, —[(W)—C(O)O]$_q$R$^5$, —[(W)—OC(O)]$_q$R$^5$, —[(W)—SO$_2$]$_q$R$^5$, —[(W)—N(R$^5$)SO$_2$]$_q$R$^5$, —[(W)—C(O)N(R$^5$)]$_q$R$^5$, —[(W)—O]$_q$R$^5$, —[(W)—N(R)]$_q$R$^5$, —W—NR$^5_3$$^+$X$^-$ or —[(W)—S]$_q$R$^5$; wherein each W is independently for each occurrence a diradical; each q is independently for each occurrence 1, 2, 3, 4, 5, or 6;

X$^-$ is a halide;

each R is independently H, alkyl, alkenyl, alkynyl, aryl, cycloalkyl or aralkyl;

each $R^5$ is independently for each occurrence H, alkyl, alkenyl, alkynyl, aryl, cycloalkyl, heterocycloalkyl, aralkyl, heteroaryl, heteroaralkyl or —[C(R)$_2$]$_p$—R$^6$;

wherein p is 0-6; or where any two occurrences of $R^5$ on the same substituent can be taken together to form a 4-8 membered optionally substituted ring which contains 0-3 heteroatoms selected from N, O, S, and P;

each $R^6$ is independently hydroxyl, —N(R)COR, —N(R)C(O)OR, —N(R)SO$_2$(R), —C(O)N(R)$_2$, —OC(O)N(R)(R), —SO$_2$N(R)(R), —N(R)(R), —COOR, —C(O)N(OH)(R), —OS(O)$_2$OR, —S(O)$_2$OR, —OP(O)(OR)(OR), —NP(O)(OR)(OR), or —P(O)(OR)(OR).

In some embodiments, when $R^2$, $R^3$, and $R^4$ are H; $R^1$ is not hydroxyl or a sugar.

In some embodiments, when $R^4$ is hydroxyl, then $R^1$ is not a sugar or hydroxyl, and $R^1$ and $R^2$ together are not C=O.

In the embodiments described above, the compound may be selected from the group consisting of:

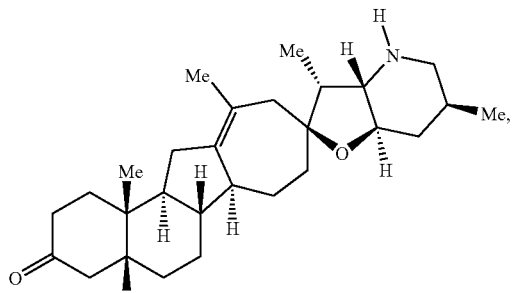

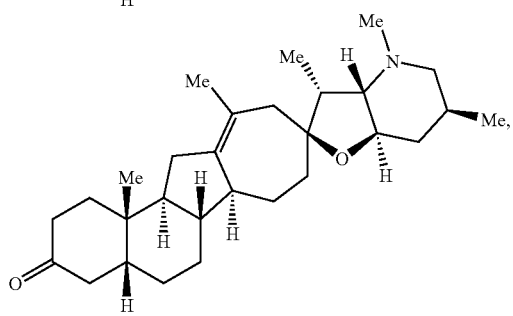

-continued
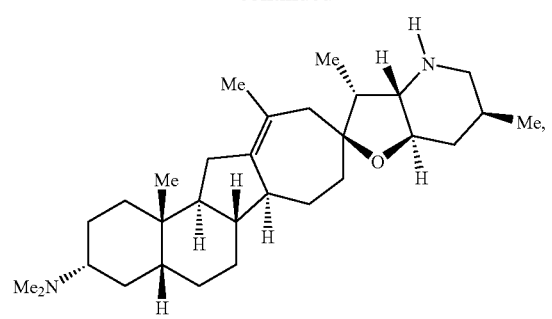
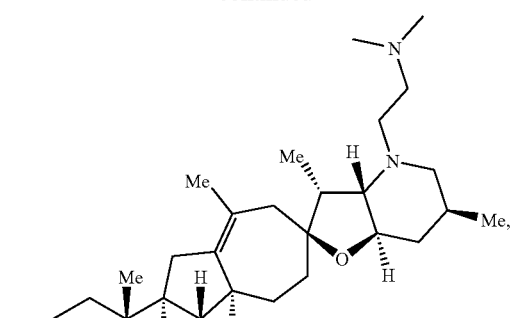
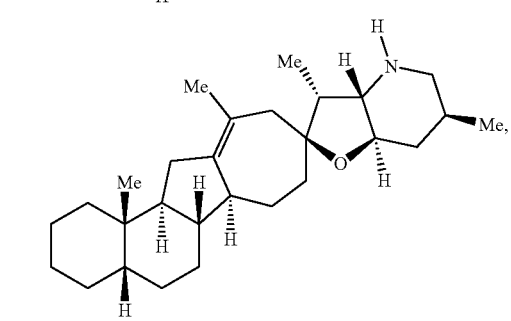
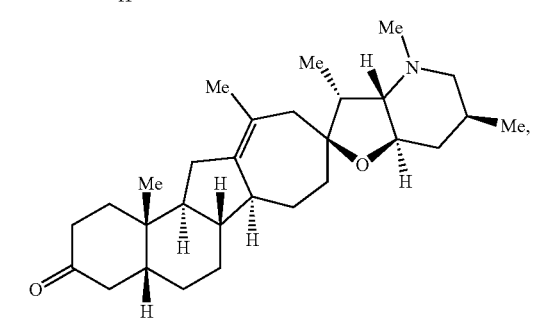
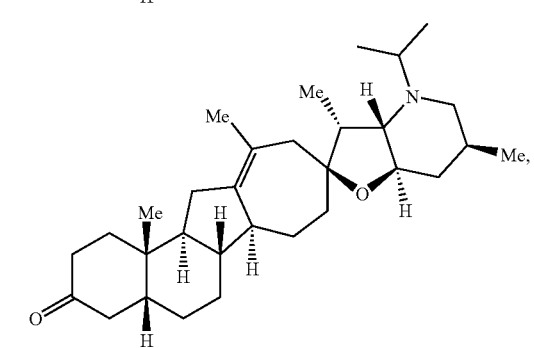
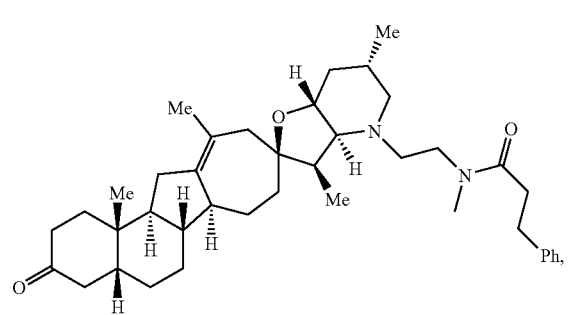
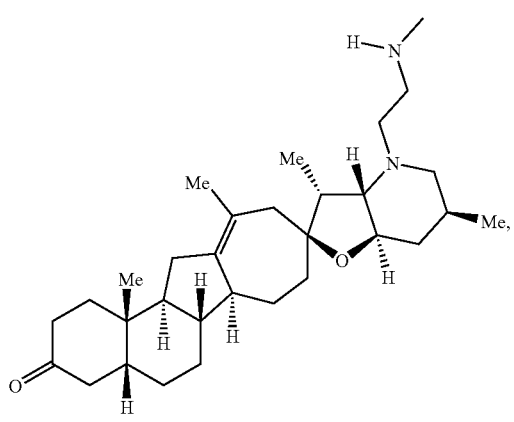

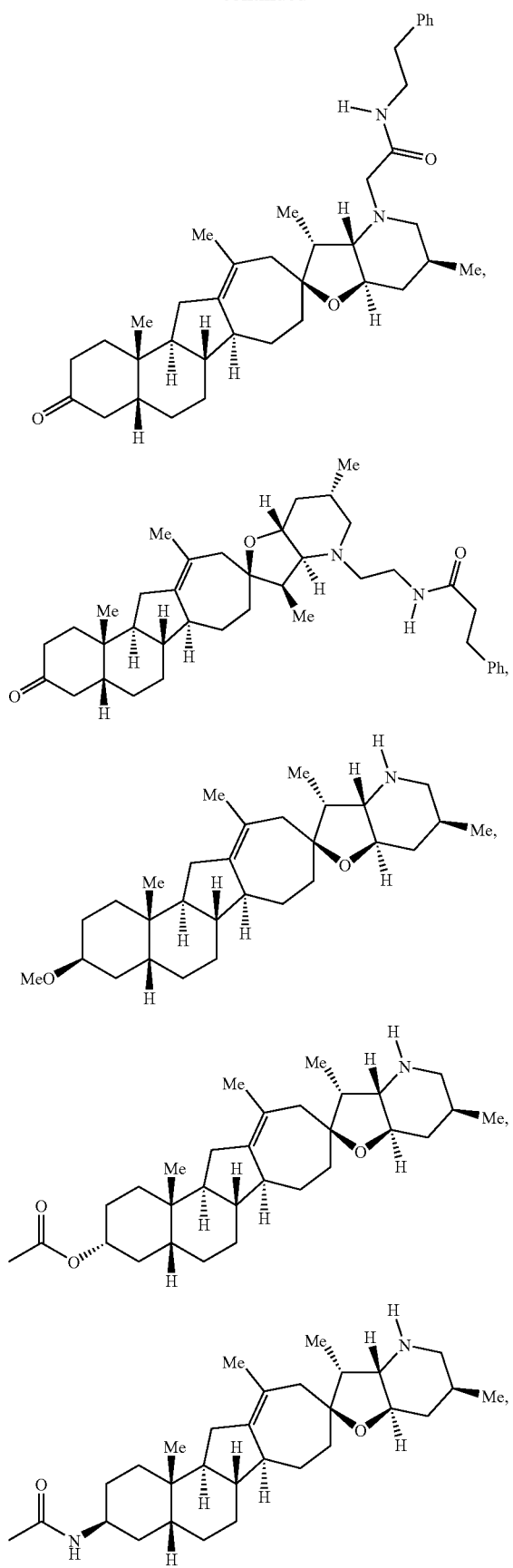
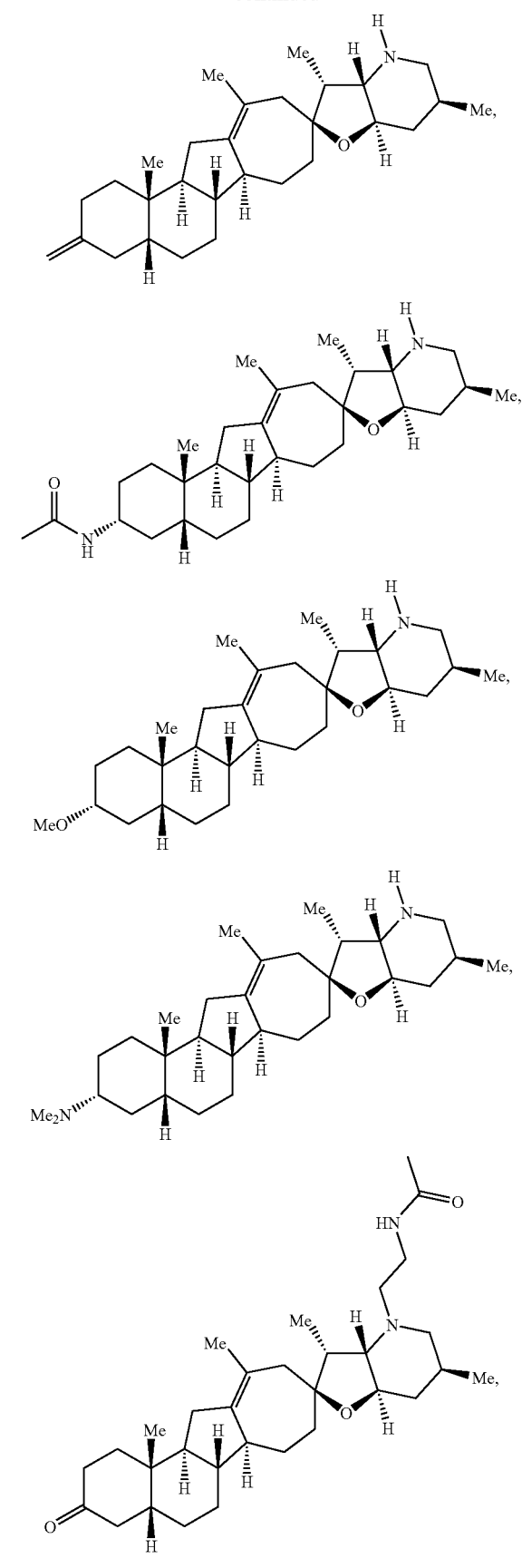

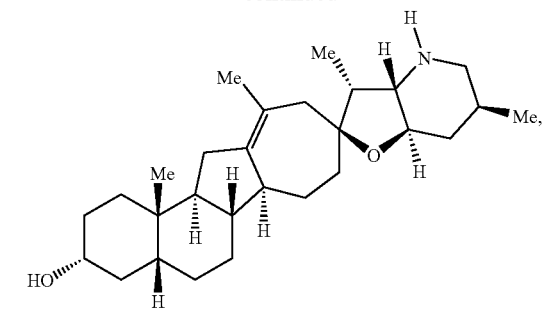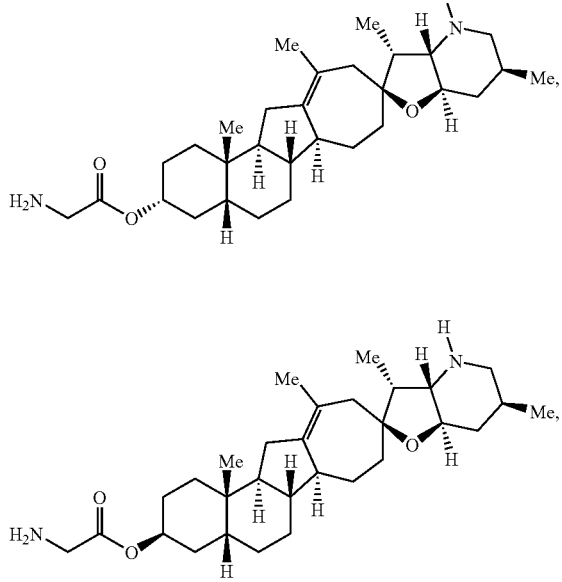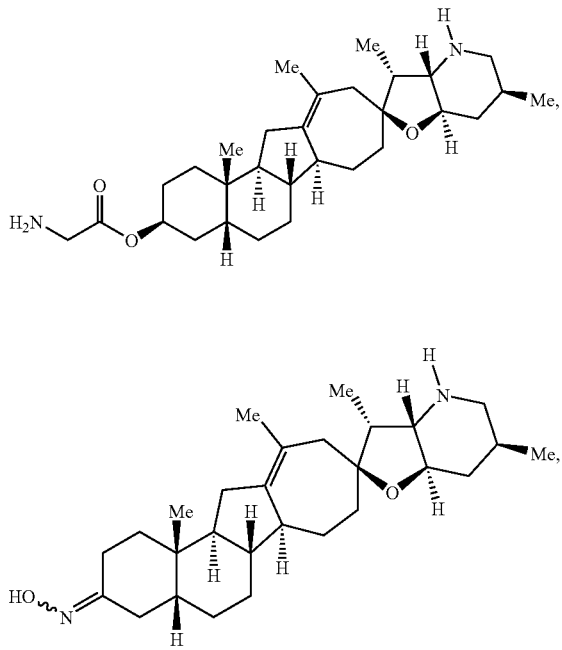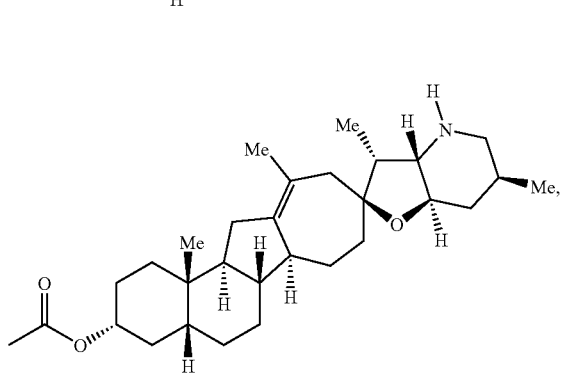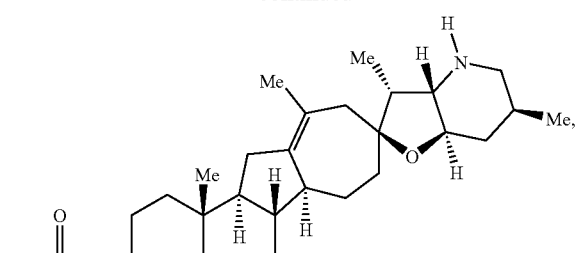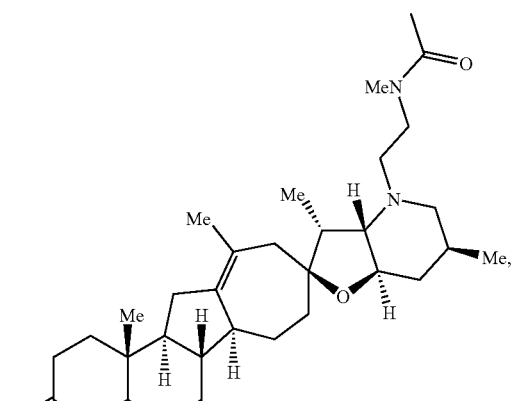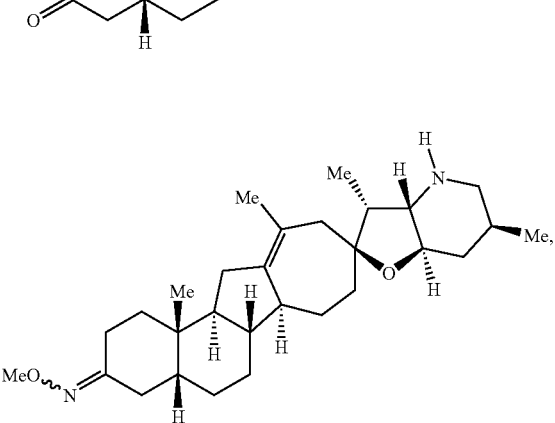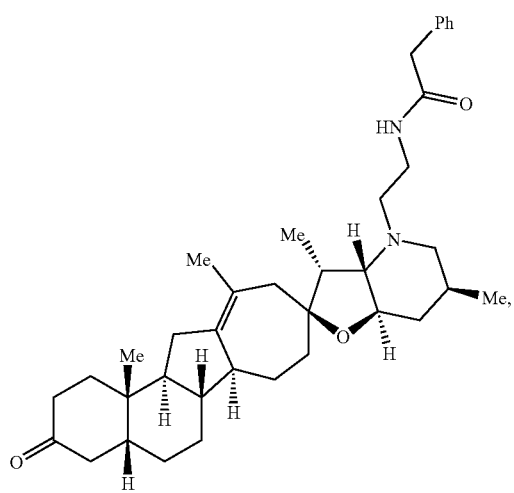

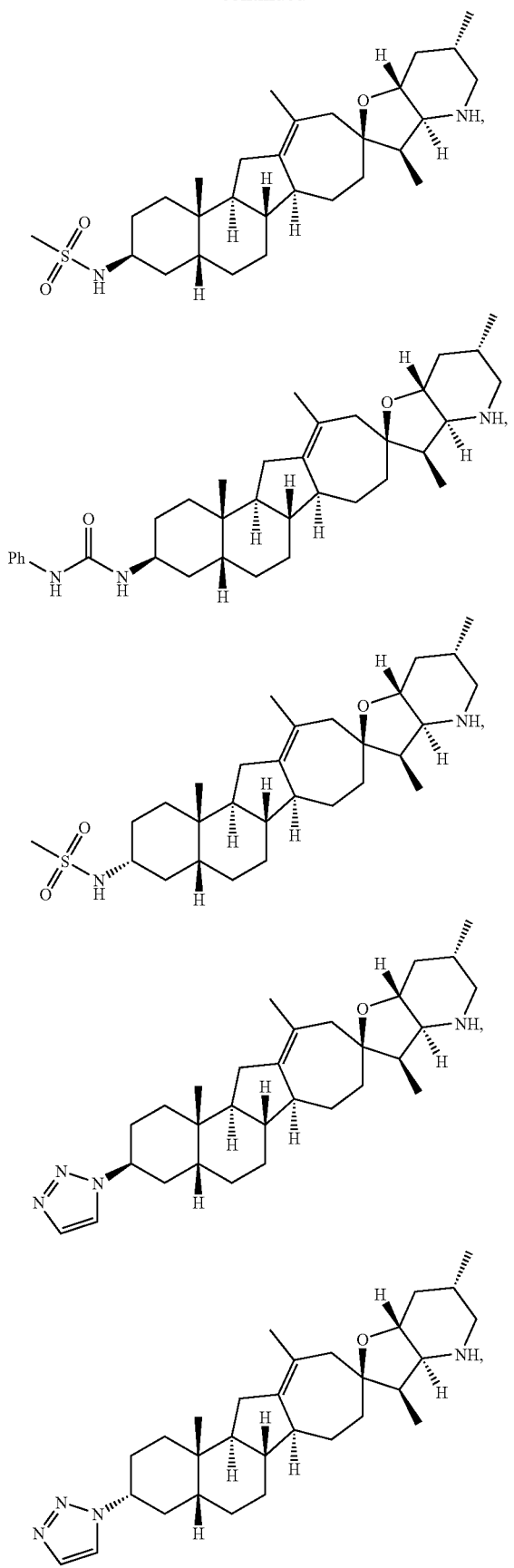
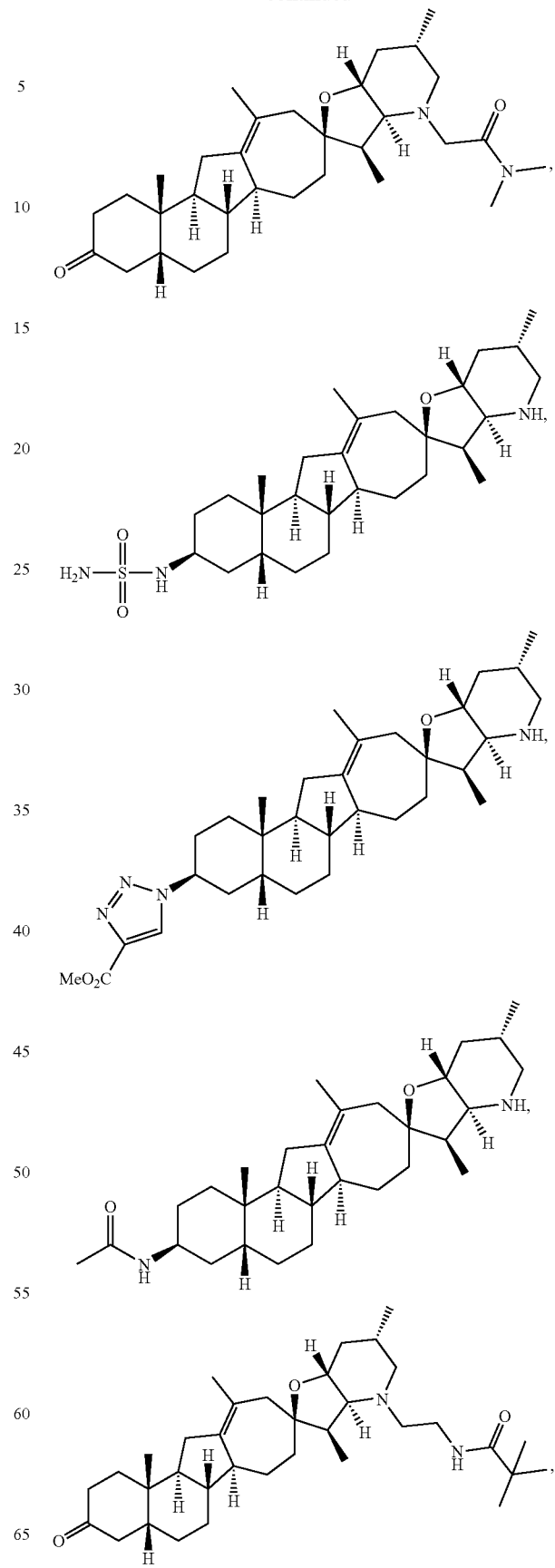

-continued

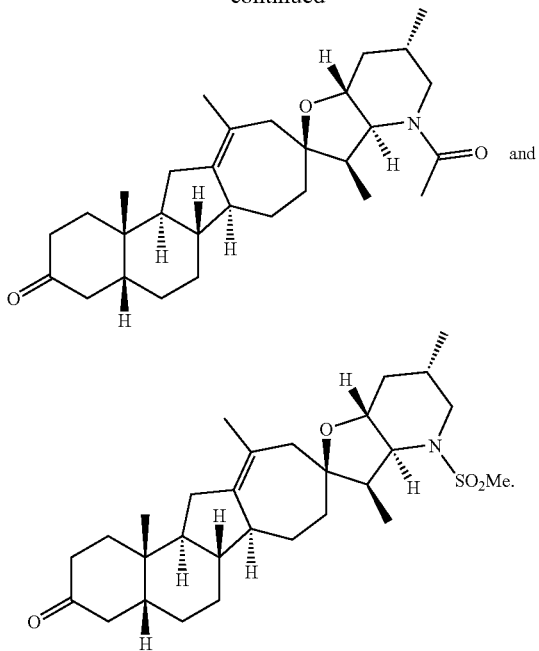

or a pharmaceutically acceptable salt thereof.

In another aspect, the invention relates to a method of antagonizing the hedgehog pathway in a subject. The method includes administering to the subject an effective amount of a compound having following structure:

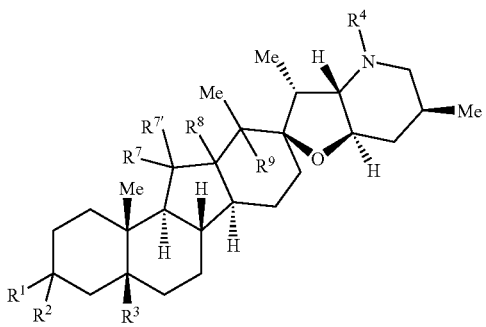

or a pharmaceutically acceptable salt thereof;

wherein $R^1$ is H, alkyl, —OR, amino, sulfonamido, sulfamido, —OC(O)$R^5$, —N($R^5$)C(O)$R^5$, or a sugar;

$R^2$ is H, alkyl, alkenyl, alkynyl, aryl, cycloalkyl, nitrile, or heterocycloalkyl;

or $R^1$ and $R^2$ taken together form =O, =S, =N(OR), =N(R)—, =N(NR$_2$), =C(R)$_2$;

$R^3$ is H, alkyl, alkenyl, or alkynyl; $R^4$ is H, alkyl, alkenyl, alkynyl, aryl, cycloalkyl, heterocycloalkyl, aralkyl, heteroaryl, heteroaralkyl, haloalkyl, —O$R^5$, —C(O)$R^5$, —CO$_2R^5$, —SO$_2R^5$, C(O)N($R^5$)($R^5$), —[C(R)$_2$]$_q$—$R^5$, —[(W)—N(R)C(O)]$_q R^5$, —[(W)—C(O)]$_q R^5$, —[(W)—C(O)O]$_q R^5$, [(W)—(W)—OC(O)]$_q R^5$, —[(W)—SO$_2$]$_q R^5$, —[(W)—N($R^5$)SO$_2$]$_q R^5$, —[(W)—C(O)N($R^5$)]$_q R^5$, —[(W)—O]$_q R^5$, —[(W)—N(R)]$_q R^5$, —W—N$R^5_3{}^+$X$^-$, or —[(W)—S]$_q R^5$;

wherein each W is, independently, a diradical;
each q is, independently, 1, 2, 3, 4, 5, or 6;
X$^-$ is a halide;

each R is independently H, alkyl, alkenyl, alkynyl, aryl, cycloalkyl or aralkyl;

each $R^5$ is, independently, H, alkyl, alkenyl, alkynyl, aryl, cycloalkyl, heterocycloalkyl, aralkyl, heteroaryl, heteroaralkyl or —[C(R)$_2$]$_p$—$R^6$;

wherein p is 0-6; or any two occurrences of $R^5$ on the same substituent can be taken together to form a 4-8 membered optionally substituted ring which contains 0-3 heteroatoms selected from N, O, S, and P;

each $R^6$ is, independently, hydroxyl, —N(R)COR, —N(R)C(O)OR, —N(R)SO$_2$(R), —C(O)N(R)$_2$, —OC(O)N(R)(R), —SO$_2$N(R)(R), —N(R)(R), —COOR, —C(O)N(OH)(R), —OS(O)$_2$OR, —S(O)$_2$OR, —OP(O)(OR)(OR), —NP(O)(OR)(OR), or —P(O)(OR)(OR) where each R is independently H, alkyl, alkenyl, alkynyl, aryl, cycloalkyl or aralkyl;

each of $R^7$ and $R^{7'}$ is H; or
$R^7$ and $R^{7'}$ taken together form =O;
each $R^8$ and $R^9$ is H or $R^8$ and $R^9$ taken together form a bond; and provided that when $R^3$, $R^4$, $R^8$, $R^9$ are H and, $R^7$ and $R^{7'}$ taken together form =O; $R^1$ can not be hydroxyl and $R^2$ can not be H;

provided that when $R^3$, $R^4$, $R^8$, $R^9$ are H and, $R^7$ and $R^{7'}$ taken together form =O; $R^1$ can not be acetate and $R^2$ can not be H;

provided that when $R^3$, $R^4$, $R^8$, $R^9$ are H and, $R^7$ and $R^8$ are H; $R^1$ and $R^2$ taken together can not be =O; and provided that when $R^3$, $R^4$, $R^8$, $R^9$ are H and, $R^7$ and $R^{7'}$ are H; $R^1$ and $R^2$ can not be H.

In some embodiments, $R^1$ is sulfonamido.

DETAILED DESCRIPTION OF THE INVENTION

Definitions

The definitions of terms used herein are meant to incorporate the present state-of-the-art definitions recognized for each term in the chemical and pharmaceutical fields. Where appropriate, exemplification is provided. The definitions apply to the terms as they are used throughout this specification, unless otherwise limited in specific instances, either individually or as part of a larger group.

As used herein, the definition of each expression, e.g., alkyl, m, n, etc., when it occurs more than once in any structure, is intended to be independent of its definition elsewhere in the same structure.

The term "acylamino" refers to a moiety that may be represented by the general formula:

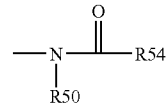

wherein R50 and R54 represent a hydrogen, an alkyl, an alkenyl or —(CH$_2$)$_m$—R61, where R61 represents an aryl, a cycloalkyl, a cycloalkenyl, a heterocycle or a polycycle; and m is zero or an integer in the range of 1 to 8.

The terms "alkenyl" and "alkynyl" refer to unsaturated aliphatic groups analogous in length and possible substitution to the alkyls described above, but that contain at least one double or triple bond respectively.

The terms "alkoxyl" or "alkoxy" refers to an alkyl group, as defined above, having an oxygen radical attached thereto.

Representative alkoxyl groups include methoxy, ethoxy, propyloxy, tert-butoxy and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has 30 or fewer carbon atoms in its backbone (e.g., $C_1$-$C_{30}$ for straight chain, $C_3$-$C_{30}$ for branched chain), 20 or fewer. Likewise, certain cycloalkyls have from 3-10 carbon atoms in their ring structure, and others have 5, 6 or 7 carbons in the ring structure.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—$(CH_2)_m$—R61, wherein m and R61 are defined above. Representative alkylthio groups include methylthio, ethyl thio, and the like.

The term "amido" is art recognized as an amino-substituted carbonyl and includes a moiety that may be represented by the general formula:

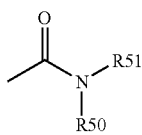

wherein R50 and R51 each independently represent a hydrogen, an alkyl, an alkenyl, —$(CH_2)_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. Certain embodiments of the amide in the present invention will not include imides which may be unstable.

The terms "amine" and "amino" are art-recognized and refer to both unsubstituted and substituted amines, e.g., a moiety that may be represented by the general formulas:

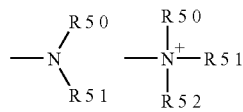

wherein R50, R51 and R52 each independently represent a hydrogen, an alkyl, an alkenyl, —$(CH_2)_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. Thus, the term "alkylamine" includes an amine group, as defined above, having a substituted or unsubstituted alkyl attached thereto, i.e., at least one of R50 and R51 is an alkyl group.

The term "aralkyl", as used herein, refers to an alkyl group substituted with an aryl group (e.g., an aromatic or heteroaromatic group).

The term "aryl" as used herein includes 5-, 6- and 7-membered single-ring aromatic groups that may include from zero to four heteroatoms, for example, benzene, anthracene, naphthalene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The term "Brønsted acid" refers to any substance that can act as a hydrogen ion (proton) donor.

The term "carboxyl" is includes such moieties as may be represented by the general formulas:

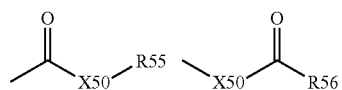

wherein X50 is a bond or represents an oxygen or a sulfur, and each of R55 and R56 represents independently a hydrogen, an alkyl, an alkenyl, —$(CH_2)_m$—R61 or a pharmaceutically acceptable salt, where m and R61 are defined above.

The term "diradical" refers to any of a series of divalent groups from alkyl, alkenyl, alkynyl, aryl, cycloalkyl, heterocycloalkyl, aralkyl, heteroaryl, and heteroaralkyl groups. For example,

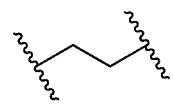

is an alkyl diradical;

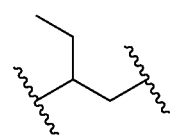

is also an alkyl diradical;

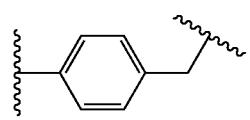

is an aralkyl diradical; and

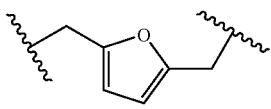

is an (alkyl)heteroaralkyl diradical. Typical examples include alkylenes of general structure $(CH_2)_x$ where X is 1-6, and corresponding alkenylene and alkynylene linkers having 2-6 carbon atoms and one or more double or triple bonds; cycloalkylene groups having 3-8 ring members; and aralkyl groups wherein one open valence is on the aryl ring and one is on the alkyl portion such as

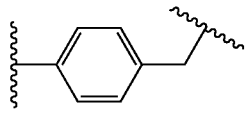

and its isomers.

An "effective amount" refers to an amount of compound which, when administered as part of a desired dosage regimen brings about a desired effect, e.g., a change in the rate of cell proliferation and/or rate of survival of a cell according to clinically acceptable standards for the disorder to be treated.

The term "haloalkyl", as used herein, refers to an alkyl group where anywhere from 1 to all hydrogens have been replaced with a halide. A "perhaloalkyl" is where all of the hydrogens have been replaced with a halide.

The term "heteroatom" as used herein means an atom of any element other than carbon or hydrogen. Examples of heteroatoms include boron, nitrogen, oxygen, phosphorus, sulfur and selenium.

The terms "heterocyclyl" or "heterocyclic group" refer to 3- to 10-membered ring structures, in some instances from 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, $-CF_3$, $-CN$, or the like.

The term "isolated" in connection with a compound of the present invention means the compound is not in a cell or organism and the compound is separated from some or all of the components that typically accompany it in nature.

The term "Lewis acid" refers to any substance that can act as an electron pair acceptor.

Unless the number of carbons is otherwise specified, "lower alkyl" as used herein means an alkyl group, as defined above, but having from one to ten carbons, in some embodiments from one to six carbon atoms in its backbone structure. Likewise, "lower alkenyl" and "lower alkynyl" have similar chain lengths. Certain alkyl groups are lower alkyls. In some embodiments, a substituent designated herein as alkyl is a lower alkyl.

As used herein, the term "nitro" means $-NO_2$; the term "halogen" designates $-F$, $-Cl$, $-Br$ or $-I$; the term "sulfhydryl" means $-SH$; the term "hydroxyl" means $-OH$; and the term "sulfonyl" means $-SO_2-$.

The term "oxo" refers to a carbonyl oxygen ($=O$).

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, $-CF_3$, $-CN$, or the like.

The term "epimerically pure" in connection with a compound of the present invention means that the compound is substantially free of stereoisomers of the compound wherein the configuration of the stereogenic center that $R^3$ is bonded to is inverted. For example an epimerically pure compound represented by the following formula:

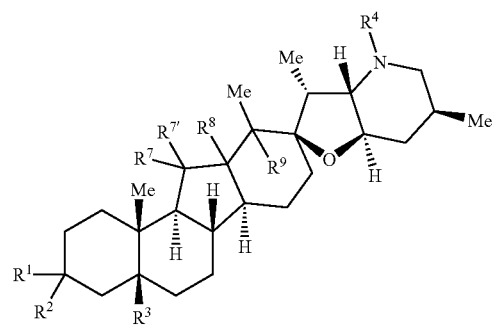

wherein $R^1$, $R^2$, $R^3$, $R^4$, $R^7$, $R^{7'}$, $R^8$, and $R^9$ are as defined below, is substantially free of compounds represented by the following formula:

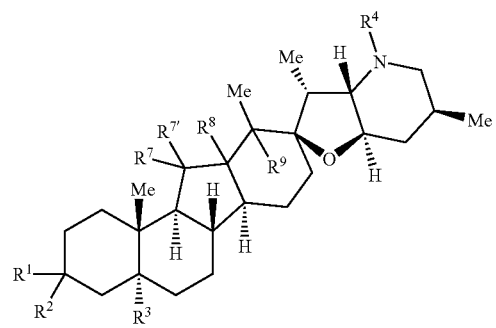

wherein $R^1$, $R^2$, $R^3$, $R^4$, $R^7$, $R^{7'}$, $R^8$, and $R^9$ are as defined below. Epimerically pure compounds contain less than about 20% by mass, less than about 15% by mass, less than about 10% by mass, less than about 5% by mass, or less than about 3% by mass of stereoisomeric compounds wherein the configuration of the stereogenic center that $R^3$ is bonded to is inverted relative to the compound.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M., *Protective Groups in Organic Synthesis*, $2^{nd}$ ed.; Wiley: New York, 1991). In some cases, the functional group being protected and the protecting group are together referred to as one moiety. For example, the fragment shown below is sometimes referred to as a benzyl carbonate; i.e., the protected (underlined) O makes up part of the carbonate.

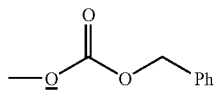

Similarly, the fragment shown below, in which the protected N makes up part of the carbamate, is referred to as a benzyl carbamate.

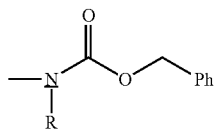

The term "sugar" as used herein refers to a natural or an unnatural monosaccharide, disaccharide or oligosaccharide comprising one or more pyranose or furanose rings. The sugar may be covalently bonded to the steroidal alkaloid of the present invention through an ether linkage or through an alkyl linkage. In certain embodiments the saccharide moiety may be covalently bonded to a steroidal alkaloid of the present invention at an anomeric center of a saccharide ring. Sugars may include, but are not limited to ribose, arabinose, xylose, lyxose, allose, altrose, glucose, mannose, gulose, idose, galactose, talose, glucose, and trehalose.

The term "sulfonamido" or "sulfonamide" as used herein includes a moiety having either of the following formulae:

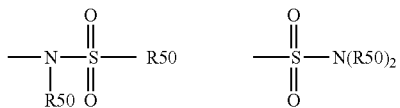

wherein $R^{50}$ is defined above.

The terms "triflyl", "tosyl", "mesyl", and "nonaflyl" refer to trifluoromethanesulfonyl, p-toluenesulfonyl, methanesulfonyl, and nonafluorobutanesulfonyl groups, respectively. The terms "triflate", "tosylate", "mesylate", and "nonaflate" to trifluoromethanesulfonate ester, p-toluenesulfonate ester, methanesulfonate ester, and nonafluorobutanesulfonate ester functional groups and molecules that contain the groups, respectively.

The term "thioxo" refers to a carbonyl sulfur (=S).

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge, et al. "Pharmaceutical Salts", *J. Pharm. Sci.* (1977) 66:1-19)

The pharmaceutically acceptable salts of the compounds of the present invention include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge, et al., supra)

Synthesis of Steroidal Alkaloid Compounds

The ring expanded steroidal alkaloid derivatives described above can be prepared directly from naturally occurring steroidal alkaloids or synthetic analogs thereof. In certain instances, the steroidal alkaloid starting materials can be cyclopamine or jervine. These steroidal alkaloids can be purchased commercially or extracted from *Veratrum Californicum*. Briefly, the process of the present invention comprises the steps of cyclopropanating suitable starting steroidal alkaloid derivatives followed by ring expansion rearrangement of the cyclopropyl derivatives. In some instances, it may be desirable to suitably protect or otherwise transform reactive functionalities present on the molecule prior to cyclopropanation. For example, an alcohol present at $R^1$ and a secondary nitrogen present on the fused furano-piperidine ring can both be protected prior to cyclopropanation. In certain embodiments, protecting groups that are efficiently added and removed from the alkaloid, yield intermediates in the synthetic process with improved handling properties and which allow for the efficient purification of the synthetic intermediates formed may be preferred.

Examples of oxygen protecting groups include, but are not limited to formate, acetate, chloroacetate, dichloroacetate, trichloroacetate, pivaloate, benzoates, alkyl carbonate, alkenyl carbonate, aryl carbonates, aralkyl carbonate (e.g., benzyl carbonate), 2,2,2-trichloroethyl carbonate, alkoxymethyl ether, aralkoxymethyl ether, alkylthiomethyl ether, aralkylthio ether, arylthio ether, trialkylsilyl ether, alkylarylsilyl ether, benzyl ether, arylmethyl ether, and allyl ether.

Examples of nitrogen protecting groups include, but are not limited to formyl, chloroacetyl, trichloroacetyl, trifluoroacetyl, phenyl acetyl, benzoyls, benzamides, alkyl carbamates, aralkyl carbamates (e.g., benzyl carbamates), aryl carbamates, allyl, aralkyl, alkoxymethyl, aralkoxymethyl, N-2-cyanoethyl, diarylphosphinamides, dialkylphosphinamidates, diarylphosphinamidates, and trialkylsilyl.

Additional protecting groups that may be used in the methods of the present invention are described in Green, T. W.; Wuts, P. G., *Protective Groups in Organic Synthesis*, $3^{rd}$ Edition, John Wiley & Sons, Inc. 1999.

A variety of cyclopropanating agents can be used to cyclopropanate the steroidal alkaloid. 1,1-haloalkylmetal complexes and reactive species referred to as carbenoids, are commonly used to cyclopropanate olefins. These reagents are typically made using a diiodoalkane or diazoalkane and a metal or organometalic species such as $Et_2Zn$, $iBu_3Al$, samarium, copper, rhodium, or palladium. In certain embodiments, $Et_2Zn$ and diiodomethane are used to generate the 1,1-haloalkylmetal species.

The reactivity and the ease of handling of the 1,1-haloalkylzinc complexes can be modified by the addition of certain reagents, such as acids. It is believed that the addition of an acid to the 1,1-haloalkylzinc species generates an alkyl zinc mixed salt. In the examples described below a biarylphosphoric acid is combined with diiodomethane and diethylzinc to generate a putative haloalkyl zinc phosphate cyclopropanating agent. A variety of phosphoric acids can be used to generate the putative haloalkylzinc phosphate.

Other known cyclopropanation methods such as those utilizing sulfur ylides to react with an olefin conjugated to a carbonyl to add a $CH_2$ or CH-alkyl or CH-aryl group, and metal-catalyzed decomposition of diazoalkyl and α-diazocarbonyl compounds, such as diazomethane and ethyl diazoacetate, can also be used: these methods readily provide cyclopropanes having alkyl, aryl, alkoxycarbonyl (—COOR), or acyl substituents. Additional cyclopropanating agents are described in Masalov, et al., *Organic Letters* (2004) 6:2365-2368 and Hansen, et al., *Chem. Comm.* (2006) 4838-4840.

The cyclopropyl ring may be substituted or unsubstituted. In cases where the cyclopropyl ring is substituted, the groups attached to the methylene of the cyclopropane will be installed onto the D ring after rearrangement and ring expansion.

The cyclopropanation reactions may be conducted in an aprotic solvent. Suitable solvents include ethers, such as diethyl ether, 1,2-dimethoxyethane, diglyme, t-butyl methyl ether, tetrahydrofuran and the like; halogenated solvents, such as chloroform, dichloromethane, dichloroethane, and the like; aliphatic or aromatic hydrocarbon solvents, such as benzene, xylene, toluene, hexane, pentane and the like; esters and ketones, such as ethyl acetate, acetone, and 2-butanone; polar aprotic solvents, such as acetonitrile, dimethylsulfoxide, dimethylformamide, and the like; or combinations of two or more solvents. In a certain embodiments, dichloromethane is the solvent used for the cyclopropanation when a dialkyl zinc and diiodomethane is used.

In the examples described below, a solution containing the cyclopropanating agent is prepared by first adding a solution of a phosphoric acid to a solution of diethylzinc, followed by addition of diiodomethane to the reaction solution. The cyclopropanation substrate is then added to this solution. Alternatively, the cyclopropanation agent can be prepared in the presence of the cyclopropanation substrate by changing the order of addition of the reagents. In certain embodiments, the cyclopropanation reaction is conducted by first adding the phosphoric acid to a solution of dialkylzinc, followed by the addition of the cyclopropanation substrate, and finally the dihaloalkane is added. Using this method the cyclopropanating agent is generated under controlled conditions and immediately reacts with the cyclopropanation substrate.

Following synthesis of the cyclopropanated steroidal alkaloid core, the compound may be derivatized using a variety of functionalization reactions known in the art. Representative examples include palladium coupling reactions to alkenylhalides or aryl halides, oxidations, reductions, reactions with nucleophiles, reactions with electrophiles, pericyclic reactions, radical reactions, installation of protecting groups, removal of protecting groups, and the like.

In the presence of Lewis or Brønsted acids the cyclopropyl analogs undergo a rearrangement and ring expansion to afford steroidal alkaloid analogs in which the D ring has been expanded by one carbon.

The cyclopropanation and ring expansion can take place in a two-step one reaction vessel process or in a two-step two reaction vessel process. When the cyclopropanation and ring expansion are conducted in the same reaction vessel the acid used to initiate the ring expansion rearrangement is added after completion of the cyclopropanation reaction. Under certain conditions, the zinc salts that are generated in the course of cyclopropanating the steroidal alkaloid can themselves act as Lewis acids to catalyze the ring expansion rearrangement. The reactivity of the zinc salts generated after the cyclopropanation can be modified by the addition of acids to generate more active Lewis acids.

As described below in the examples section, the methanesulfonic acid is added to the cyclopropanation reaction vessel after completion of the cyclopropanation. Additional examples of suitable acids include, but are not limited to zinc salts, boron compounds, magnesium salts, titanium salts, indium salts, aluminum salts, tin salts, lanthanum salts, trifluoromethanesulfonic acid, diaryloxyphosphoric acids, acetic acid, and HCl. In a certain embodiments of the invention the Lewis acid used is a zinc salt or $BF_3$.

These ring expanded analogs may be further functionalized using a variety of functionalization reactions known in the art. Representative examples include palladium coupling reactions to alkenylhalides or aryl halides, oxidations, reductions, reactions with nucleophiles, reactions with electrophiles, pericyclic reactions, radical reactions, installation of protecting groups, removal of protecting groups, and the like.

Pharmaceutical Compositions

The compounds disclosed herein may be formulated into composition suitable for administration, using one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, capsules, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) pulmonarily, or (9) nasally.

Examples of suitable aqueous and nonaqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, dispersing agents, lubricants, and/or antioxidants. Prevention of the action of microorganisms upon the compounds disclosed herein may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Methods of preparing these formulations or compositions include the step of bringing into association a compound with the carrier and, optionally, one or more accessory ingredients. In general, the formulations are prepared by uniformly and intimately bringing into association a compound with liquid carriers, or finely divided solid carriers, or both, and then, if necessary, shaping the product.

When the compounds disclosed herein are administered as pharmaceuticals, to humans and animals, they can be given per se or as a pharmaceutical composition containing, for example, about 0.1 to 99%, or about 10 to 50%, or about 10 to 40%, or about 10 to 30, or about 10 to 20%, or about 10 to 15% of active ingredient in combination with a pharmaceutically acceptable carrier.

Actual dosage levels of the active ingredients in the pharmaceutical compositions may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

In general, a suitable daily dose of a compound disclosed herein will be that amount of the compound which is the lowest dose effective to produce a therapeutic effect. Such an effective dose will generally depend upon the factors described above. Generally, oral, intravenous and subcutaneous doses of the compounds for a patient, when used for the indicated effects, will range from about 0.0001 to about 200 mg, or about 0.001 to about 100 mg, or about 0.01 to about 100 mg, or about 0.1 to about 100 mg per, or about 1 to about 50 mg per kilogram of body weight per day.

The compounds can be administered daily, every other day, three times a week, twice a week, weekly, or bi-weekly. The dosing schedule can include a "drug holiday," i.e., the drug can be administered for two weeks on, one week off, or three weeks on, one week off, or four weeks on, one week off, etc., or continuously, without a drug holiday. The compounds can be administered orally, intravenously, intraperitoneally, topically, transdermally, intramuscularly, subcutaneously, intranasally, sublingually, or by any other route.

The subject receiving this treatment is any animal in need, including primates, in particular humans, and other mammals such as equines, cattle, swine and sheep; and poultry and pets in general.

Methods of Treatment

Hedgehog signaling is essential in many stages of development, especially in formation of left-right symmetry. Loss or reduction of hedgehog signaling leads to multiple developmental deficits and malformations, one of the most striking of which is cyclopia.

Many tumors and proliferative conditions have been shown to depend on the hedgehog pathway. The growth of such cells and survival can be affected by treatment with the compounds disclosed herein. Recently, it has been reported that activating hedgehog pathway mutations occur in sporadic basal cell carcinoma (Xie, et al., *Nature* (1998) 391:90-92) and primitive neuroectodermal tumors of the central nervous system (Reifenberger, et al., *Cancer Res* (1998) 58:1798-1803). Uncontrolled activation of the hedgehog pathway has also been shown in numerous cancer types such as GI tract cancers including pancreatic, esophageal, gastric cancer (Berman, et al., *Nature* (2003) 425:846-851, Thayer, et al., *Nature* (2003) 425:851-856) lung cancer (Watkins, et al., *Nature* (2003) 422:313-317, prostate cancer (Karhadkar, et al. *Nature* (2004) 431:707-712, Sheng, et al., *Molecular Cancer* (2004) 3:29-42, Fan, et al., *Endocrinology* (2004) 145:3961-3970), breast cancer (Kubo, et al., *Cancer Research* (2004) 64:6071-6074, Lewis, et al., *Journal of Mammary Gland Biology and Neoplasia* (2004) 2:165-181) and hepatocellular cancer (Sicklick, et al., ASCO conference (2005), Mohini, et al., AACR conference (2005)).

For example, small molecule inhibition of the hedgehog pathway has been shown to inhibit the growth of basal cell carcinoma (Williams, et al., *PNAS* (2003) 100:4616-4621), medulloblastoma (Berman, et al., *Science* (2002) 297:1559-1561), pancreatic cancer (Berman, et al., *Nature* (2003) 425:846-851), gastrointestinal cancers (Berman, et al., *Nature* (2003) 425:846-851, published PCT application WO 05/013800), esophageal cancer (Berman, et al., *Nature* (2003) 425:846-851), lung cancer (Watkins, et al., *Nature* (2003) 422:313-317), and prostate cancer (Karhadkar, et al., *Nature* (2004) 431:707-712).

In addition, it has been shown that many cancer types have uncontrolled activation of the hedgehog pathway, for example, breast cancer (Kubo, et al., *Cancer Research* (2004) 64:6071-6074), heptacellular cancer (Patil, et al., 96th Annual AACR conference, abstract #2942 (2005); Sicklick, et al., ASCO annual meeting, abstract #9610 (2005)), hematological malignancies (Watkins and Matsui, unpublished results), basal carcinoma (Bale & Yu, *Human Molec. Genet.* (2001) 10:757-762, Xie, et al., *Nature* (1998) 391:90-92), medulloblastoma (Pietsch, et al., *Cancer Res.* (1997) 57:2085-2088), and gastric cancer (Ma, et al., *Carcinogenesis*, May 19, 2005 (Epub) (2005)). In addition, investigators have found that small molecule inhibition of the hedgehog pathway has been shown to ameliorate the symptoms of psoriasis (Tas, et al., *Dermatology* (2004) 209:126-131). As shown in the Examples, the compounds disclosed herein have been shown to modulate the hedgehog pathway, and selected compounds have been shown to inhibit tumor growth. It is therefore believed that these compounds can be useful to treat a variety of hyperproliferative disorders, such as various cancers.

Proliferative disorders that can be treated using the methods disclosed herein include: lung cancer (including small cell lung cancer and non small cell lung cancer), other cancers of the pulmonary system, medulloblastoma and other brain cancers, pancreatic cancer, basal cell carcinoma, breast cancer, prostate cancer and other genitourinary cancers, gastrointestinal stromal tumor (GIST) and other cancers of the gastrointestinal tract, colon cancer, colorectal cancer, ovarian cancer, cancers of the hematopoietic system (including multiple myeloma, acute lymphocytic leukemia, acute myelocytic leukemia, chronic myelocytic leukemia, chronic lymphocytic leukemia, Hodgkin lymphoma, and non-Hodgkin lymphoma, and myelodysplastic syndrome), polycythemia Vera, Waldenstrom's macroglobulinemia, heavy chain disease, soft-tissue sarcomas, such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, melanoma, and other skin cancers, adenocarcinoma, sweat gland carcinoma, sebaceous gland carcinoma, papillary carcinoma, papillary adenocarcinomas, stadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, bladder carcinoma, and other genitourinary cances, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, retinoblastoma, endometrial cancer, follicular lymphoma, diffuse large B-cell lymphoma, mantle cell lymphoma, hepatocellular carcinoma, thyroid cancer, gastric cancer, esophageal cancer, head and neck cancer, small cell cancers, essential thrombocythemia, agnogenic myeloid metaplasia, hypereosinophilic syndrome, systemic mastocytosis, familiar hypereosinophilia, chronic eosinophilic leukemia, thyroid cancer, neuroendocrine cancers, and carcinoid tumors. Additional disorders include Gorlin's syndrome and psoriasis The subject receiving this treatment is any animal in need, including primates, in particular humans, and other mammals such as equines, cattle, swine and sheep; and poultry and pets in general.

The hedgehog inhibitors disclosed herein can be combined with other cancer treatments. For example, they can be combined with surgical treatments; radiation; biotherapeutics (such as interferons, cytokines—e.g., Interferon α, Interferon γ, and tumor necrosis factor, hematopoietic growth factors, monoclonal serotherapy, vaccines and immunostimulants); antibodies (e.g., Avastin, Erbitux, Rituxan, and Bexxar); endocrine therapy (including peptide hormones, corticosteroids, estrogens, androgens and aromatase inhibitors); antiestrogens (e.g., Tamoxifen, Raloxifene, and Megestrol); LHRH agonists (e.g., goscrclin and Leuprolide acetate); antiandrogens (e.g., flutamide and Bicalutamide); gene therapy; bone marrow transplantation; photodynamic therapies (e.g., vertoporfin (BPD-MA), Phthalocyanine, photosensitizer Pc4, and Demethoxy-hypocrellin A (2BA-2-DMHA)); and chemotherapeutics.

Examples of chemotherapeutics include gemcitabine, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, prednisolone, dexamethasone, cytarbine, campathecins, bleomycin, doxorubicin, idarubicin, daunorubicin, dactinomycin, plicamycin, mitoxantrone, asparaginase, vinblastine, vincristine, and vinorelbine. Additional agents include nitrogen mustards (e.g., cyclophosphamide, Ifosfamide, Trofosfamide, Chlorambucil, Estramustine, and Melphalan), nitrosoureas (e.g., carmustine (BCNU) and Lomustine (CCNU)), alkylsulphonates (e.g., busulfan and Treosulfan), triazenes (e.g., Dacarbazine and Temozolomide), platinum containing compounds (e.g., Cisplatin, Carboplatin, and oxaliplatin), vinca alkaloids (e.g., vincristine, Vinblastine, Vindesine, and Vinorelbine), taxoids (e.g., paclitaxel and Docetaxol), epipodophyllins (e.g., etoposide, Teniposide, Topotecan, 9-Aminocamptothecin, Camptoirinotecan, Crisnatol, Mytomycin C, and Mytomycin C), antimetabolites, DHFR inhibitors (e.g., methotrexate and Trimetrexate), IMP dehydrogenase Inhibitors (e.g., mycophenolic acid, Tiazofurin, Ribavirin, and EICAR), ribonucleotide reductase Inhibitors (e.g., hydroxyurea and Deferoxamine), uracil analogs (e.g., Fluorouracil, Floxuridine, Doxifluridine, Ratitrexed, and Capecitabine), cytosine analogs (e.g., cytarabine (ara C), Cytosine arabinoside, and Fludarabine), purine analogs (e.g., mercaptopurine and Thioguanine), Vitamin D3 analogs (e.g., EB 1089, CB 1093, and KH 1060), isoprenylation inhibitors (e.g., Lovastatin), dopaminergic neurotoxins (e.g., 1-methyl-4-phenylpyridinium ion), cell cycle inhibitors (e.g., staurosporine), actinomycins (e.g., Actinomycin D and Dactinomycin), bleomycins (e.g., bleomycin A2, Bleomycin B2, and Peplomycin), anthracyclines (e.g., daunorubicin, Doxorubicin (adriamycin), Idarubicin, Epirubicin, Pirarubicin, Zorubicin, and Mitoxantrone), MDR inhibitors (e.g., verapamil), $Ca^{2+}$ ATPase inhibitors (e.g., thapsigargin), imatinib, thalidomide, lenalidomide, erlotinib, gefitinib, sorafenib, and sunitinib, and proteasome inhibitors, including bortezomib.

When the hedgehog inhibitors disclosed herein are administered in combination with other treatments, such as additional therapeutics or with radiation or surgery, the doses of each agent or therapy will in most instances be lower than the corresponding dose for single-agent therapy. Also, in general, the hedgehog inhibitors described herein and the second therapeutic agent do not have to be administered in the same pharmaceutical composition, and may, because of different physical and chemical characteristics, be administered by different routes. For example, one compound can be administered orally, while the second therapeutic is administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The hedgehog inhibitor and the second therapeutic agent and/or radiation may be administered concurrently (e.g., simultaneously, essentially simultaneously or within the same treatment protocol) or sequentially (i.e., one followed by the other, with an optional time interval in between), depending upon the nature of the proliferative disease, the condition of the patient, and the actual choice of second therapeutic agent and/or radiation to be administered.

If the hedgehog inhibitor, and the second therapeutic agent and/or radiation are not administered simultaneously or essentially simultaneously, then the optimum order of administration may be different for different conditions. Thus, in certain situations the hedgehog inhibitor may be administered first followed by the administration of the second therapeutic agent and/or radiation; and in other situations the second therapeutic agent and/or radiation may be administered first followed by the administration of a hedgehog inhibitor. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the second therapeutic agent and/or radiation may be administered first, especially if it is a cytotoxic agent, and then the treatment continued with the administration of a hedgehog inhibitor followed, where determined advantageous, by the administration of the second therapeutic agent and/or radiation, and so on until the treatment protocol is complete.

EXEMPLIFICATION

The invention now being generally described, it will be more readily understood by reference to the following examples, which are included merely for purposes of illustration of certain aspects and embodiments of the present invention, and are not intended to limit the invention.

Example 1

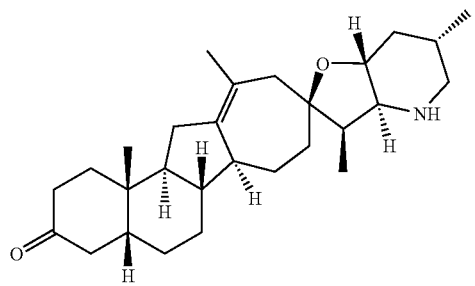

Step A

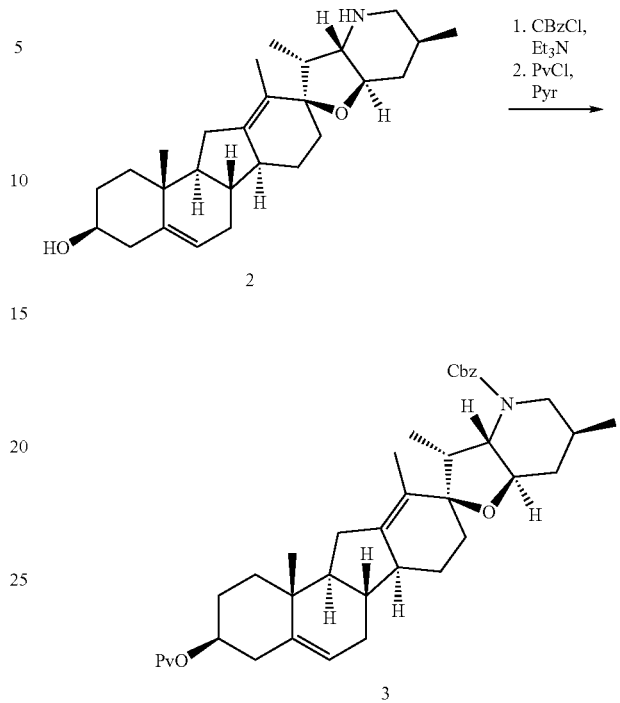

Recrystallized cyclopamine 2 (14.1 g, 34.0 mmol, 1 eq) is dissolved in anhydrous DCM (70 mL) and anhydrous MeOH (29 mL). The clear solution is cooled, and triethylamine (10.4 g, 102.7 mmol, 3 eq) followed by benzyl chloroformate (6.20 g, 36.3 mmol, 1.1 eq) is added. After the addition is complete, the solution is stirred in the ice bath for 30 min. Three portions of benzyl chloroformate (3×0.35 g, 3.46 mmol, 0.03 eq) are added over the 3 h. The reaction is slowly quenched with water (71 mL), while maintaining the temperature below 20° C. The mixture is stirred for 15 min before the layers are settled and separated. The organic layer is dried over sodium sulfate and filtered. The combined filtrate is buffered with anhydrous pyridine (30 mL), concentrated, and solvent exchanged with additional anhydrous pyridine (43 mL) and concentrated.

The solution of the compound in pyridine (43 mL) is further diluted with additional anhydrous pyridine (85 mL). Trimethylacetyl chloride (8.3 g, 68.7 mmol, 2 eq) is added slowly to the reaction mixture, and the reaction is heated to 45° C. The reaction is stirred at 45° C. for 30 min. The reaction is cooled and quenched by the addition of anhydrous MeOH (4.5 mL). The quenched reaction mixture is stirred at rt for 40 min and then diluted with toluene (97 mL) and is treated sequentially with water (35 mL) and a 10 wt % aqueous sodium carbonate solution (100 mL). After vigorous stirring, the layers are separated and the organic layer is washed twice with water (2×100 mL), dried over sodium sulfate, and filtered. The filter cake is rinsed with toluene (49 mL) and discarded. The combined filtrates are concentrated, and solvent exchanged with concentration to toluene (145 mL) and further concentrating to dryness. The product is recrystallized from toluene and heptane. The crystalline product is isolated by suction filtration, washed with cold heptane and dried to a constant weight to afford 15.1 g of the desired product.

Step B

Step C

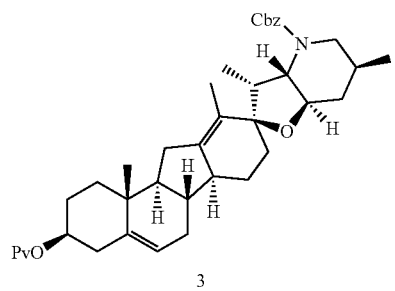
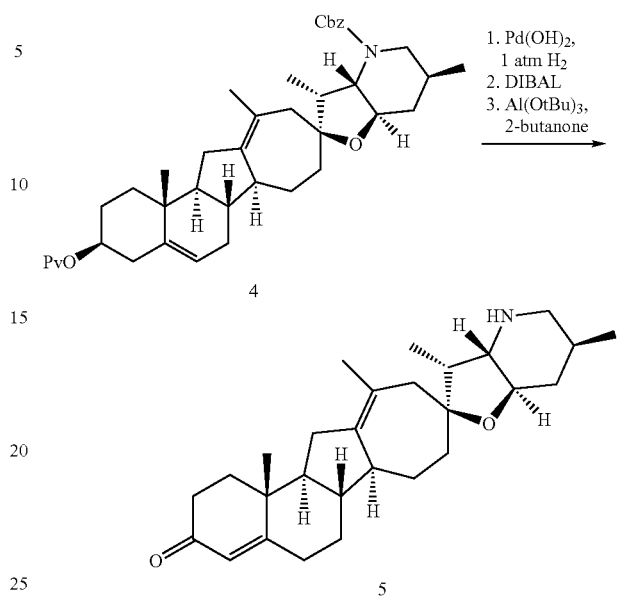

Bis(2,6-dimethyphenyl)phosphate (10.65 g, 34.8 mmol, 3.1 eq) is dried by concentration from anhydrous DCM (42 mL) and held under a nitrogen atmosphere. The phosphate is then redissolved in anhydrous DCM (110 mL). In a separate flask, a solution of neat diethylzinc (4.17 g, 33.8 mmol, 3.0 eq) in anhydrous DCM (35 mL) is prepared and cooled to −25° C. The phosphate solution is slowly transferred to the vessel containing the diethylzinc solution over 1 h, maintaining the temperature at or below −10° C. The clear ethylzinc phosphate solution is warmed to 0° C. and stirred for 15 min. Diiodomethane (9.25 g, 34.5 mmoles, 3.0 eq) is slowly added to the ethylzinc phosphate solution, maintaining the reaction temperature between 0 and 5° C. After the addition is complete, the zinc carbenoid solution is stirred for an additional 20 min.

In a separate flask, compound 3 (7.20 g, 11.4 mmol, 1 eq) is dissolved in anhydrous DCM (36 mL) and transferred to the reaction flask. After the addition is complete, the ice bath is removed and the reaction mixture is allowed to warm to rt. After 6 h the contents of the flask are cooled to −5° C. A solution of methanesulfonic acid (3.38 g, 35.2 mmol, 3.1 eq) in anhydrous DCM (3 mL) is added, maintaining the reaction temperature below −45° C. After 10 min morpholine (20 g, 230 mmol, 20 eq) is added to the reaction mixture, maintaining the reaction temperature below −40° C. The reaction is allowed to warm to rt overnight. The morpholine salts are removed by filtration and the filter cake rinsed with DCM (22 mL). The combined filtrates are washed with 2N aqueous hydrochloric acid (2×140 mL), 5% aqueous sodium bicarbonate (140 mL), 5% aqueous sodium bicarbonate (70 mL) and 5% aqueous sodium bisulfite (70 mL), and brine (144 mL). The organic layer is dried over magnesium sulfate and filtered. Without going to dryness, the DCM solution is concentrated and solvent exchanged with methanol (280 mL). The suspension are chilled with an ice bath and stirred for 40 minutes. The solids are isolated by filtration, washed twice with cold methanol (2×25 mL), and dried to a constant weight to afford 5.94 g of the desired product.

In a round bottom flask, compound 4 (11.67 g, 18.1 mmol, 1 eq) and 20% palladium hydroxide on wet carbon (2.40 g, 1.71 mmol, 0.09 eq) are placed under a nitrogen atmosphere and diluted with EtOAc (115 mL) and toluene (60 mL). The solution is degassed with nitrogen (3×) with evacuation/purge cycles, and the process is repeated for hydrogen. The suspension is vigorously stirred at rt for 1.5 h. The hydrogen atmosphere is replaced with nitrogen. Ethylenediamine (0.57 g, 9.5 mmol, 0.52 eq) is added to the reaction, and the resulting mixture stirred for 20 min. The solution is filtered under nitrogen, and the filtrate is washed with a 2% (wt/wt) aqueous solution of ethylenediamine (125 mL) then water (130 mL), and then dried over sodium sulfate. The drying agent is removed by filtration and the filtrate is concentrated to dryness under vacuum. The solids that remained are chased with toluene (2×55 mL) on the rotary evaporator and the resulting material used without further purification in the next step The material from the previous step is dissolved in anhydrous DCM (26 mL). The resulting clear solution is added to a 1 M solution of DIBAL in DCM (65 mL, 65 mmol, 3.6 eq) while maintaining the reaction temperature between −10 and −25° C. After 30 min the reaction is quenched with acetone (13 mL), maintaining the reaction temperature at or below 0° C. After stiffing the quenched reaction mixture for 17 min, it is added in portions to a flask containing a cold, stirred solution of 20% (wt/wt) aqueous Rochelle salt (200 mL). The resulting gelatinous suspension is stirred at rt for 15 h. After stiffing, the clean layers are separated and the aqueous layer back extracted with DCM (30 mL). The combined organic layers are washed with water (60 mL) and dried over sodium sulfate. The drying agent is removed by filtration and discarded. The filtrate is concentrated under vacuum and solvent exchanged to toluene (225 mL added in portions). The resulting solution is further concentrated to a suspension (50 mL) and diluted with heptane (115 mL). The resulting mixture is heated until turning homogeneous (92° C.). The solution is cooled slowly over 12 h to 15° C., and then held for 16 additional h. The crystalline product is isolated by suction filtration, washed with heptane (2×75 mL) and dried to a constant weight to afford 7.70 g of the desired product.

A round bottom flask is sequentially charged with the homo-allylic alcohol (7.50 g, 17.6 mmol, 1 eq), aluminum tri-tert-butoxide (6.10 g, 24.8 mmol, 1.4 eq), anhydrous toluene (115 mL), and 2-butanone (90 g, 1.24 mol, 7 eq). The suspension is heated under a nitrogen atmosphere to 75° C. for 16 h. The reaction temperature is then allowed to cool to 49° C. Aqueous 20% (w/w) potassium sodium tartrate solution (226 g) is added to the stirred suspension. The suspension is stirred at rt for 3.5 h. The layers are separated. The organic layer washed with aqueous 20% Rochelle salt (2×250 mL) and water (225 mL), then dried over sodium sulfate and filtered. The residue is rinsed with toluene (30 mL) and discarded. The combined organics are concentrated to dryness. Residual reaction solvents are removed from the material by concentrating from 2-propanol (250 mL added portion-wise) to a final solution mass of 44 g. Solvent exchange from 2-propanol to heptane (275 mL added portion-wise) to a final solution mass is 41 g fully precipitated the desired product. The suspension is diluted with of additional heptane (40 mL), stirred at rt for 1 h, and filtered. The product is washed with n-heptane (17 mL) and dried to afford 5.4 g of the desired product.

Example 2

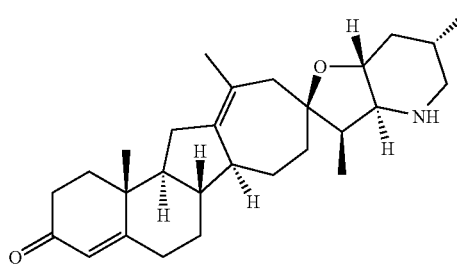

Step A

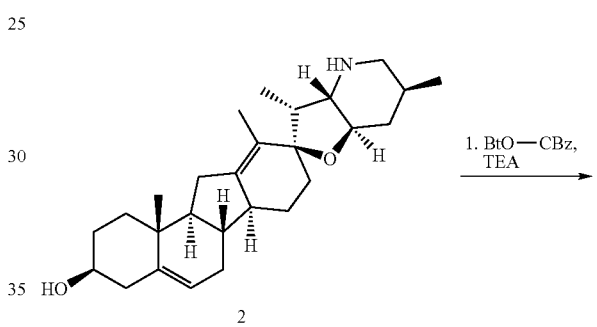

Step D

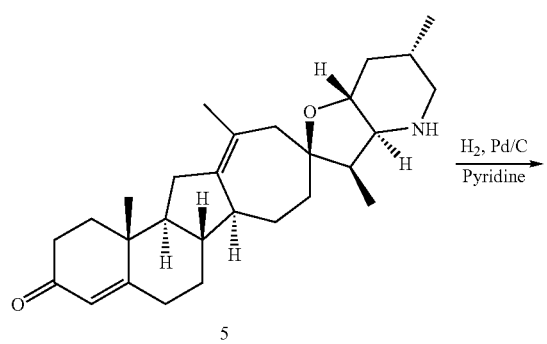

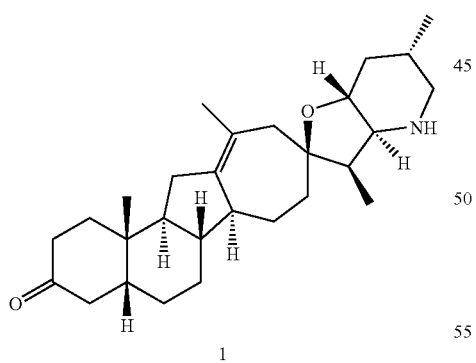

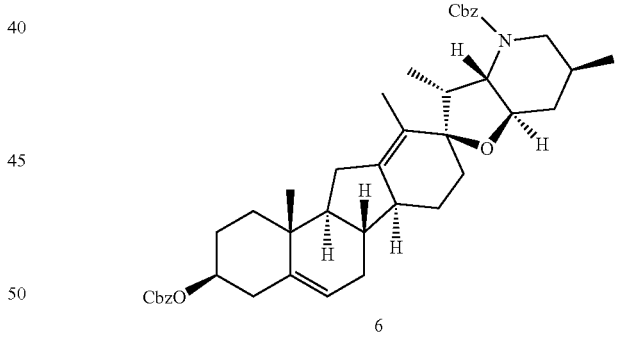

A round-bottom flask is charged with starting material (110 mg, 0.26 mmol, 1 eq) and 10% palladium on carbon (106 mg). The solids are suspended in pyridine (4 mL). The suspension is placed under hydrogen atmosphere (1 atm) and the mixture is stirred overnight at rt. The reaction mixture is filtered through Celite® and the filtrate concentrated in vacuo. The crude material is purified using silica gel flash chromatography (MeOH/DCM 5:95) to afford 93 mg of the desired compound. ([M+H]=426.6 m/z).

Cyclopamine 2 (5.02 g, 12.2 mmol, 1.0 eq) is dissolved in anhydrous pyridine (25 mL). DMAP (300 mg, 2.44 mmol, 0.2 eq.) and triethyl amine (5.5 mL, 39.1 mmol, 3.2 eq) are added, followed by BtO-Cbz (10.5 g, 39.1 mmol, 3.2 eq) and heated at 40° C. for 2 h. The mixture is cooled to rt, treated with 30 mL water, heated to get a homogeneous solution and allowed to cool to room temp. The white precipitate that formed is collected by filtration, the filter cake is washed with portions of water (3×50 mL), and dried in air to afford 9.53 g of crude material which is crystallized from toluene/heptanes (1:9, 70 mL) to give 6.75 g of the desired product.

Step B

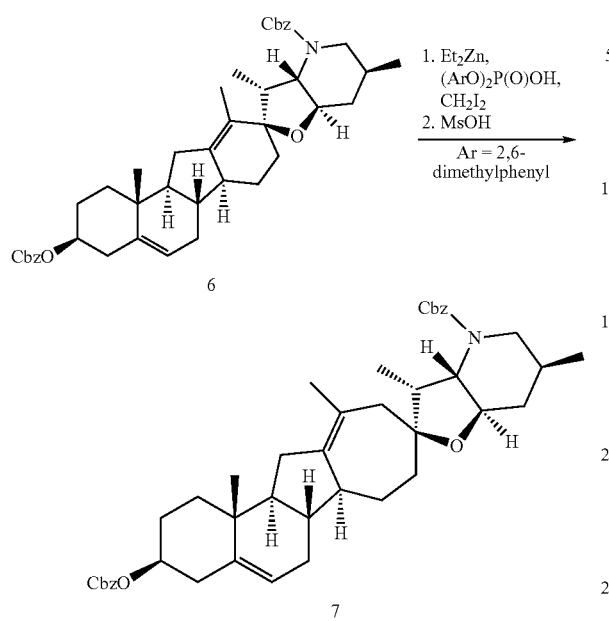

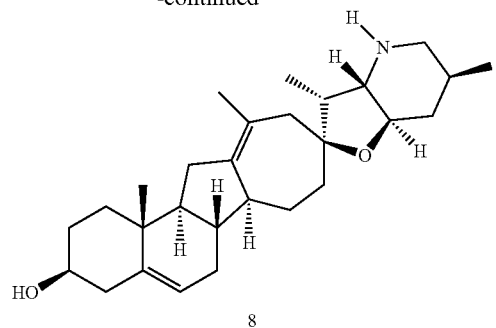

To a solution of diethyl zinc (572 mg, 482 µL, 4.63 mmol, 3.00 eq) in 5.0 mL DCM at −20° C. is added a solution of bis-(2,6-Dimethylphenyl)phosphoric acid (1.42 g, 4.63 mmol, 3.00 eq) in DCM (15 mL) maintaining the reaction temperature below −8° C. The solution is aged for 15 min. at 0° C., neat diiodomethane (1.24 g, 374 µL, 3.00 eq) is added, aged for 15 min. at 0° C. before adding a solution of (Bis-CBzcyclopamine, 1.05 g, 1.54 mmol, 1.0 eq), in DCM (10 mL). The cooling bath is replaced by a water bath at rt and maintained at rt for 4.5 h. The mixture is cooled to −76° C. with a dry ice-acetone bath and treated drop wise with methanesulfonic acid DCM solution (0.6 mL 50% v/v solution 4.63 mmol, 3.0 eq) maintaining the reaction temperature below −74° C. The mixture is aged for 15-20 min. and quenched drop wise with morpholine (2.69 g, 2.70 mL, 20 eq) maintaining the reaction temperature below −65° C. The cooling bath is removed, the reaction mixture is stirred for 16-18 h., the white precipitate is filtered off, and the filtrate is successively washed with 2.0 M HCl (2×20 mL), satd. sodium bicarbonate (2×20 mL), water (2×20 mL) and brine (20 mL). Dried over magnesium sulfate, concentrated in vacuo to dryness and the crude is purified by silica gel flash chromatography (hexanes/EtOAc 17:3→4:1) to afford 924 mg (1.33 mmol, 86%) of the desired product.

Step C

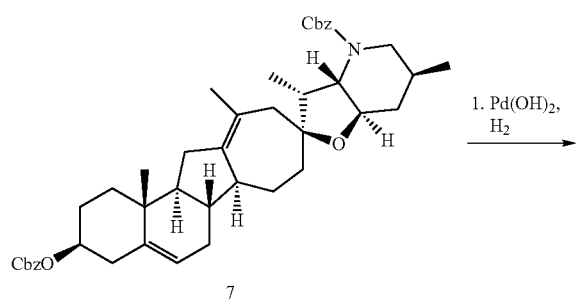

To a solution of compound 7 (4.05 g, 5.83 mmol, 1 eq) in a solution of EtOAc:toluene (2:1, 60 mL) is added of 20% palladium hydroxide on carbon (823 mg, 0.583 mmol, 0.1 eq.). The flask is evacuated and filled with hydrogen three times. The mixture is stirred under an atmosphere of hydrogen for 1 h. Neat ethylene diamine (0.38 mL) is added, stirred for 1 h., and the catalyst is filtered off. The filter cake is washed twice with EtOAc:toluene (2:1, 12 mL). The combined filtrates are washed with a 2% aqueous solution of ethylene diamine (3×20 mL), dried over sodium sulfate and concentrated in vacuo to give 2.46 g as a white crystalline solid.

Step D

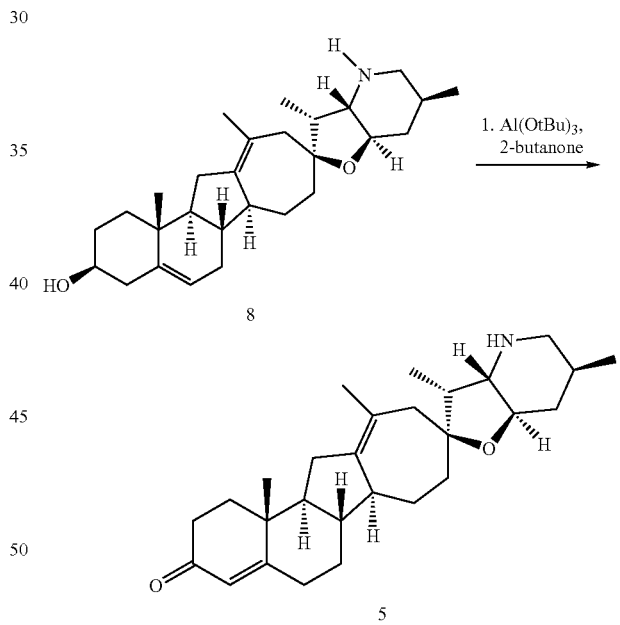

A round bottom flask is sequentially charged with the homo-allylic alcohol 8 (7.50 g, 17.6 mmol, 1 eq), aluminum tri-tert-butoxide (6.10 g, 24.8 mmol, 1.4 eq), anhydrous toluene (115 mL), and 2-butanone (90 g, 1.24 mol, 7 eq). The suspension is heated under a nitrogen atmosphere to 75° C. for 16 h. The reaction temperature is then allowed to cool to 49° C. Aqueous 20% (w/w) potassium sodium tartrate solution (226 g) is added to the stirred suspension. The suspension is stirred at rt for 3.5 h. The layers are separated. The organic layer washed with aqueous 20% Rochelle's salt (2×250 mL) and water (225 mL), then dried over sodium sulfate and filtered. The residue is rinsed with toluene (30 mL) and discarded. The combined organics are concentrated to dryness.

Residual reaction solvents are removed from the material by concentrating from 2-propanol (250 mL added portion-wise) to a final solution mass of 44 g. Solvent exchange from 2-propanol to n-heptane (275 mL added portion-wise) to a final solution mass of 41 g fully precipitated the desired product. The suspension is diluted with of additional n-heptane (40 mL), stirred at rt for 1 h, and filtered. The product is washed with n-heptane (17 mL) and dried to afford 5.4 g of the desired product.

Step E

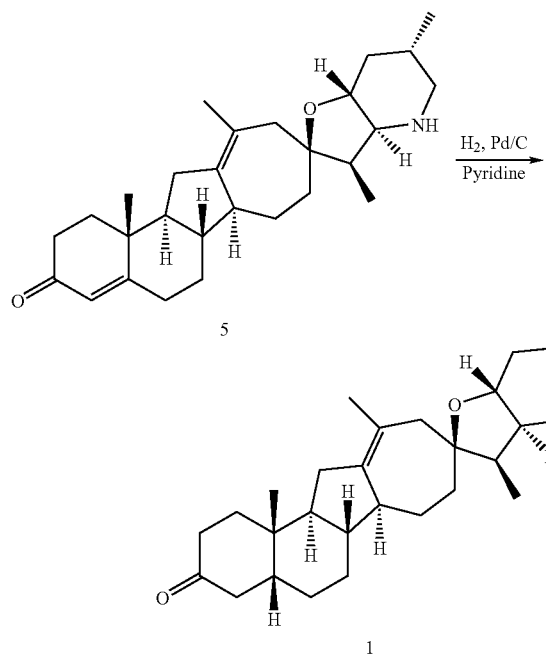

A round-bottom flask is charged with starting material (110 mg, 0.26 mmol, 1 eq) and 10% palladium on carbon (106 mg). The solids are suspended in pyridine (4 mL). The suspension is placed under hydrogen atmosphere (1 atm) and the mixture is stirred overnight at rt. The reaction mixture is filtered through Celite® and the filtrate concentrated in vacuo. The crude material is purified using silica gel flash chromatography (MeOH/DCM 5:95) to afford 93 mg of the desired compound. ([M+H]=426.6 m/z).

Example 3

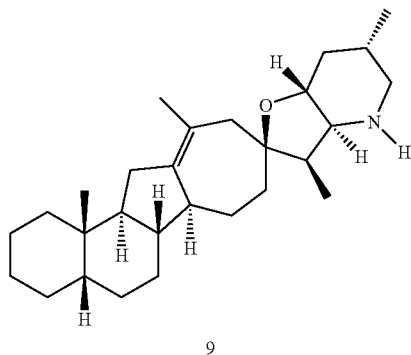

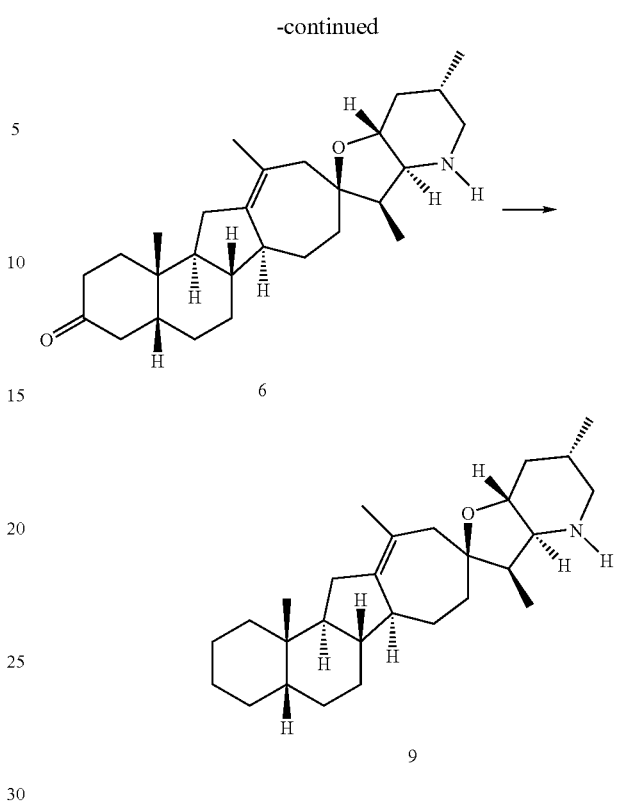

In a seal tube, ketone 6 (85 mg, 0.199 mmol, 1 equiv.) was charged and triethyleneglycol (2 mL) was added followed by hydrazine monohydrate (500 mg, 10 mmol, 50 equiv.) and potassium carbonate (138 mg, 1 mmol, 5 equiv.). The tube was sealed and the reaction was heated at 150° C. for 16 h. The reaction was cooled to rt and water was added. The residue was extracted with chloroform (3×). The combined organic layers are washed with water, dried over $Na_2SO_4$, and concentrated to dryness. The colorless oil was purified using silica gel flash chromatography (DCM/MeOH 96:4). The purified fractions are pooled and concentrated to dryness. The resulting oil was dissolved in MTBE and washed with water (2×), 2N NaOH, and then brine. The combined organic layers are dried over $Na_2SO_4$, filtered and evaporated to afford 64 mg of the desired material as a white foam. ([M+H]=412.7 m/z).

Example 4

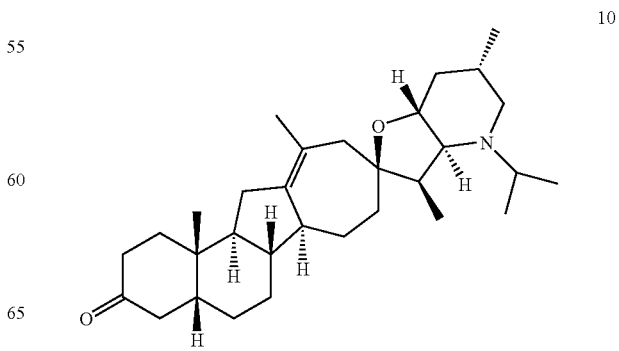

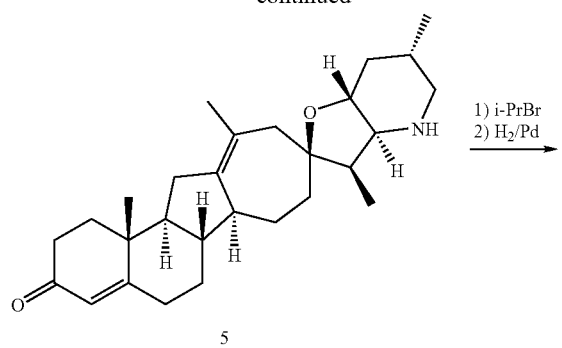

5

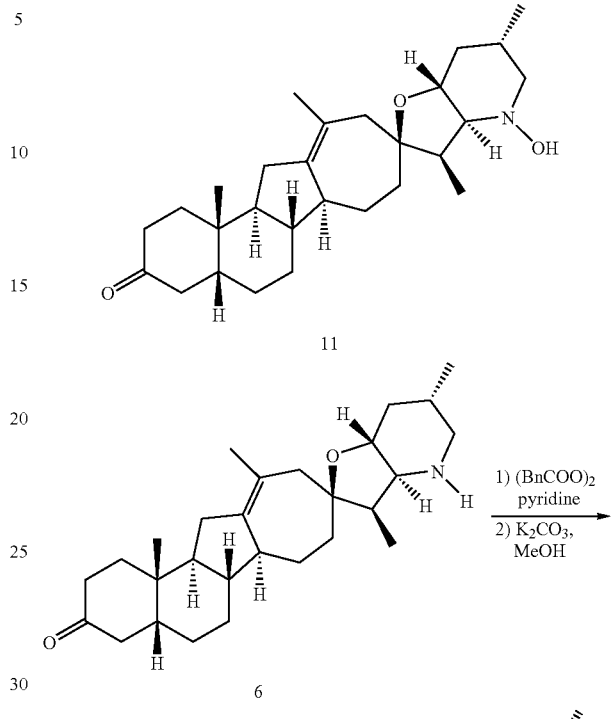

Example 5

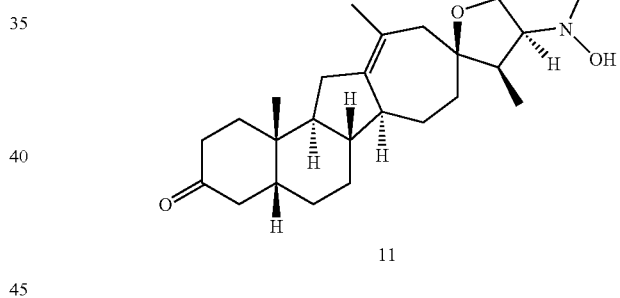

A sealed tube was charged with compound 5 (223 mg, 0.52 mmol, 1 eq) and DMF (1 mL). 2-Bromopropane (1.3 g, 10.5 mmol, 20 eq) and $Na_2CO_3$ (73 mg, 0.68 mmol, 1.3 eq) were added and the flask was sealed and heated to 50° C. The mixture was stirred for 16 h at which point ~70% conversion was observed. Additional (0.26 g, 2.12 mmol, 4 eq) was added. The reaction was stirred for 2 h and additional 2-bromopropane (0.13 g, 1.1 mmol, 2 eq) was added. The reaction was stirred for another 1 h. The reaction was cooled to rt and water was added. The residue was extracted with MTBE (3×). The organic layers were combined washed with brine, dried over $Na_2SO_4$, filtered, and concentrated to dryness. The white foam was purified using silica gel flash chromatography (DCM/MeOH 99:1) to give 206 mg of the N-isopropyl derivative as a white foam.

The N-isopropyl derivative (205 mg, 0.44 mmol, 1 eq) was dissolved in of 4-methoxypyridine (1.5 mL). The flask was placed under inert atmosphere and Pd/C 10% (wet, Aldrich Degussa type E101, 40 mg) was added. The flask was sealed and purged three times with hydrogen and left 16 h under 1 atm of hydrogen. Celite® was added to the reaction mixture. The mixture was filtered through a small pad of Celite® and washed with EtOAc. The organic layer was washed with 1N HCl aq. (2×) then with water. The organic layer was dried over $Na_2SO_4$, filtered though cotton and evaporated to give 34 mg of crude. The aqueous layer was neutralized with 2N KOH and extracted with DCM (3×). The combined organic layers were washed with water, dried over $Na_2SO_4$, filtered though cotton and combined with the initial 34 mg of crude. The crude material was purified using silica gel flash chromatography hexane/EtOAc (6:4) to afford 80 mg of desired product. ([M+H]=468.7 m/z).

In a round-bottom flask, compound 6 (88 mg, 0.21 mmol, 1 eq) was dissolved in anhydrous THF (1 mL). The mixture was cooled to 0° C. Pyridine (84 μL, 1 mmol, 5 eq) and benzoylperoxide (150 mg, 0.62 mmol, 3 eq) were added successively. The homogeneous mixture was gradually warmed to rt over 2 h and stirred overnight at rt. The reaction was quenched by adding saturated $NaHCO_3$. The residue was extracted with MTBE. The combined organic layers were washed with water, dried over $Na_2SO_4$, filtered and concentrated under reduced pressure. The crude was purified using silica gel flash chromatography (hexane/EtOAc (9:1 to 4:1)) to give the N—O derivative product (60 mg, 0.11 mmol) as a white foam. This foam was dissolved in 2 mL of MeOH followed by 2N aqueous KOH (0.4 mL). The reaction mixture was stirred for 1 h. Most of the MeOH was evaporated under a stream of nitrogen and 1N HCl (500 μL) was added. The material was extracted with DCM (3×). The combined organic layers were washed with water, dried over $Na_2SO_4$, filtered and concentrated under reduced pressure. The crude was purified using silica gel flash chromatography (hexanes/EtOAc (from 88:12→1:1)) to yield 11 mg of the desired product. ([M+H]=442.5 m/z).

Example 6

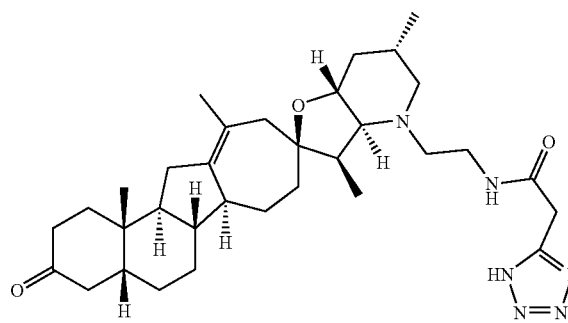
12

Step A

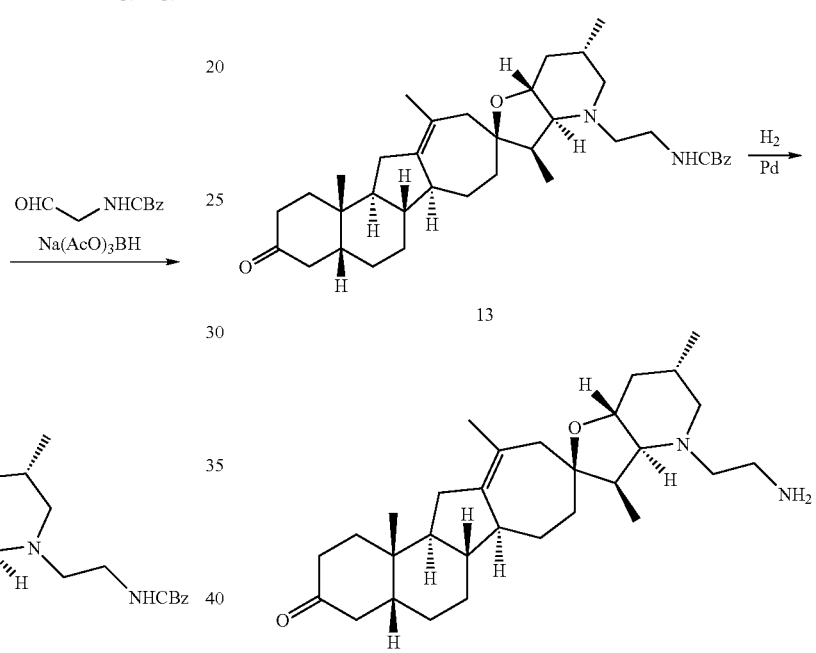

In a round bottom flask, compound 6 (89 mg, 0.209 mmol, 1 eq) and N-(benzyloxycarbonyl)-aminoacetaldehyde (148 mg, 0.85 mmol, 4 eq) were dissolved in DCM (2 mL). Sodium triacetoxyborohydride (177 mg, 0.85 mmol, 4 eq) was added and the reaction was stirred for 3 h at rt. The mixture was poured in saturated aqueous NaHCO$_3$ solution and the residue was extracted with DCM (3×). The combined organic layers were washed with water, dried over Na$_2$SO$_4$, filtered though cotton and evaporated to give a foamy solid (247 mg). The crude was dissolved in EtOAc (2 mL) and treated with of 4M HCl (156 µL). After 30 min a white precipitate slowly formed. The resulting slurry was stirred for 15 min. Filtration gave 120 mg of white solid. The material was dissolved in EtOAc and treated with a saturated aqueous NaHCO$_3$ solution. The organic layer was collect and the aqueous layer and was extracted with EtOAc (2×). The combined organic layers were washed with brine, dried over Na$_2$SO$_4$. Filtration and evaporation gave the desired intermediate. This material was used in the next step without purification.

Step B

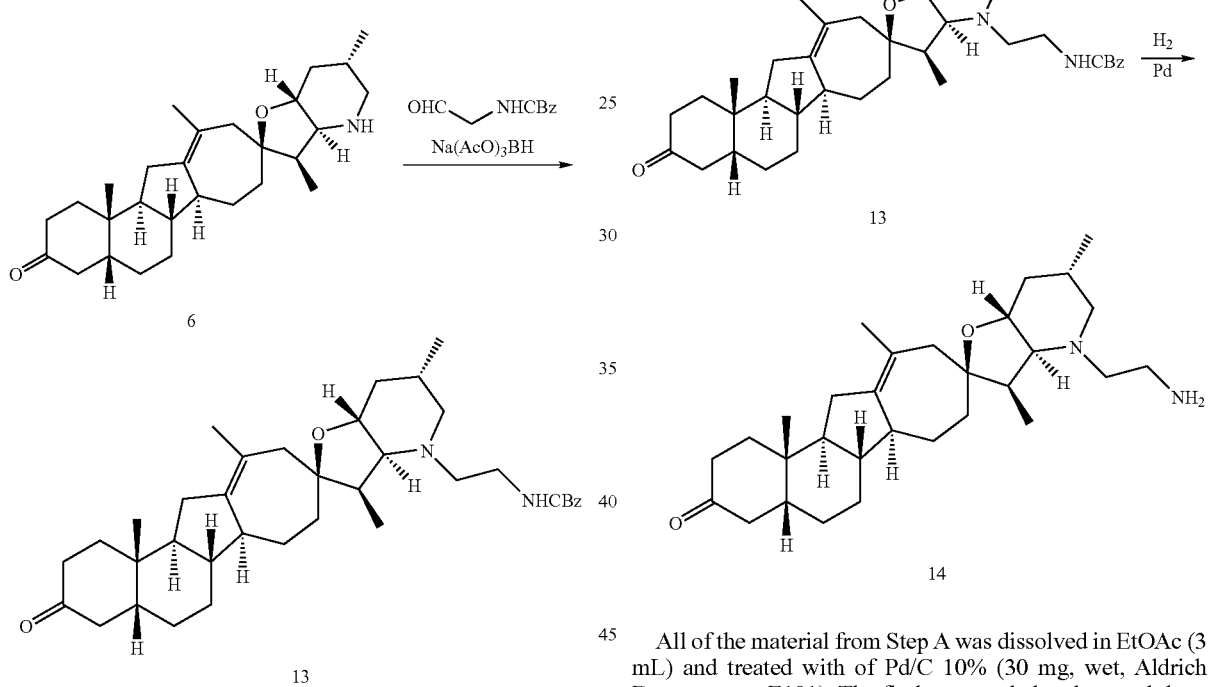

All of the material from Step A was dissolved in EtOAc (3 mL) and treated with of Pd/C 10% (30 mg, wet, Aldrich Degussa type E101). The flask was sealed and purged three times with hydrogen and left overnight under 1 atm of hydrogen. After 16 h, the mixture was filtered through a small pad of Celite® and washed with EtOAc to afford 52 mg of the amine as a white foam.

Step C

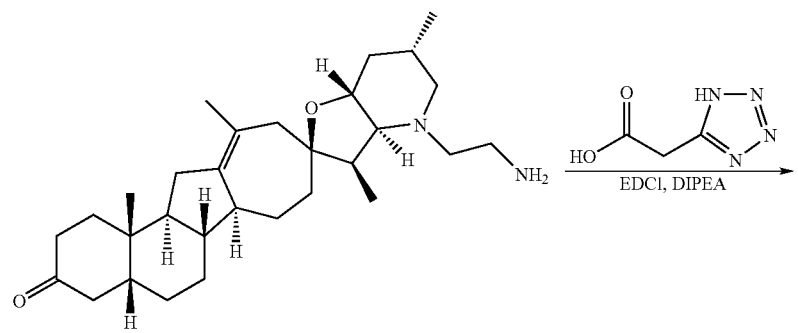

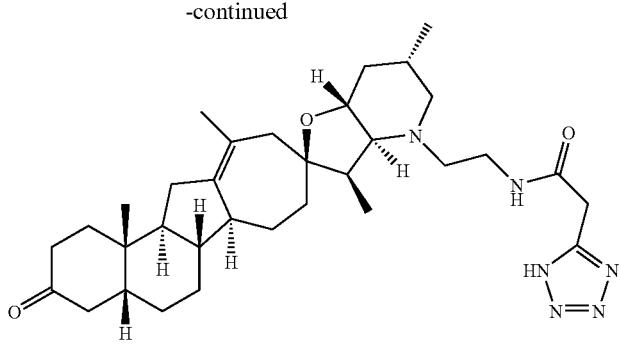

12

A round-bottom flask containing the amine 14 (52 mg, 0.11 mmol, 1 eq) was charged with the 1H-tetrazole-5-acetic acid (21 mg, 0.166 mmol, 1.5 eq), DCM (2 mL), EDCI (42 mg, 0.22 mmol, 2 eq) and N,N-diisopropylethylamine (57 mg, 0.44 mmol, 4 eq). The resulting yellow solution was stirred at rt for 4 h. The reaction was quenched by the addition of saturated aqueous NaHCO₃ solution and the residue was extracted with DCM (3×). The combined organic layers were dried over Na₂SO₄, filtered though cotton and evaporated to give 62 mg of off-white solid. This material was purified using silica gel flash chromatography (MeOH/DCM 5:95→10:90) to afford 31 mg of the desired product. ([M+H] =579.7 m/z).

Example 7

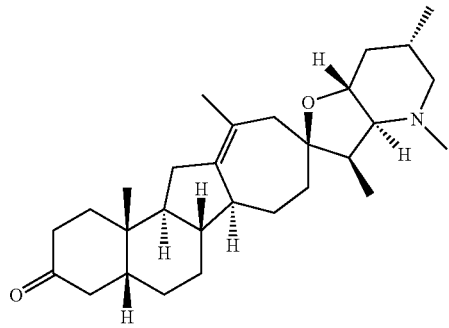

15

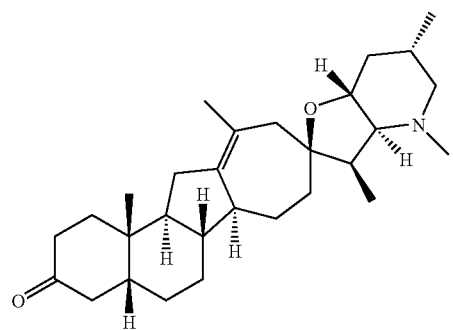

15

A round-bottom flask was charged with starting material (47 mg, 0.110 mmol, 1 eq) and potassium carbonate (150 mg, 1.09 mmol, 10 eq). The solids were suspended in 2 mL of DCM. Iodomethane (14 µL, 0.22 mmol, 2 eq) was added and the mixture was stirred for 2 at rt. TLC (DCM/MeOH 95:5) indicate >90% completion. Iodomethane (14 µL, 0.22 mmol, 2 eq) was added to the reaction mixture, which was stirred for 2 h. The reaction mixture was added water. The phases were separated and the organics were dried and concentrated to dryness. The residue was purified using silica gel flash chromatography (DCM/MeOH 100:0→98:2) afford 34 mg of the desired product ([M+H]=440.5 m/z).

Example 8

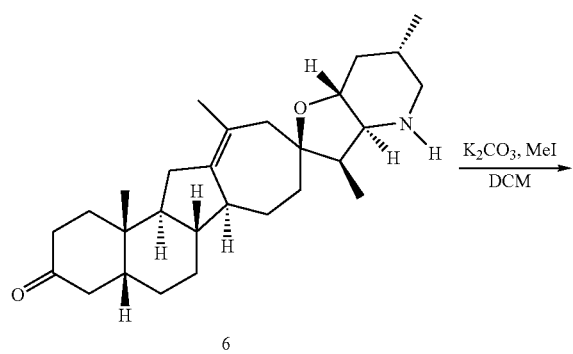

6

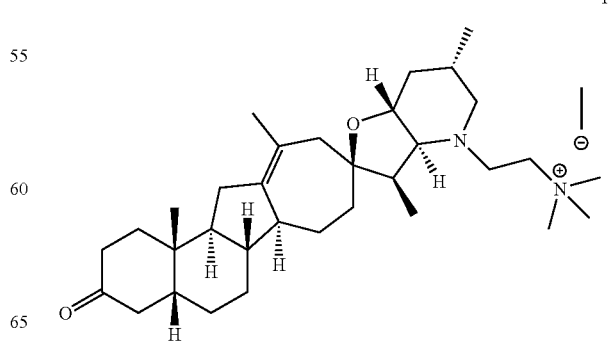

16

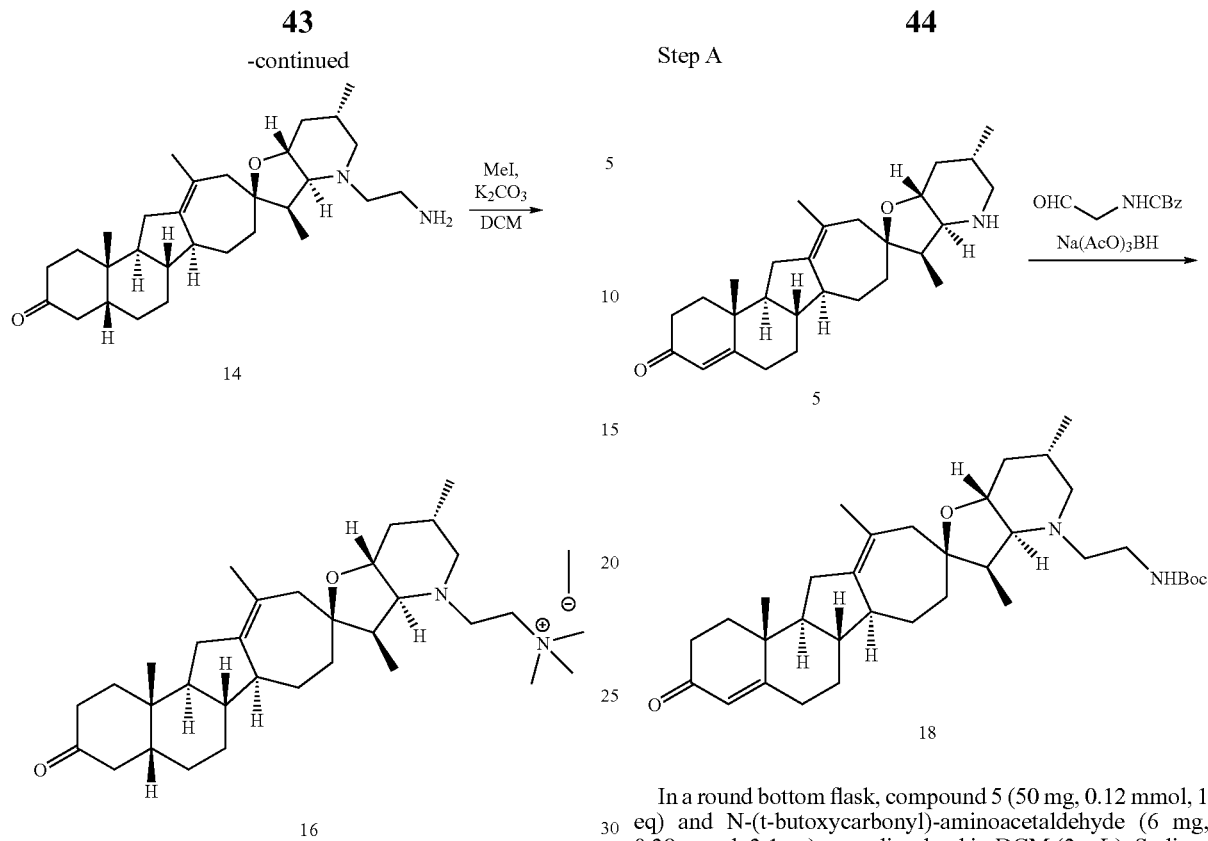

A round-bottom flask was charged with starting material (59 mg, 0.126 mmol, 1 eq) and potassium carbonate (350 mg, 2.5 mmol, 20 eq). The solids were suspended in 3 mL of DCM. The reaction was charged with iodomethane (80 μL, 1.29 mmol, 10 eq) and the mixture was stirred overnight at rt. The reaction mixture was charged with water. The organic phase was separated and the aqueous layer was back extracted with DCM. The combined organic layers were dried and concentrated to dryness. The residue was purified using silica gel flash chromatography. DCM/MeOH (95:5→90:10) to afford 52 mg of the desired product. ([M+H]=639.5 m/z).

Example 9

In a round bottom flask, compound 5 (50 mg, 0.12 mmol, 1 eq) and N-(t-butoxycarbonyl)-aminoacetaldehyde (6 mg, 0.38 mmol, 3.1 eq) were dissolved in DCM (2 mL). Sodium triacetoxyborohydride (8 mg, 0.38 mmol, 3.1 eq) was added and the reaction was stirred for 2 h at rt. The mixture was poured in saturated aqueous NaHCO$_3$ solution and the residue was extracted with DCM (3×). The combined organic layers were washed with water, dried over Na$_2$SO$_4$, filtered though cotton and evaporated to give a foamy solid (95 mg). The crude material was purified using silica gel flash chromatography (EtOAc/Hexanes 1:1) to yield 55 mg of compound 18.

Step B

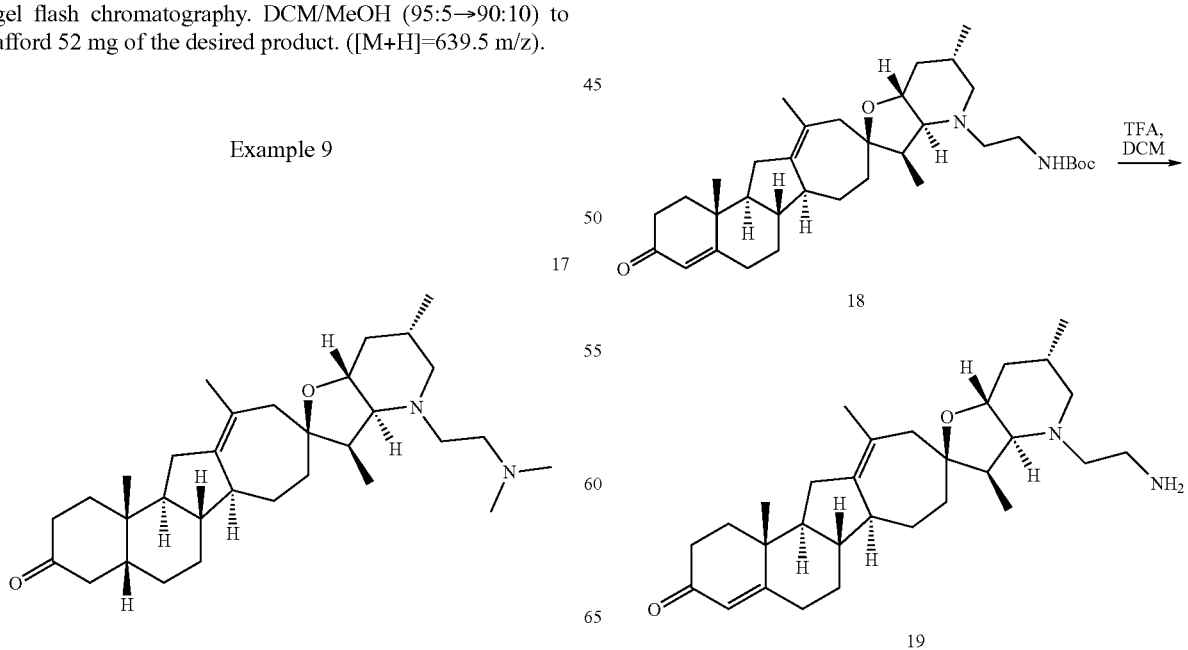

A round-bottom flask was charged with starting material 18 (800 mg, 1.4 mmol, 1 eq). The solid was dissolved in a solution of DCM and TFA (10 mL, 1:1). The solution was stirred for 45 min at rt. The reaction was partitioned between a solution of 10% sodium carbonate and DCM. The organic was separated and washed with 10% sodium carbonate. The organic phase was concentrated to dryness. The residue was used without further purification for the next step.

Step C

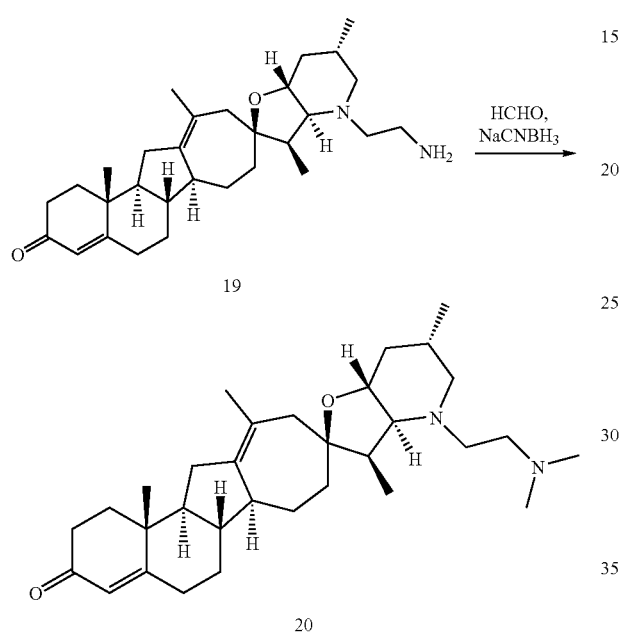

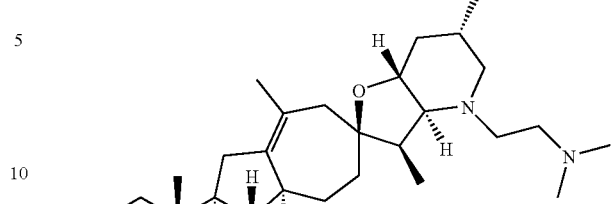

17

A round-bottom flask was charged with starting material 20 (30 mg, 0.06 mmol, 1 eq) and 10% palladium on carbon (30 mg). The solids were suspended in pyridine (2 mL). The suspension was placed under hydrogen atmosphere and the mixture was stirred overnight at rt. The reaction mixture was filtered on Celite® and the filtrate concentrated to dryness. The crude material was purified using silica gel flash chromatography (MeOH/DCM 5:95→10:90) to gave the desired material. ([M+H]=497.7 m/z).

A round-bottom flask was charged with starting material (300 mg, 0.64 mmol, 1 eq) was dissolved in THF/ACN (1:1, 4 mL). The reaction was charged 37% formaldehyde in water (240 µL, 3.22 mmol, 5 eq) and sodium cyanoborohydride (64 mg, 1 mmol, 1.6 eq). The mixture was stirred for 30 min at rt. The reaction was then partitioned between a solution a saturated aqueous solution of sodium bicarbonate and DCM. The organic was separated, dried and concentrated to dryness. The crude material was purified using silica gel flash chromatography (MeOH/DCM 5:95→10:90) to give the desired material.

Example 10

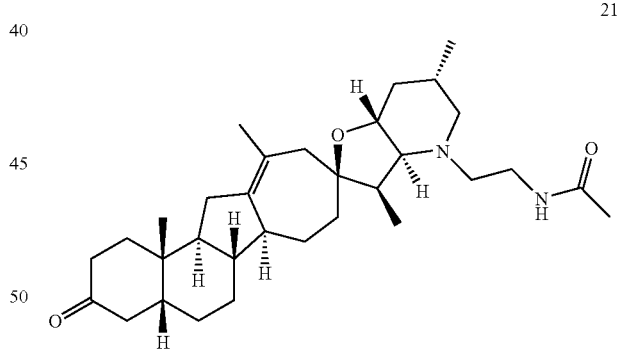

21

Step D

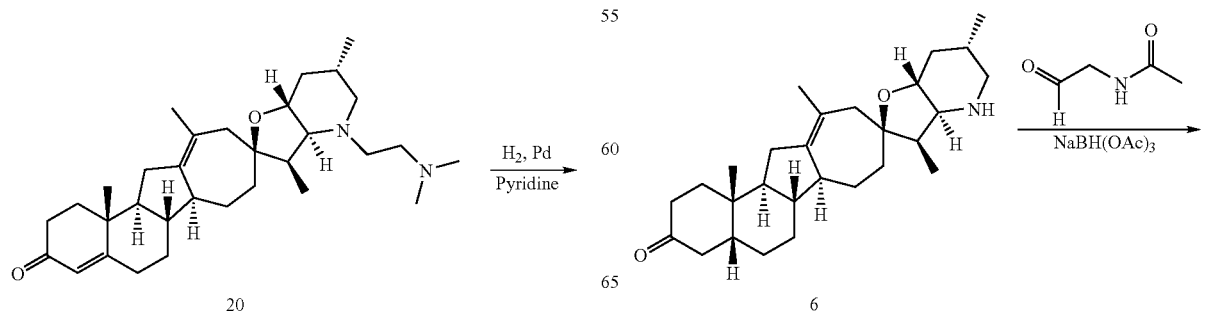

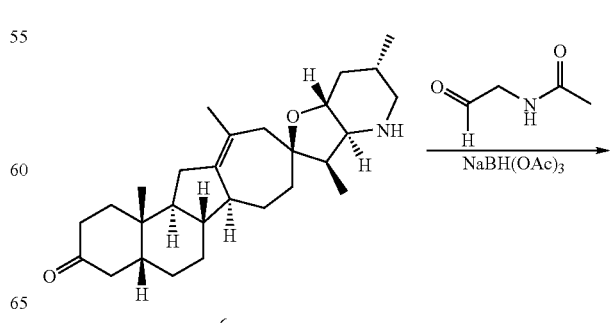

-continued

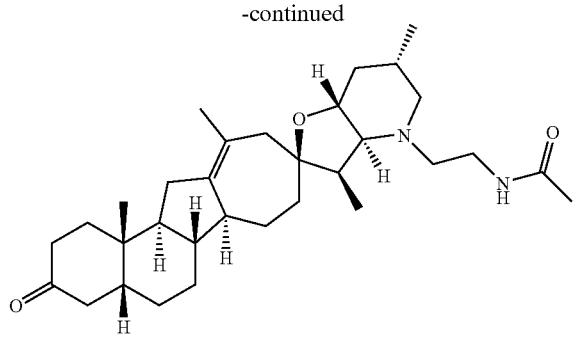

21

A round-bottom flask was charged with starting material (85 mg, 0.20 mmol, 1 eq) was dissolved in DCM (4 mL). The reaction was charged with N-(2-oxoethyl)acetamide (80 mg, 0.70 mmol, 3.5 eq) and sodium triacetoxyborohydride (170 mg, 0.80, 4 eq). The mixture was stirred for 1 hour at rt. The reaction was partitioned between a solution a saturated aqueous solution of sodium bicarbonate and DCM. The organic was separated, dried and concentrated to dryness. The crude material was purified using silica gel flash chromatography (MeOH/DCM 5:95) to give the desired material. ([M+H]= 511.7 m/z).

Example 11

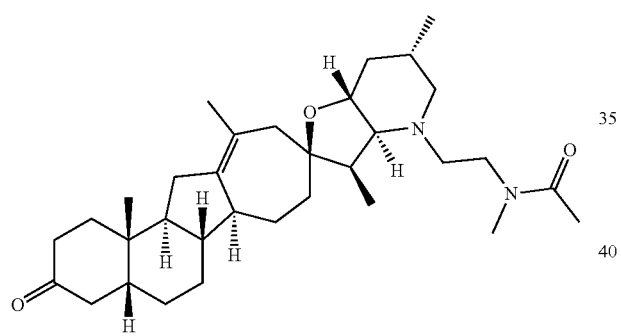

22

Compound 22 was synthesized according to the procedure described in example 9, using N-methyl-N-(2-oxoethyl)acetamide in place of N-(2-oxoethyl)acetamide. ([M+H]=525.7 m/z).

Example 12

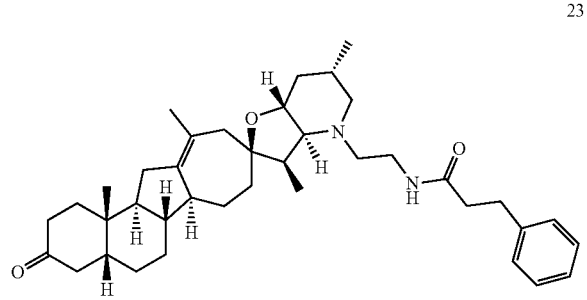

23

Compound 23 was synthesized according to the procedure described in example 10, using N-(2-oxoethyl)-3-phenylpropanamide in place of N-(2-oxoethyl)acetamide. ([M+H]= 601.8 m/z).

Example 13

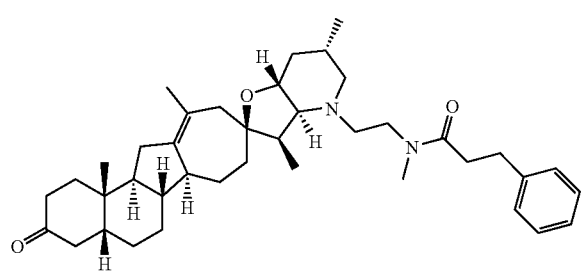

24

Compound 23 was synthesized according to the procedure described in example 10, using N-methyl-N-(2-oxoethyl)-3-phenylpropanamide in place of N-(2-oxoethyl)acetamide. ([M+H] 615.9 m/z)

Example 14

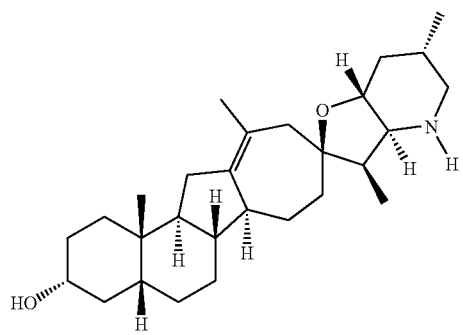

25

Step A

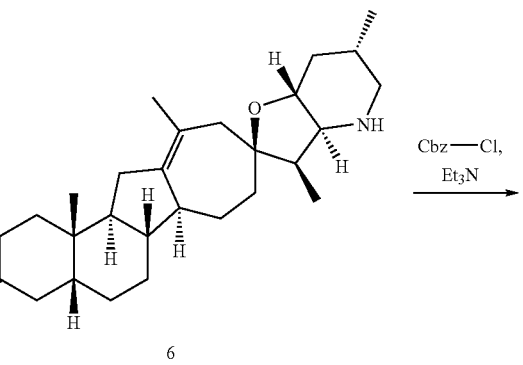

6

-continued

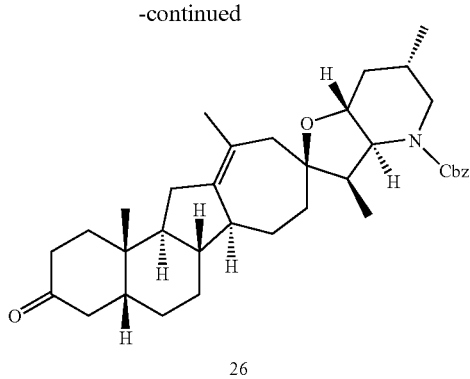

26

A round-bottom flask was charged with compound 6 (4.23 g, 9.94 mmol, 1 eq) and THF (60 mL). Triethylamine (6.92 mL, 49.7 mmol, 5.0 eq) and benzyl chloroformate (1.54 mL, 10.93 mmol, 1.1 eq) were added and the mixture was stirred for 1 hour at rt. The reaction mixture was partitioned between saturated aqueous bicarbonate (100 mL) and EtOAc (100 mL). The phases were separated and the organics were dried (Na₂SO₄) and concentrated to dryness. The crude material was purified using silica gel flash chromatography (EtOAc/Hexanes 2:98→14:86) to give 3.75 g of material.

Step B

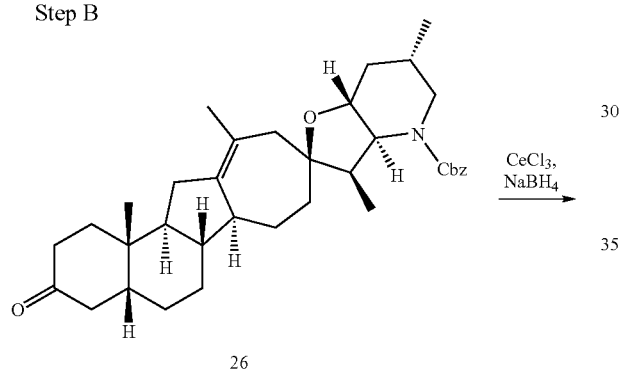

A MeOH solution (10 ml) of cerium trichloride heptahydrate (260 mg, 0.69 mmol, 1.3 eq.) at 0° C. was treated with sodium borohydride (24 mg, 0.65 mmol, 1.2 eq), stirred for 15 min, and then cooled to −78° C. A THF solution (10 ml) of ketone 26 (300 mg, 0.54 mmol, 1 eq) was added, and the mixture was stirred for 1 h and then warmed to rt. Water (50 ml) and EtOAc (50 ml) were added, mixed, and the layers split. The organic layer was collected, washed with brine (30 ml), dried over sodium sulfate, and concentrated to a white residue. The crude product was purified by silica gel flash chromatography (ether/hexanes 2:3→1:1) to give 235 mg of 3-beta alcohol 27.

Step C

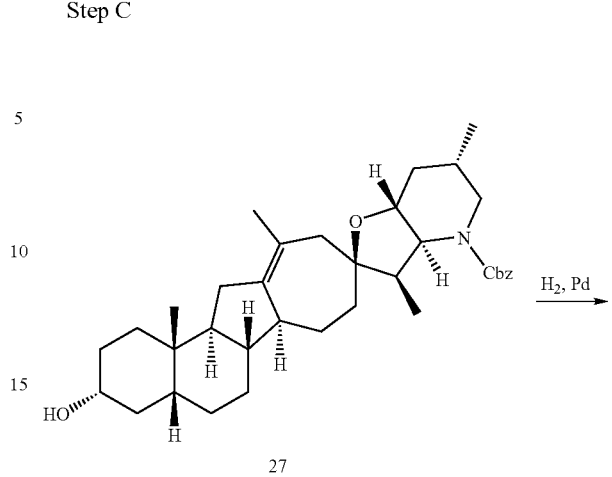

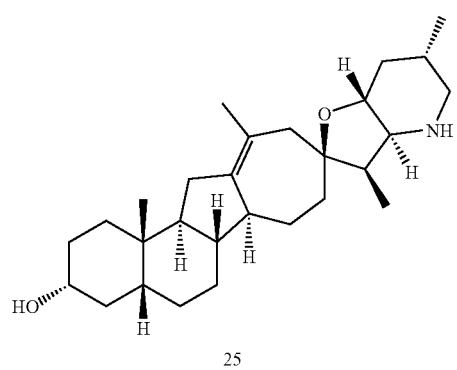

Compound 27 (235 mg, 0.42 mmol, 1 eq) was dissolved in EtOAc (7 ml) in a flask with stir bar and rubber septum. The solution was sparged with nitrogen, and Pd/C 10% (wet, Aldrich Degussa type E101, 50 mg) was added. This mixture was sparged with nitrogen and then hydrogen gas and stirred at rt for 3 h. The mixture was then sparged with nitrogen, filtered through a 0.45 µm polyethylene membrane and concentrated to a clear oil. The oil was purified by silica gel flash chromatography (NH₄OH(aq)/MeOH/DCM 0.5:2:97.5→0.5:6:93.5) to give 130 mg of compound 25 as a white powder. ([M+H]=427.4 m/z)

Example 15

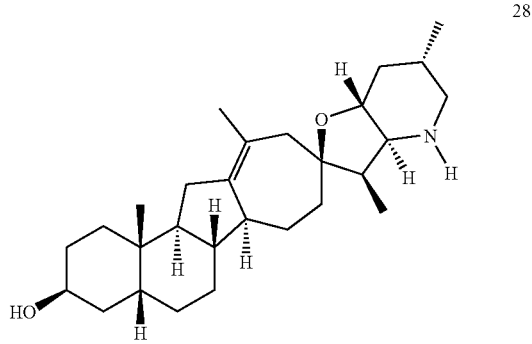

Step A

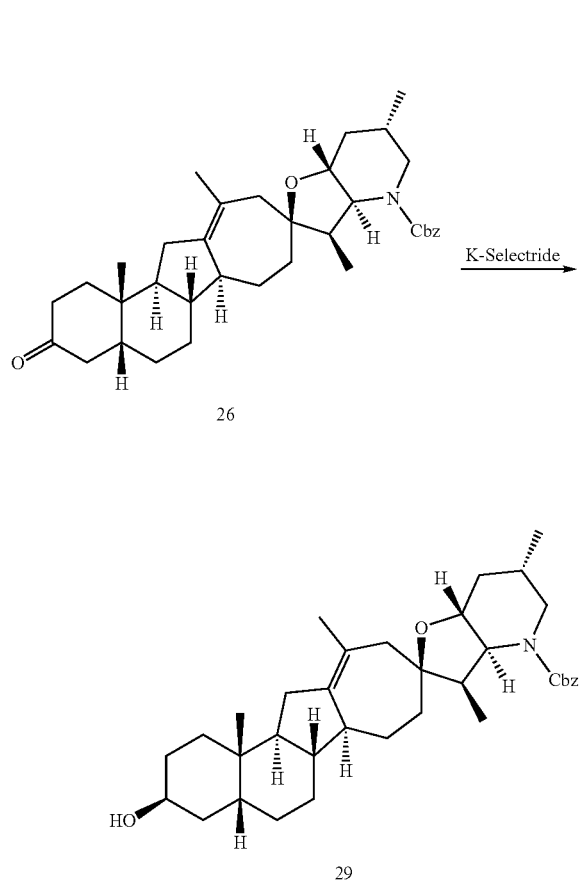

A THF solution (10 ml) of ketone 26 (300 mg, 0.54 mmol, 1 eq) at −78° C. was treated with K-Selectride® (Potassium tri-sec-butylborohydride) (0.58 ml, 0.58 mmol, 1.1 eq) and stirred for 60 min. Methanol (1 ml) was added and the solution warmed to rt. Water (50 ml) and EtOAc (50 ml) were added, mixed, and the layers split. The organic layer was washed with brine (30 ml), dried over sodium sulfate, and concentrated to a white residue. The crude product was purified by silica gel flash chromatography (Ether/Hexanes 2:3→1:14) to give 170 mg of pure 3-alpha alcohol 29.

Step B

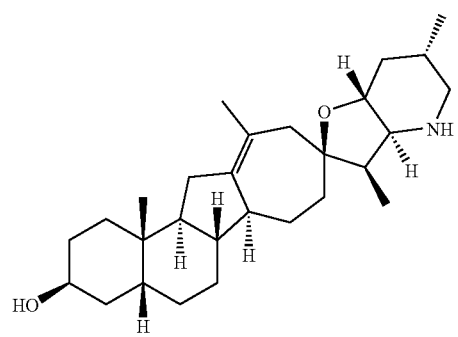

Compound 29 (170 mg, 0.30 mmol, 1 eq) was dissolved in EtOAc (5 ml) in a flask with stir bar and rubber septum. The solution was sparged with nitrogen, and Pd/C 10% (wet, Aldrich Degussa type E101, 35 mg) was added. This mixture was sparged with nitrogen and then hydrogen gas and stirred at rt for 3 h. The mixture was then sparged with nitrogen, filtered through a 0.45 μm polyethylene membrane and concentrated to a clear oil. The oil was purified by silica gel flash chromatography (NH$_4$OH(aq)/MeOH/DCM 0.5:2:97.5→0.5:6:93.5) to afford 76 mg of compound 28 as a white powder ([M+H]=427.4 m/z).

Example 16

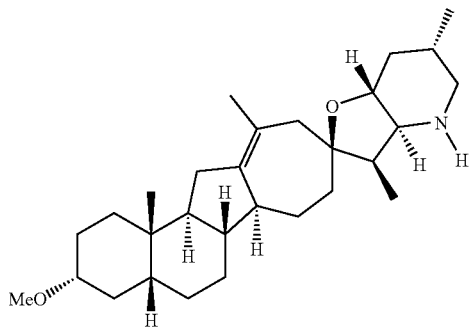

Step A

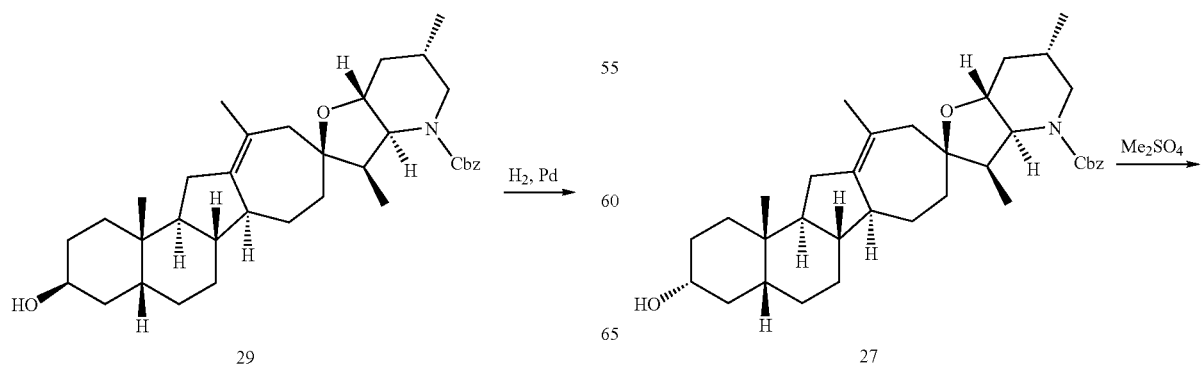

-continued

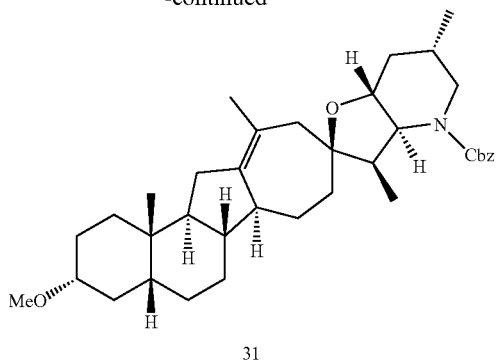

31

Compound 27 (100 mg, 0.18 mmol, 1 eq) with benzyltriethylammonium chloride (8 mg, 0.36 mmol, 0.2 eq) was dissolved in DCM (5 ml) and stirred vigorously with dimethyl sulfate (130 μL, 1.43 mmol, 8 eq) and 50% aqueous potassium hydroxide (0.5 ml) at rt for 18 h. The mixture was partitioned between water (30 ml) and EtOAc (30 ml), and the organic layer was then washed with brine, dried over sodium sulfate, and concentrated to a clear oil. The crude ether was purified by silica gel flash chromatography (Ether/Hexanes 3:7→9:113) to give 75 mg of the methyl ether as a clear oil.

Step B

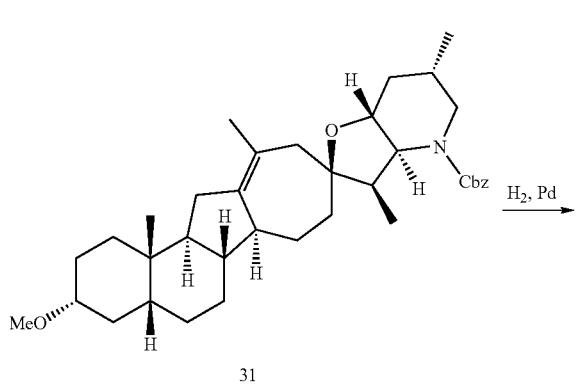

31

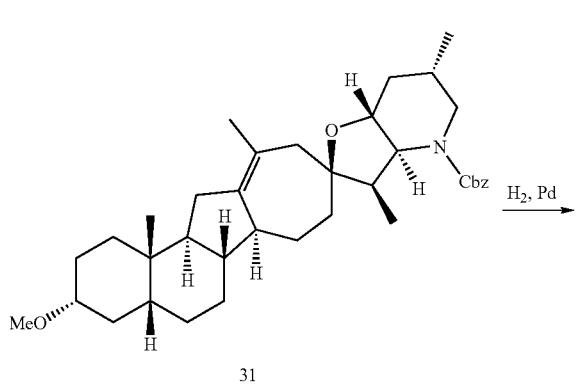

30

Compound 31 (66 mg, 0.115 mmol, 1 eq) was dissolved in EtOAc (5 ml) in a flask with stir bar and rubber septum. The solution was sparged with nitrogen, and Pd/C 10% (wet, Aldrich Degussa type E101, 20 mg) was added. This mixture was sparged with nitrogen and then hydrogen gas and stirred at rt for 3 h. The mixture was then sparged with nitrogen, filtered through a 0.45 μm polyethylene membrane and concentrated to a clear oil. The oil was purified by silica gel flash chromatography (NH₄OH(aq)/MeOH/DCM 0.5:2:97.5→0.5:6:93.5) to give 22 mg of compound 30 as a white powder ([M+H]=441.4 m/z).

Example 17

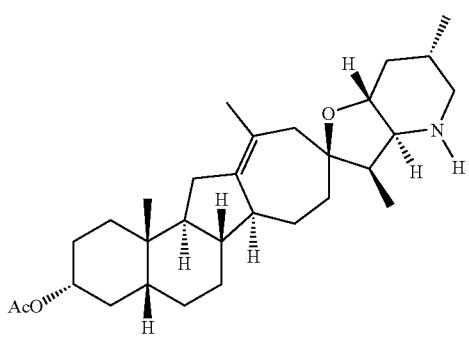

32

Step A

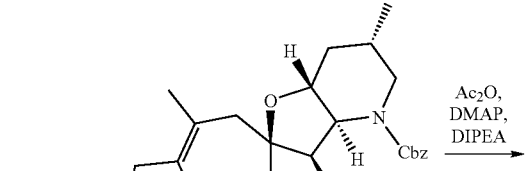

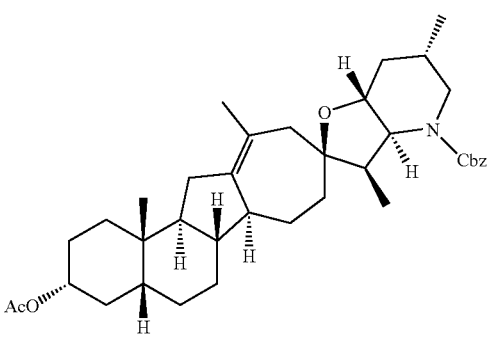

33

Compound 27 (100 mg, 0.18 mmol, 1 eq) was dissolved in DCM (5 ml), and 4-dimethylaminopyridine (4 mg, 0.35 mmol, 0.2 eq), N,N-diisopropylethylamine (0.15 ml, 0.9 mmol, 5 eq), and acetic anhydride (0.070 ml, 0.72 mmol, 4 eq) were added. After stirring for 12 h at rt, the solution was split between EtOAc (30 ml) and 5% aqueous sodium bicarbonate (15 ml). The organic layer was washed with brine, dried over sodium sulfate, and concentrated to a clear oil. The crude ester was purified by silica gel chromatography (Ether/Hexanes 3:7→9:113) to give 100 mg of the ester as a clear oil.

Step B

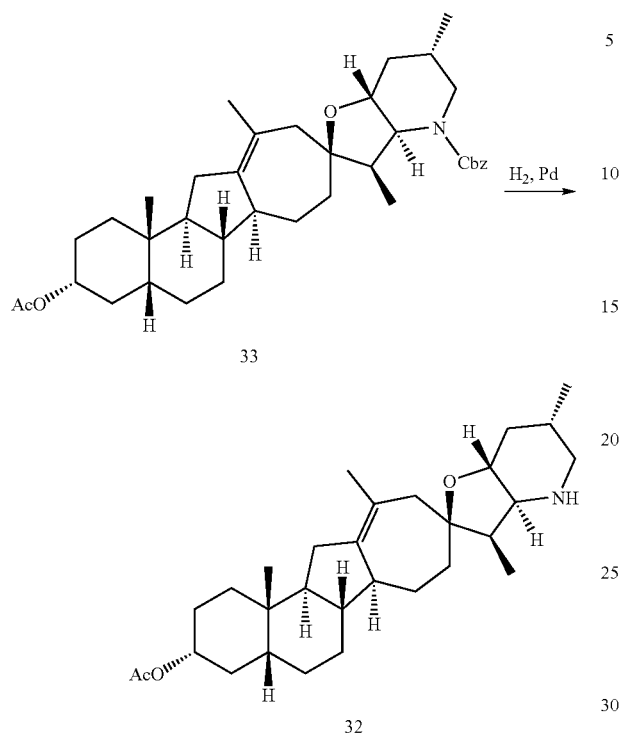

Compound 33 (100 mg, 0.18 mmol, 1 eq) was dissolved in EtOAc (5 ml) in a flask with stir bar and rubber septum. The solution was sparged with nitrogen, and Pd/C 10% (wet, Aldrich Degussa type E101, 20 mg) was added. This mixture was sparged with nitrogen and then hydrogen gas and stirred at rt for 3 h. The mixture was then sparged with nitrogen, filtered through a 0.45 μm polyethylene membrane and concentrated to a clear oil. The oil was purified by silica gel flash chromatography (NH$_4$OH(aq)/MeOH/DCM 0.5:2:97.5→0.5:6:93.5) to give 45 mg of compound 32 as a white powder ([M+H]=469.4 m/z).

Example 18

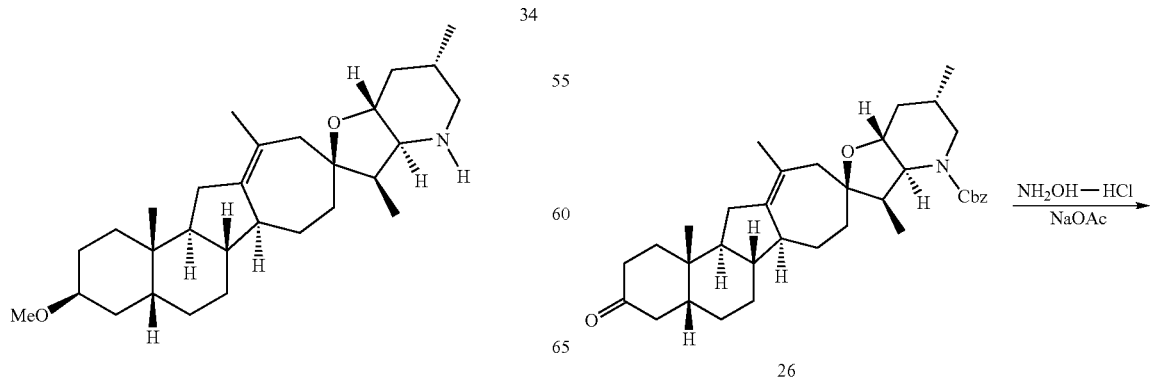

Compound 34 was synthesized according to the procedure described in example 16, using compound 29 in place of compound 27. ([M+H]=441.4 m/z).

Example 19

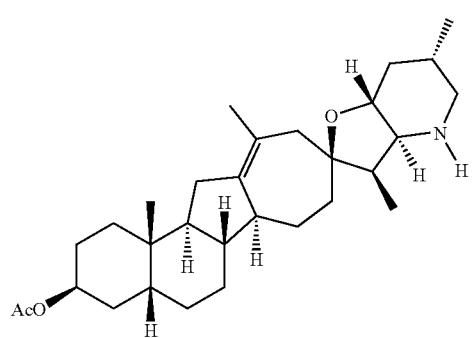

Compound 34 was synthesized according to the procedure described in example 17, using compound 29 in place of compound 27. MS ([M+H]=469.4 m/z)

Example 20

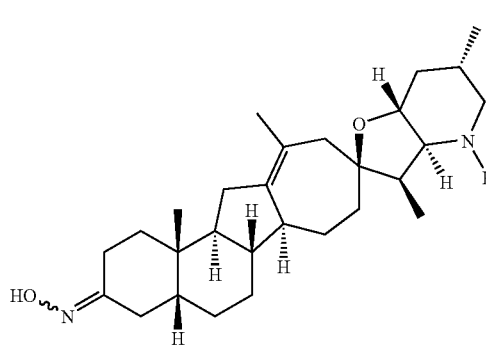

Step A

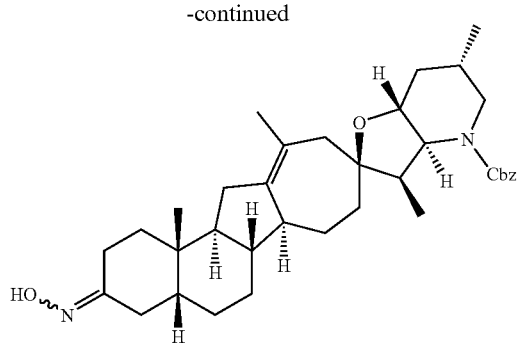

37

An ethanol solution (5 ml) of compound 26 (185 mg, 0.3 mmol, 1 eq) was treated with hydroxylamine hydrochloride (140 mg, 2 mmol, 6 eq), sodium acetate (160 mg, 2 mmol, 6 eq), and water (0.5 mL), and the mixture was stirred at rt for 1 hr. The mixture was split between EtOAc and water (50 mL each). The organic layer was washed with brine (30 mL), dried over sodium sulfate, and concentrated to a white residue. The crude product was purified by silica gel chromatography (ether/hexanes 2:3→1:1) to give 193 mg of oxime 37.

Step B

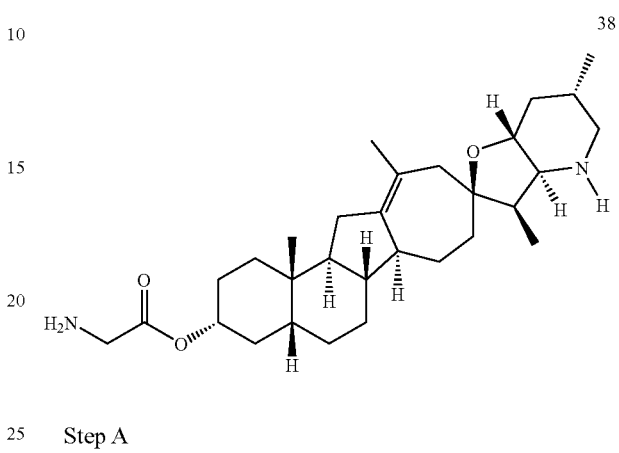

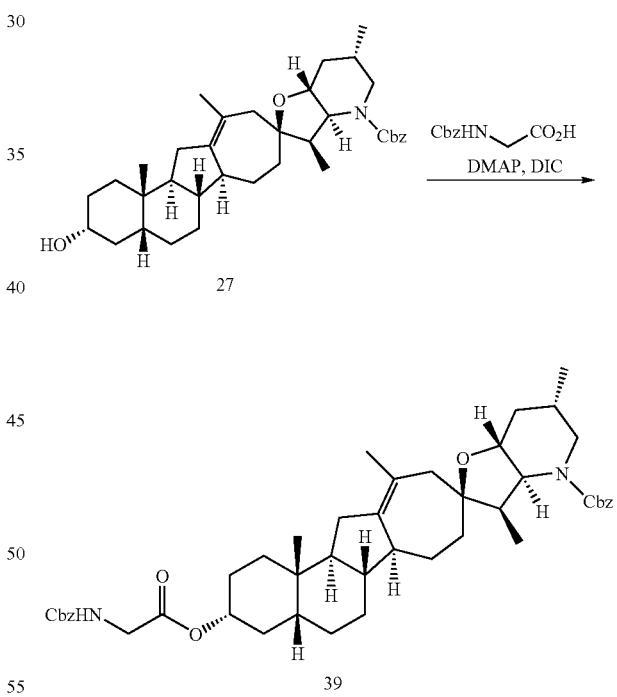

Compound 37 (65 mg, 0.113 mmol) was dissolved in EtOAc (7 ml) in a flask with stir bar and rubber septum. The solution was sparged with nitrogen, and Pd/C 10% (wet, Aldrich Degussa type E101, 20 mg) was added. This mixture was sparged with nitrogen and then hydrogen gas and stirred at rt for 3 h. The mixture was then sparged with nitrogen, filtered through a 0.45 μm polyethylene membrane and concentrated to a clear oil. The oil was purified by silica gel flash chromatography (NH$_4$OH(aq)/MeOH/DCM 0.5:2:97.5→0.5:6:93.5) to give 15 mg of compound 36 as a white powder, a mixture of cis and trans oxime isomers ([M+H]=440.3 m/z).

Example 21

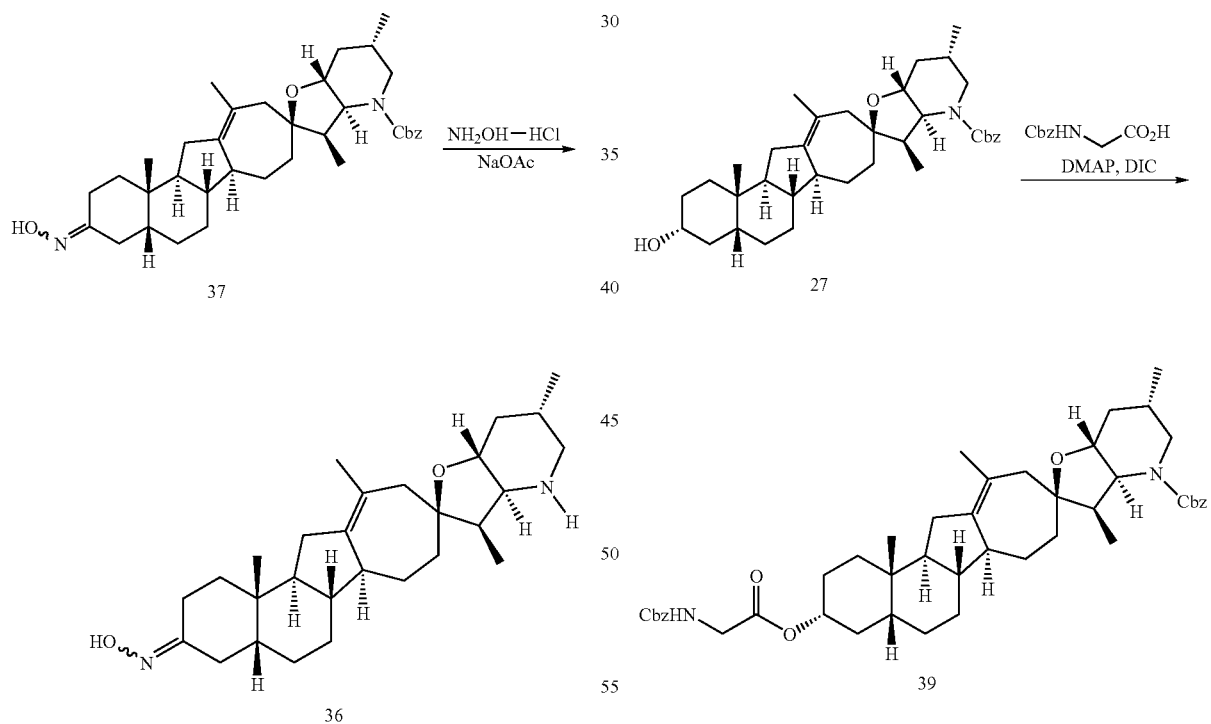

Step A

Compound 27 (42 mg, 0.075 mmol, 1 eq) was dissolved in DCM (5 ml), and 4-dimethylaminopyridine (2 mg, 0.02 mmol, 0.2 eq), N-Cbz glycine (23 mg, 0.110 mmol, 1.5 eq), and diisopropylcarbodiimide (0.023 ml, 0.150 mmol, 2 eq) were added. After stirring for 12 h at rt, the solution was split between EtOAc (30 ml) and 5% aqueous sodium bicarbonate (15 ml). The organic layer was washed with brine, dried over sodium sulfate, and concentrated to a clear oil. The crude ester was purified by silica gel flash chromatography (ether/hexanes 2:3→1:1) to give 35 mg of the ester as a clear oil.

Step B

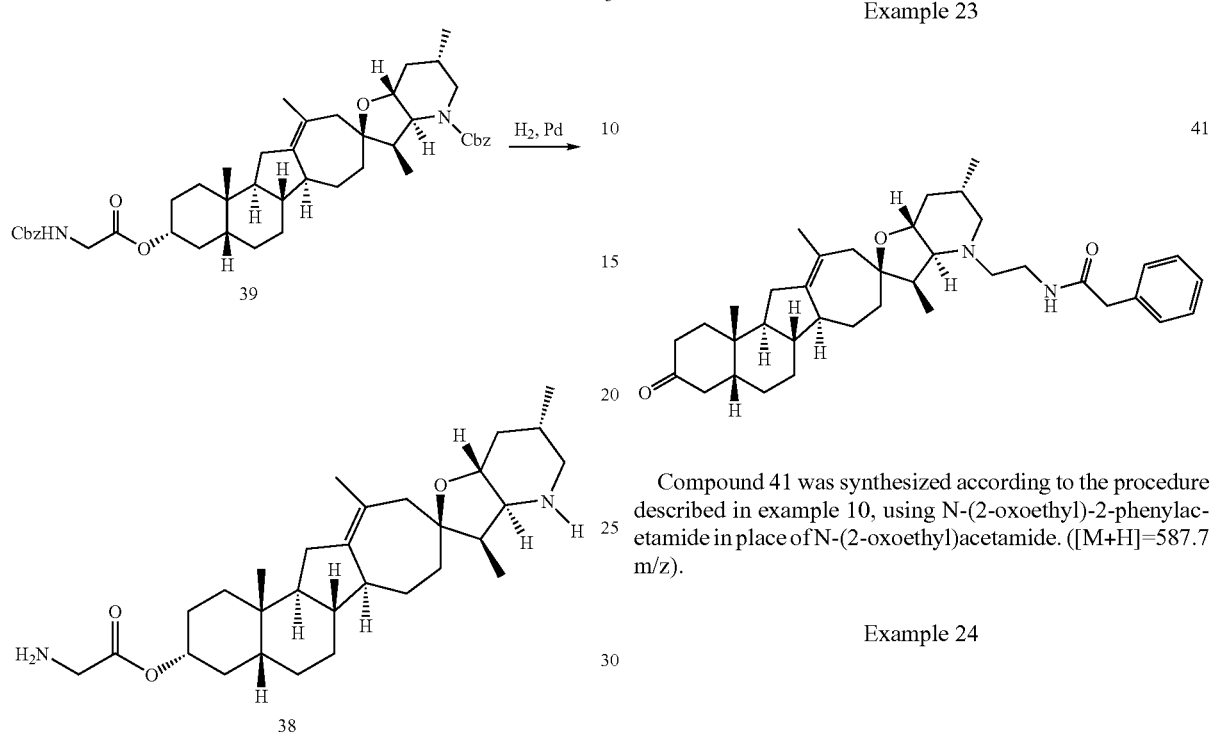

Compound 39 (235 mg, 0.42 mmol, 1 eq) was dissolved in EtOAc (7 mL) in a flask with stir bar and rubber septum. The solution was sparged with nitrogen, and Pd/C 10% (wet, Aldrich Degussa type E101, 50 mg) was added. This mixture was sparged with nitrogen and then hydrogen gas and stirred at rt for 3 h. The mixture was then sparged with nitrogen, filtered through a 0.45 μm polyethylene membrane and concentrated to a clear oil. The oil was purified by silica gel flash chromatography (NH$_4$OH(aq)/MeOH/DCM 0.5:2:97.5→0.5:6:93.5) to give 17 mg of the desire product as a white powder ([M+H]=452.4 m/z).

Example 22

Compound 40 was synthesized according to the procedure described in example 21, using compound 29 in place of compound 27. ([M+H]=452.4 m/z)

Example 23

Compound 41 was synthesized according to the procedure described in example 10, using N-(2-oxoethyl)-2-phenylacetamide in place of N-(2-oxoethyl)acetamide. ([M+H]=587.7 m/z).

Example 24

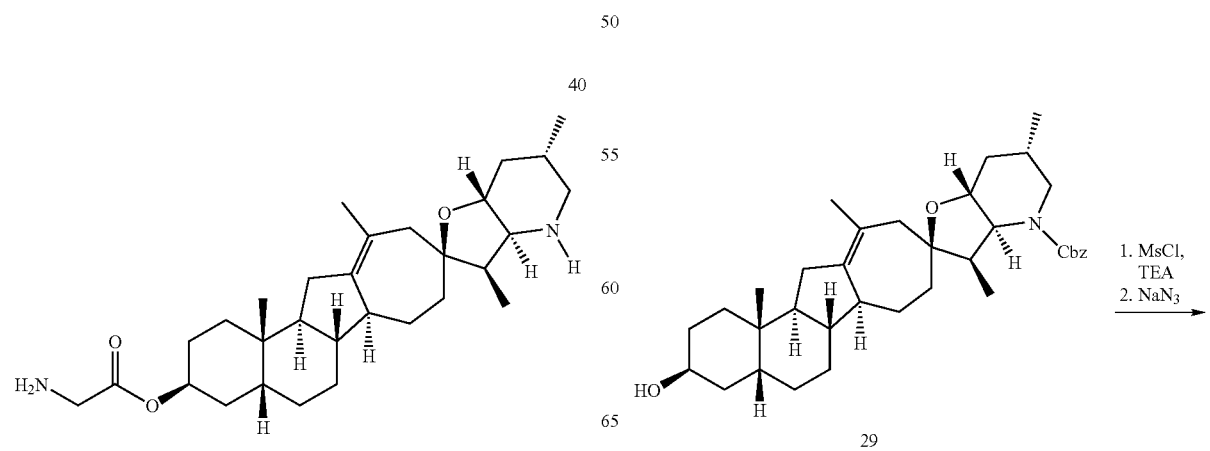

Step A

-continued

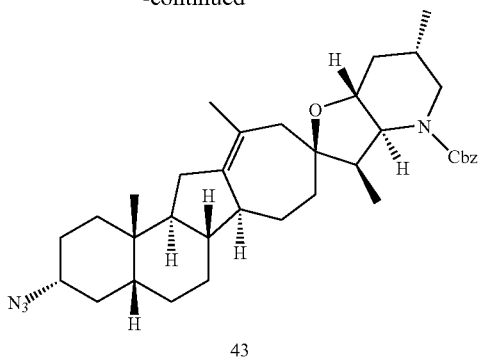

43

A round-bottom flask was charged with alcohol 29 (7.60 g, 13.53 mmol, 1 eq) and was dissolved in DCM (115 mL). The reaction was charged with triethylamine (8.21 g, 81 mmol, 6.0 eq). The mixture was cooled to 0° C. and charged with methanesulfonylchloride (1.86 g, 16.2 mmol, 1.2 eq). After 30 min, the reaction mixture was partitioned between a saturated aqueous solution of sodium bicarbonate and EtOAc. The organic layer was separated, dried over sodium sulfate and concentrated to dryness. The residue was purified using silica gel flash chromatography (EtOAc/hexanes 10→25%) gave the desired material mesylate.

A round-bottom flask was charged with the mesylate (9.1 g, 14.22 mmol, 1 eq) and was dissolved in 50 mL of DMPU. The reaction was charged with sodium azide (4.62 g, 71.1 mmol, 5.0 eq) and heated to 60° C. The mixture was stirred for 17 h. The reaction mixture was then cooled to rt and charged with water. The mixture was stirred for 30 min. The mixture was filtered under vacuum, rinsed with water and air dried and used directly without purification in the next step.

Step B

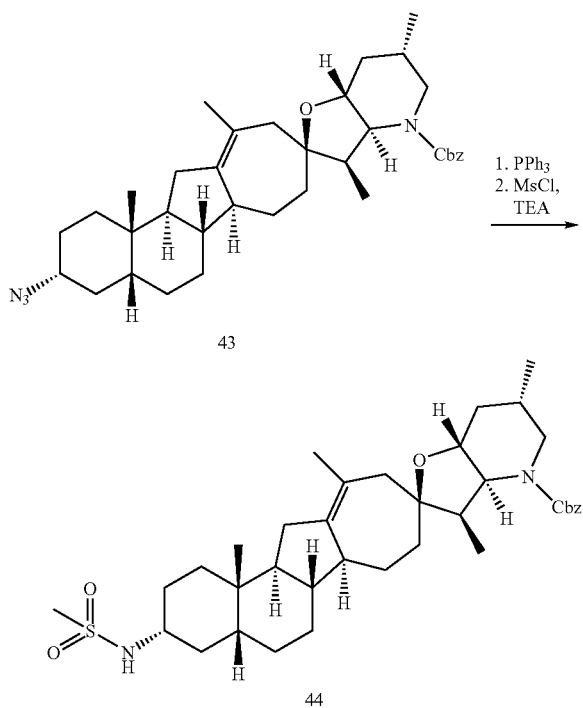

A round-bottom flask was charged with azide 43 (8.35 g, 14.23 mmol, 1 eq) and THF (120 mL) was added. The reaction was then charged with triphenylphosphine (11.2 g, 42.7 mmol, 3.0 eq). The mixture was heated to 50° C. and stirred for 20 h. The reaction mixture was then cooled to rt and the solvent removed under vacuum. The residue purified using silica gel flash chromatography (MeOH/DCM 10% 20%) to afford the amine.

A round-bottom flask was charged with the amine (5.10 g, 9.09 mmol, 1 eq) and was dissolved in DCM (60 mL). The reaction was charged with N,N-diisopropylethylamine (5.88 g, 45.5 mmol, 5.0 eq). The mixture was cooled to 0° C. and charged with methanesulfonylchloride (2.08 g, 18.2 mmol, 2.0 eq). After 30 minutes, the reaction mixture was partitioned between a saturated aqueous solution of sodium bicarbonate and EtOAc. The organic layer was collected, dried over sodium sulfate and concentrated to dryness. The residue was purified using silica gel flash chromatography (EtOAc/hexanes 10→30%) to afford the Cbz protected methanesulfonamide.

Step C

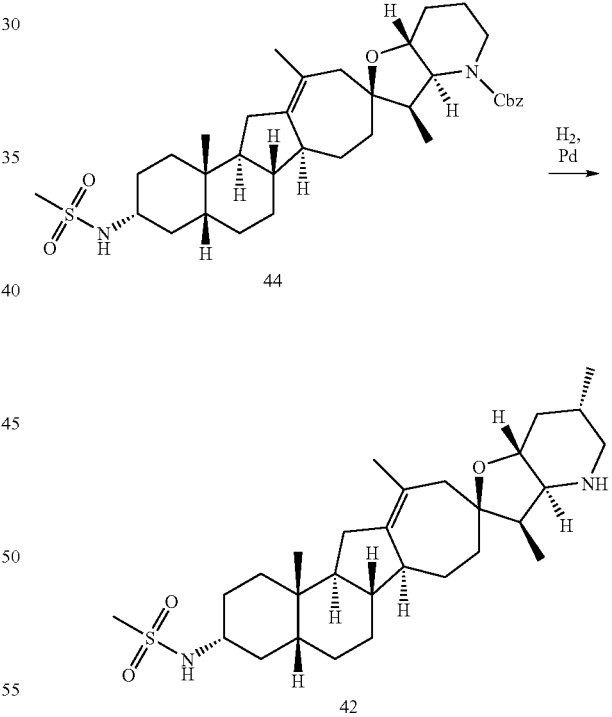

A round-bottom flask was charged with the Cbz protected methanesulfonamide (5.37 g, 8.41 mmol, 1 eq) and 10% palladium on carbon (1.0 g). The solids were suspended in 2-propanol (50 mL). The suspension was placed under hydrogen atmosphere and the mixture was stirred for 4 h at 25° C. The reaction mixture was then filtered on Celite® and the filtrate concentrated to dryness. The residue was then purified using silica gel flash chromatography (DCM/MeOH 0→5%) to afford the desired product. [M+H]=505.6 m/z.

Alternate Synthesis of Compound 42

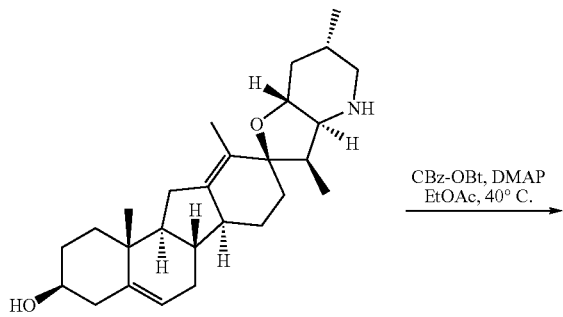

Recrystallized cyclopamine (2.07 g) is charged to an appropriately sized reaction vessel and placed under an inert atmosphere. EtOAc (7.6 g), triethylamine (1.53 g), and DMAP (307 mg) are added sequentially. The suspension is warmed to 40° C. Cbz-OBt is added in three portions over 90 minutes, keeping the internal temperature below 45° C. The reaction mixture is stirred at 40° C. for 90 minutes. The temperature is maintained while methanol (26.4 g) is slowly added to the reaction mixture. The resulting suspension is cooled to room temperature and stirred for at least 15 hours. The crude product is collected by filtration and rinsed with methanol (5 g). The white solid is dried under vacuum to a constant weight and recrystallized from heptane (30.3 g) and toluene (3.2 g) to afford Compound 24a (3.0 g).

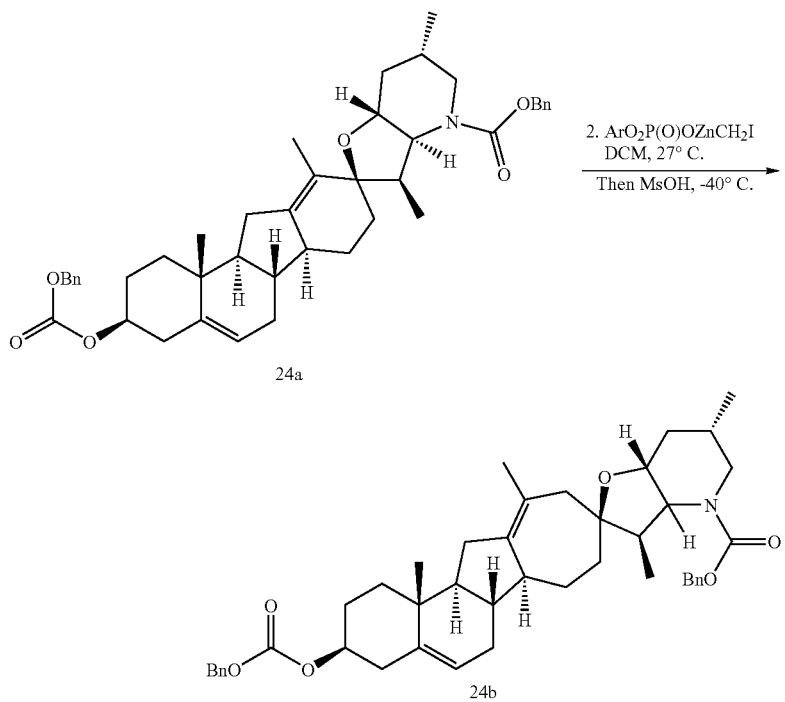

-continued

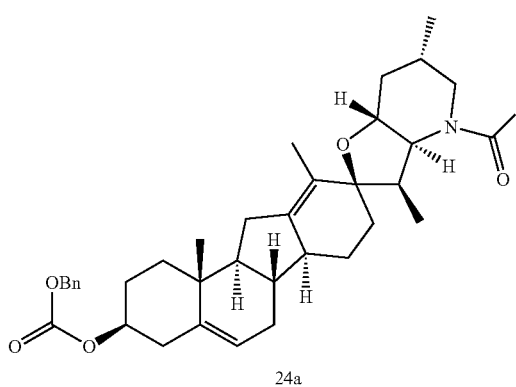

Solid bis(2,6-dimethylphenyl)hydrogenphosphate and 24a are pre-dried and placed under a nitrogen atmosphere. Neat diethyl zinc (722 mg) is charged to an appropriately sized reaction vessel containing DCM (9.0 g). DCM solutions of the phosphate (1.83 g in 17.9 g) and IPI-332690 (1.34 g in 3.6 g) are added sequentially at or below 25° C. Diiodomethane (1.58 g) is charged and the reaction is stirred at 28° C. for 4-6 hours. The reaction is cooled to −45° C. and a solution of methanesulfonic acid in DCM (566 mg in 1.5 g) is charged. After 15 minutes, morpholine (1.711 g) is added and the mixture is allowed to warm to room temperature overnight. The organic layer is washed twice with 2N HCl (2×13.6 g) then sequentially with 4.8 wt % sodium carbonate (aq), 4.8 wt % sodium sulfite (aq), and 4.8 wt % brine (13.6 g each). The organic layer is dried, filtered, concentrated to 4 g and diluted with isopropanol (4 g). The product is crystallized from solution by the slow addition of methanol (9.3 g). Filtration with a methanol rinse (2.6 g) and drying afford 1.09 g of 24b (79% isolated yield).

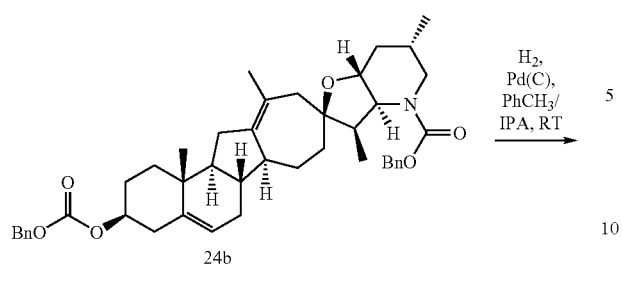

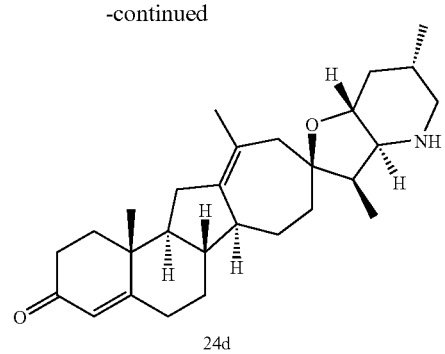

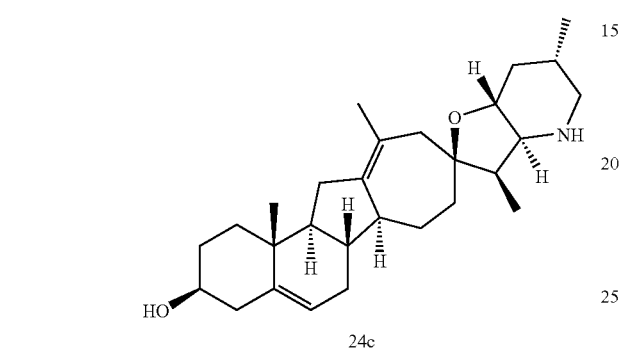

Johnson Matthey Pd/C catalyst A-305038-5 (890 mg) is charged to an appropriately sized reaction vessel, followed by 24b (2.24 g). The reaction vessel is purged with N$_2$ and toluene (21.8 g) and 2-propanol (6.7 g) are added sequentially. The system is degassed and placed under a nitrogen atmosphere, and the process is repeated with hydrogen. The system is stirred vigorously and the hydrogen blanket is maintained at one atmosphere for 4-5 hours. The reaction is monitor by either TLC or HPLC. If incomplete, the reaction is inerted, additional catalyst (145 mg) is charged, and the hydrogen atmosphere is returned for another hour. Ethylenediamine (12.9 mg) is charged and the mixture was stirred for 15 minutes. The catalyst is removed by filtration with a toluene:IPA (3:1) rinse. The filtrate and rinses are concentrated and solvent exchanged to toluene. The product is crystallized from toluene (19.0 g) and heptane (18.0 g) to afford 24c as a white crystalline solid (1.34 g, 98% yield).

24c (644 mg) is charged to an appropriately sized reaction vessel followed by aluminum t-butoxide (525 mg), toluene (8.34 g, 15 vol), and 2-butanone (7.83 g, 15 vol). The contents of the flask are degassed with evacuation/nitrogen purge cycles to remove oxygen and the reaction mixture is heated at 75° C. with vigorous stirring for 16-18 hours. The reaction is quenched by the addition of aqueous Rochelle's salt (2.6 g in 10.3 g water) and the mixture vigorously stirred for one hour at 45° C. The aqueous and organic layers are separated. The aqueous layer is back extracted with a mixture of toluene (2.9 g) and EtOAc (2.9 g). The organic layers are combined and washed with fresh Rochelle's salt solution (2.6 g in 10.3 g water) and then with water (12.9 g). The resulting organic layer is dried over sodium sulfate (1.97 g), filtered, and concentrated in vacuo. The product is crystallized via a charge and concentration solvent exchange first to IPA (6.5 g) and then Heptane (7.7 g). The thick heptane slurry (~2.7 g) is stirred overnight and solids are collected by filtration. Vacuum drying affords 24d (550 mg) in an 85% yield.

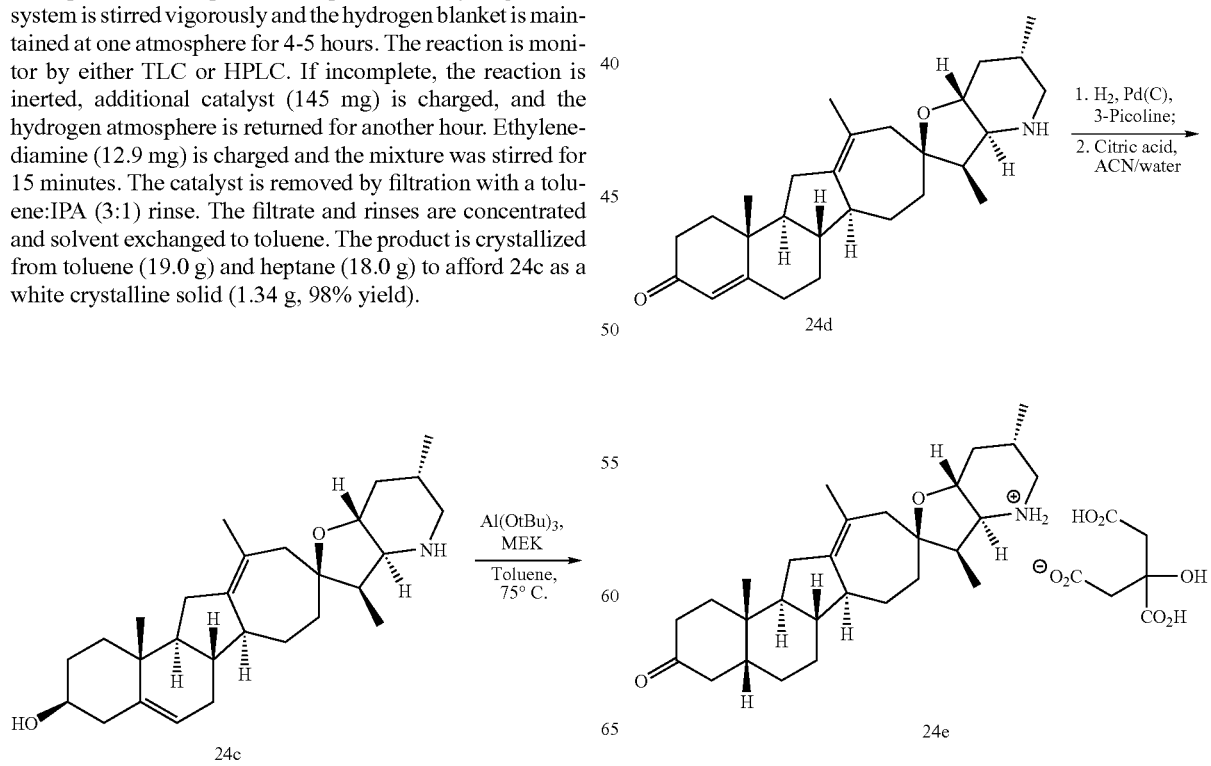

The enone 24d (459 mg) and Johnson-Matthey 5% palladium on carbon (A503023-5, 101 mg) are charged to an appropriately sized multi neck reaction vessel. The vessel is purged with nitrogen and 3-picoline (2.2 g) is charged as the solvent. Stirring is started and the vessel is first degassed using nitrogen and then stirred under hydrogen at atmospheric pressure for 8 hours. At the end of the reaction, the catalyst is removed by filtration through 0.2 micron media, rinsing with ACN (1.4 ml). The filtrate and rinse are combined in a clean reaction vessel equipped with mechanical stiffing, an internal temperature probe, and a nitrogen atmosphere. A solution of citric acid (3.7 g) in water (9.2 ml) is charged to the reaction vessel at or below 30° C., and IPI-335589 is allowed to slowly crystallize from solution as the citrate salt at 20 and then 0° C. The crystalline product is recovered by suction filtration and washed with water (3.7 ml). After drying, the citrate salt, 24e, is isolated as a hydrate (3-5 wt % water) in 89.5% yield (622 mg) with a β:α ratio approaching 90:1.

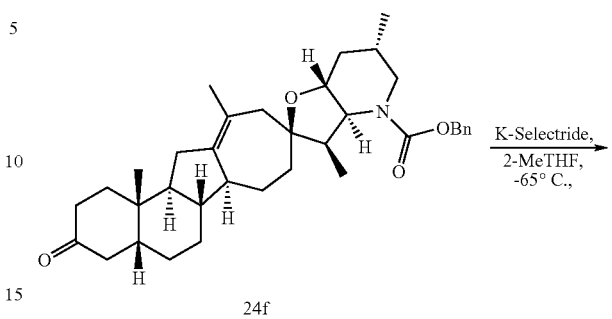

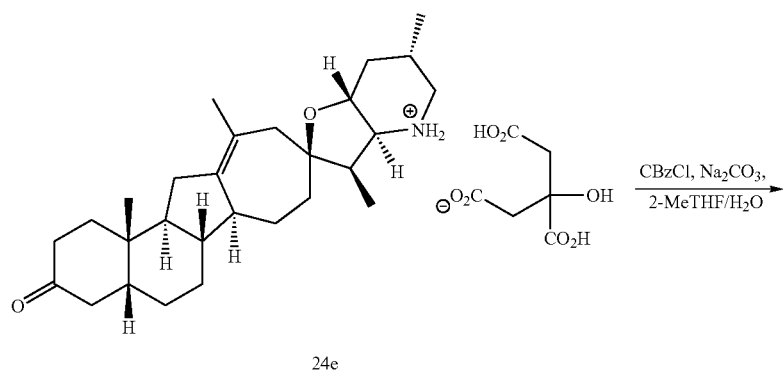

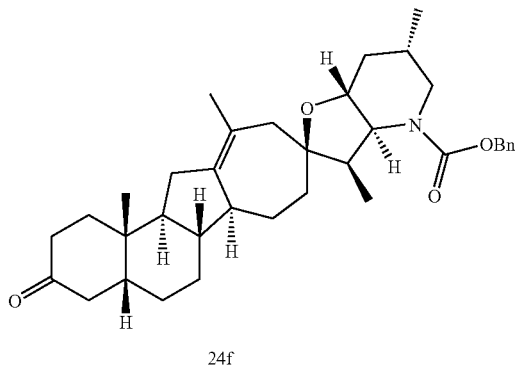

24e (1.50 g) is charged to the appropriately sized reactor along with 2-methyltetrahydrofuran (7.7 g) and 1M sodium carbonate (9.0 ml). A solution of benzyl chloroformate (454 mg) in 2-methyltetrahydrofuran (300 mg) is added via addition funnel and the reaction is ambient temperature for 1-2 hours. When the reaction is complete, the stiffing is stopped, the layers are separated and the organic layer is washed twice with water (2×6 g). The organic layer is dried over of sodium sulfate (3 g), filtered and concentrated. Residual water is reduced further by concentration from fresh 2-methyltetrahydrofuran (6.5 g) and the material is transferred as solution in anhydrous 2-methyltetrahydrofuran to the next reaction.

-continued

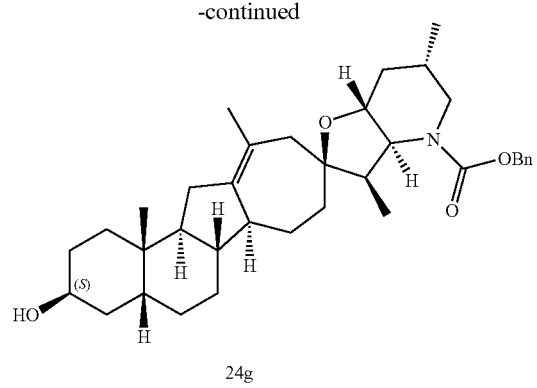

Commercial 1 M K-Selectride in THF (1.20 g) is charged to a dry reaction vessel under a nitrogen atmosphere, diluted with anhydrous 2-methyltetrahydrofuran (2.10 g) and cooled to −65° C. The solution of 24f (0.41 g) in 2-methyltetrahydrofuran (1.5 g), is then slowly added to the reaction vessel to control the internal temperature at −65±5° C. The reaction is stirred for 2 hours and warmed to −20° C. over approximately 1 hour and stirred for an additional hour. The reaction is monitored by HPLC and reactions that are incomplete are driven to completion with additional K-selectride. The reaction is quenched at low temperature with MeOH (0.33 g), then 3M NaOH (2.4 g) at −20° C. and 15% hydrogen peroxide in water (1.04 g) at or below 5° C., then stiffing overnight at ambient temperatures. The layers are split and the organic layer is washed sequentially with 1M aqueous NaOH (2 ml), 0.5 M aqueous Na₂SO₃ (2 ml), and water (2 ml) adjusted to a pH of 3 with HCl. The organic layer is dried over sodium sulfate (0.82 g), filtered and concentrated. The product 24 g (0.457 g) is re-concentrated from DCM (0.9 g) and used in the next reaction.

2.5 wt % sodium bicarbonate (13.8 g) and then water (10.9 g). The organic layer is dried over of sodium sulfate (4 g), filtered, and concentrated. The product solution is solvent exchanged via charge and concentration to t-butyl methyl ether (10.9 ml) and then 1,3-dimethyl-3,4,5,6-tetrahydro-2 (1H)-pyrimidinone (DMPU, 4.7 ml). The DMPU solution is used directly in the next reaction.

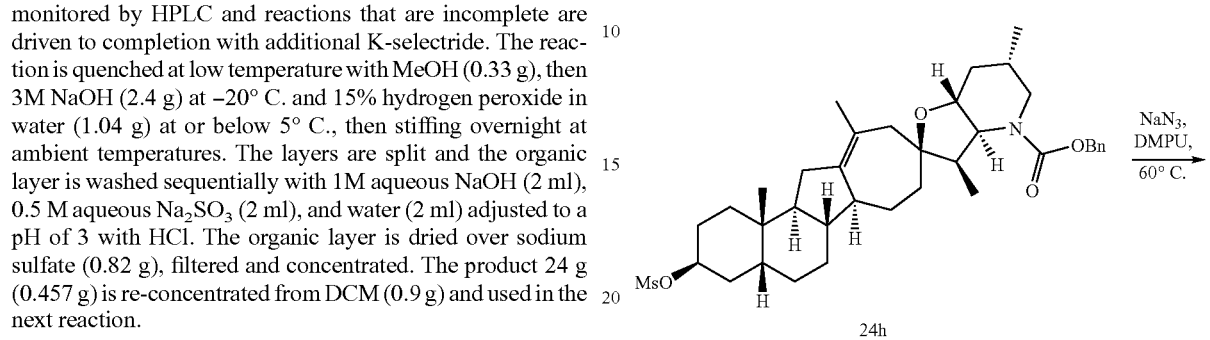

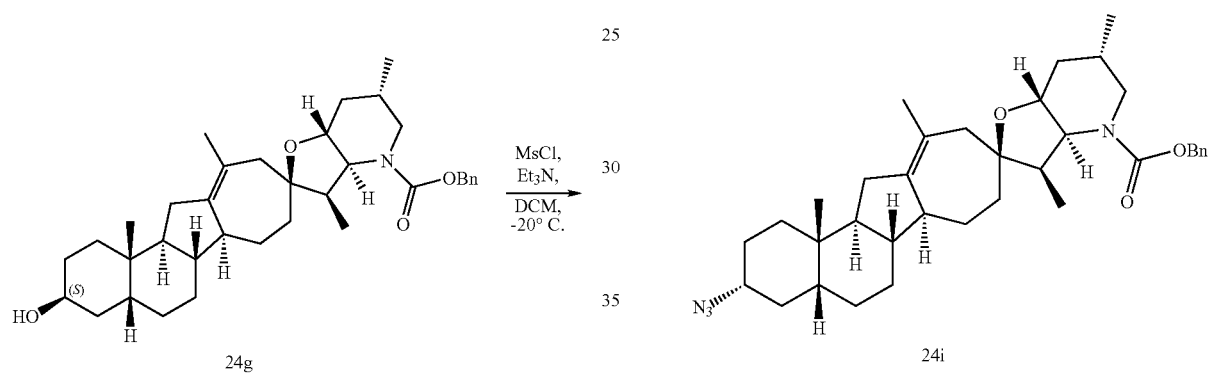

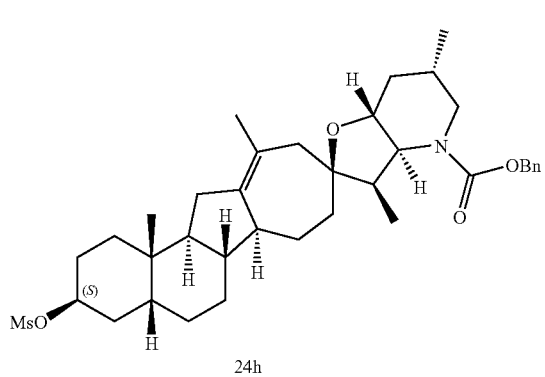

24 g (1.36 g) is charged with anhydrous DCM (18.1 g) to an appropriately size reaction vessel, place under an inert atmosphere and cooled to −20° C. Triethylamine (0.61 mg) is charged followed by the slow addition of methanesulfonyl chloride (373 mg) in anhydrous DCM (300 mg). The reaction is stirred for 1 hour at −20° C. The reaction is monitored by HPLC. Incomplete reactions are driven to completion with additional methanesulfonyl chloride. When complete, the reaction is quenched with water (13.6 g) and allowed to warm. The layers are separated and the organic layer is washed with Sodium azide (0.74 g) is charged to an appropriately sized reaction vessel. The solution of 24 h (1.46 g) in DMPU (5.9 g) is charged to the reaction vessel, rinsing with additional DMPU (1.9 g). The suspension is heated to 60° C. for 15 hours, maintaining a nitrogen sweep for the entire reaction. The reaction is cooled to ambient temperature and diluted with MTBE (11.7 g). The organic solution is washed 3 times with 2% saline (3×8 g), dried over sodium sulfate (4.4 g), filtered, and concentrated. The product is concentrated from THF (6.4 g) and used directly in the next reaction.

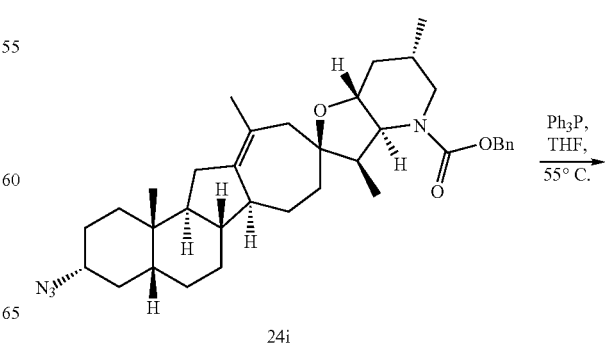

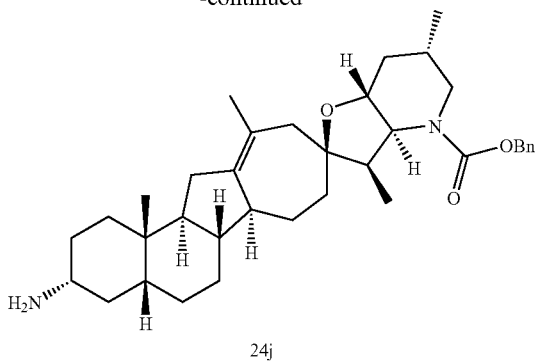

24j

The crude 24i (1.34 g) is dissolved and transferred to a suitably sized reaction vessel with THF (12.6 g). Triphenylphosphine (0.70 g) and water (0.44 g) are charged and the reaction is heated to 55° C. for 15-24 hours. When complete, the reaction is cooled to ambient temperature, dried with magnesium sulfate (1.4 g), filtered and concentrated. The solids are dissolved and concentrated from three portions of DCM (3×9 g) and purified by silica gel chromatography using DCM/MeOH/Et$_3$N gradients to remove reagent based impurities. The pooled fractions are concentrated to dryness, dissolved in DCM (6.8 g) and concentrated to dryness again to afford an amorphous solid (1.12 g) which is used in the next reaction.

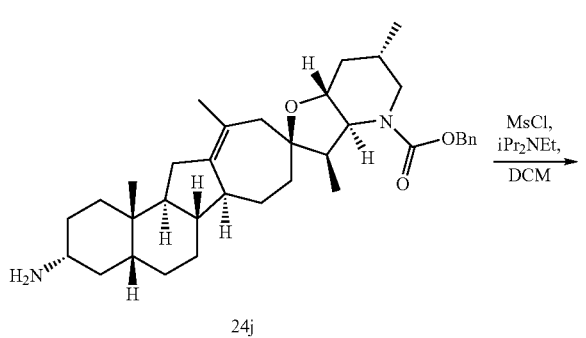

24j

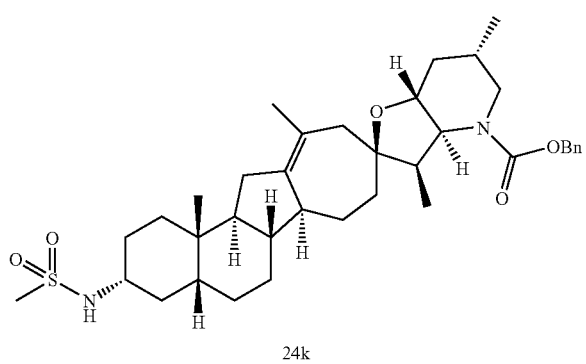

24k 24j (1.09 g) is dissolved and transferred to an appropriately sized reaction vessel with anhydrous DCM (15.8 g) and placed under a nitrogen atmosphere. The solution is cooled to 0° C. N,N-diisopropylethylamine (357 mg) and neat methanesulfonyl chloride (0.165 ml) are charged sequentially while maintaining temperature between below 5° C. The reaction is monitored by HPLC. Incomplete reactions are driven to completion with additional methanesulfonyl chloride. The reaction is quenched with 0.4 M aqueous sodium bicarbonate (11.4 g) and warmed to ambient temperature. The layers are separated and the aqueous phase is back extracted with DCM (5.8 g). The combined organic layers are dried over magnesium sulfate (0.55 g), filtered and concentrated. The product 24k is dissolved and striped from 2-propanol (4.0 g) to remove residual DCM and used directly in the next reaction.

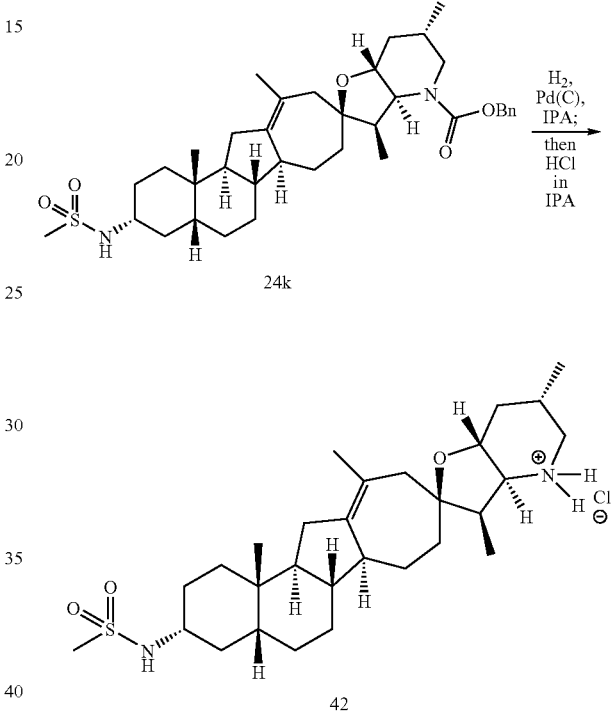

42

Aldrich Degussa type E101 NE/W 10% Pd/C (249 mg) is charged to an appropriately sized reaction vessel and placed under a nitrogen atmosphere. A 2-propanol (9.8 g) solution of 24k (1.24 g) is charged to the reaction vessel. The system is degassed and placed under a nitrogen atmosphere, and the process is repeated with hydrogen. The reaction is stirred under a 1 atm of hydrogen at ambient temperature for 8 hours. An inert atmosphere is returned to the vessel and a second charge of catalyst (125 mg) slurried in 2-propanol (0.5 g) is added to the reaction. The reaction mixture is degassed and placed under a nitrogen atmosphere, and the process is repeated with hydrogen. The reaction is stirred under 1 atm of hydrogen for another 15 hours at ambient temperature. The reaction is monitored by HPLC. Incomplete reactions are treated with additional catalyst and hydrogen. When complete, the reaction is filtered, treated with steam activated carbon (200 mg), and filtered again. The solution is dried by partial concentration transferred to a reaction vessel and diluted with anhydrous 2-propanol to 0.09 M based on the theoretical yield. A 1.25 M HCl solution in 2-propanol (1.64 g) is charged over 20 minutes. The hydrochloride salt crystallizes slowly with gentle stirring and is isolated by filtration. The crystals are washed with 2-propanol (2.5 g) and vacuum dried to afford Compound 42 (916 mg, 80% yield) as a 1:1 IPA solvate.

Example 25

Step A

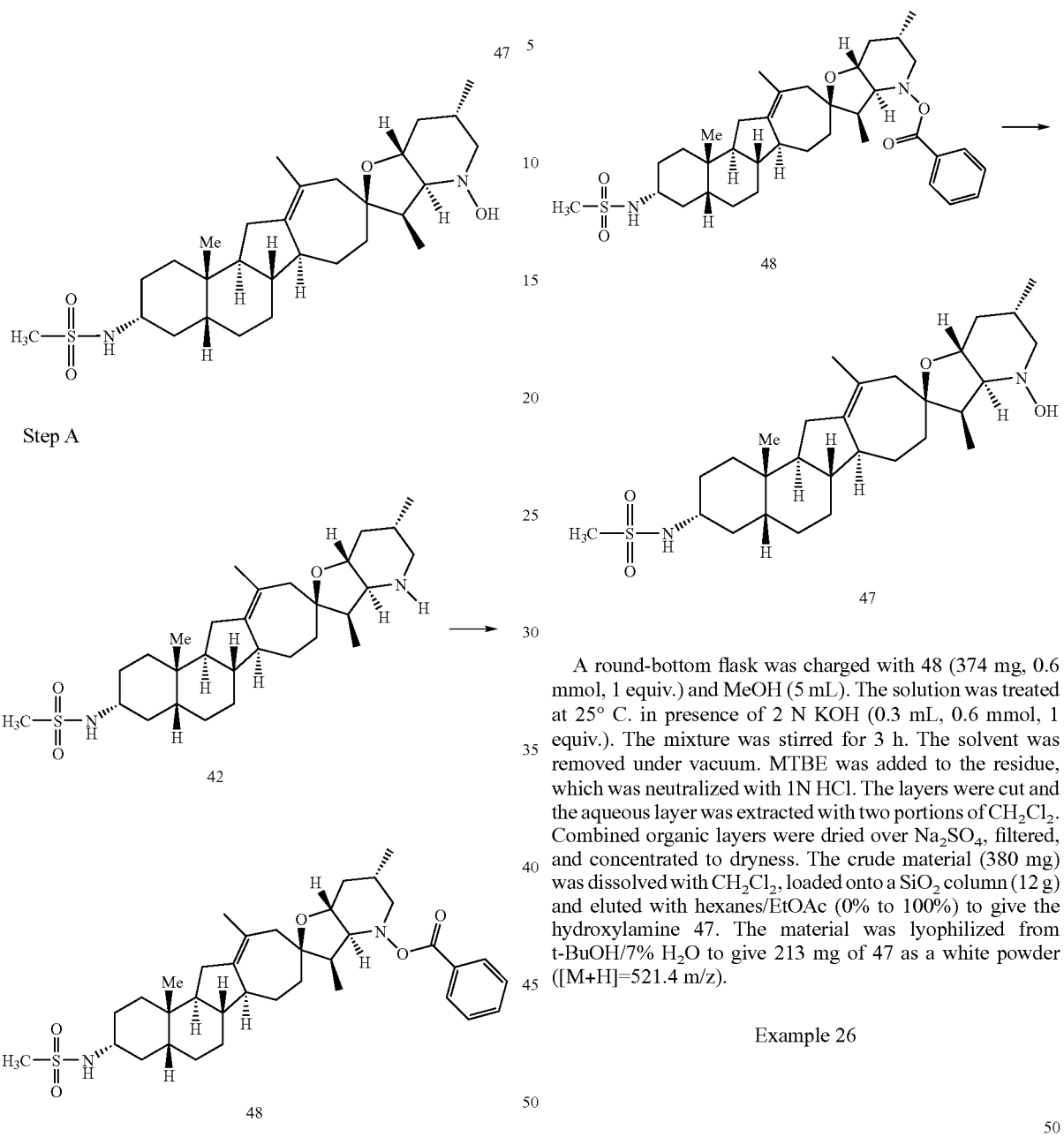

A round-bottom flask was charged with the amine 42 (1.1 g, 2.1 mmol, 1 equiv.), dry tetrahydrofuran (10 ml) and pyridine (880 uL, 10.9 mmol, 5 equiv.). The cooled (0° C.) mixture was treated with benzoylperoxide (1.6 g, 6.5 mmol, 3 equiv.). The mixture was stirred for 2 hours at 0° C. then overnight at 25° C. Reaction mixture diluted with MTBE and washed with a mixture of saturated aqueous NaHCO$_3$ with 1 N NaOH until the layer split. The organic layer was collected and the aqueous was re-extracted once with MTBE. Combined organic layers were washed with brine, dry over Na$_2$SO$_4$, filtered and concentrated to dryness. The crude oil was dissolved in 5 mL of CH$_2$Cl$_2$, loaded onto SiO$_2$ (40 g) column and eluted from hexanes/EtOAc (10% to 50%) to give the benzoyl derivative 48 (380 mg) ([M+H]=625.4 m/z).

Step B

A round-bottom flask was charged with 48 (374 mg, 0.6 mmol, 1 equiv.) and MeOH (5 mL). The solution was treated at 25° C. in presence of 2 N KOH (0.3 mL, 0.6 mmol, 1 equiv.). The mixture was stirred for 3 h. The solvent was removed under vacuum. MTBE was added to the residue, which was neutralized with 1N HCl. The layers were cut and the aqueous layer was extracted with two portions of CH$_2$Cl$_2$. Combined organic layers were dried over Na$_2$SO$_4$, filtered, and concentrated to dryness. The crude material (380 mg) was dissolved with CH$_2$Cl$_2$, loaded onto a SiO$_2$ column (12 g) and eluted with hexanes/EtOAc (0% to 100%) to give the hydroxylamine 47. The material was lyophilized from t-BuOH/7% H$_2$O to give 213 mg of 47 as a white powder ([M+H]=521.4 m/z).

Example 26

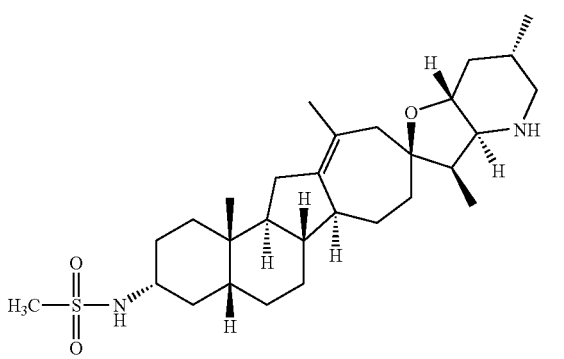

Step A

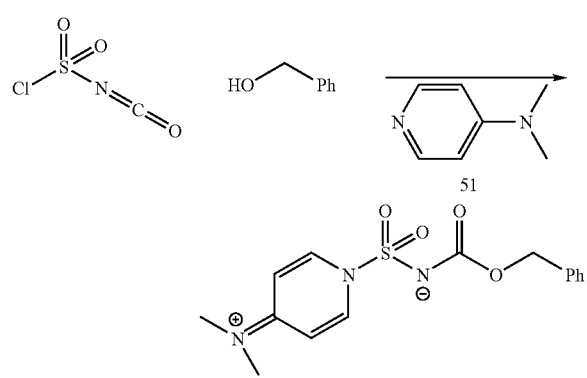

A heat-gun dried flask was charged with dry $CH_2Cl_2$ (5 mL) and benzyl alcohol (785 uL, 7.58 mmol, 1.3 equiv.). The cooled (0° C.) solution was treated with chlorosulfonyl isocyanate (506 uL, 5.83 mmol, 1 equiv.). Then, DMAP (1.4 g, 11.6 mmol, 2 equiv.) was added and the mixture was stirred for 1 h at 25° C. After complete dissolution of DMAP, the reaction was clear for a short period. Then, a white fluffy precipitate formed. The mixture was diluted with $CH_2Cl_2$ (30 mL) and washed with three portions (30 mL each) of water. The organic layer was dried over $Na_2SO_4$, filtered, and evaporated to dryness. The desired white solid 51 was taken to the next step without purification.

Step B

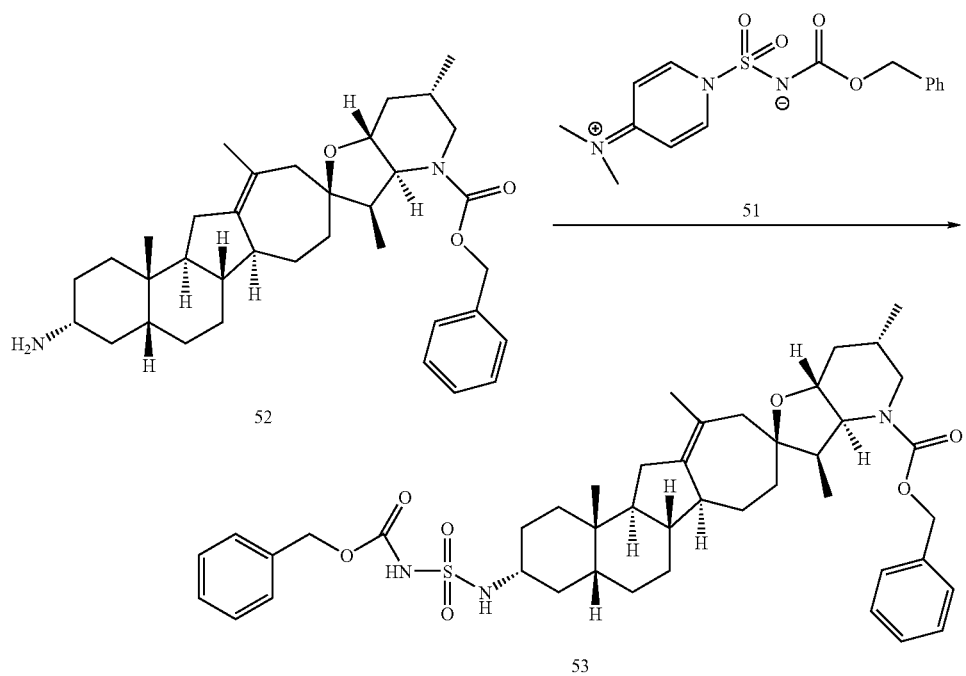

A round-bottom flask was charged with 52 (30 mg, 0.053 mmol, 1 equiv.) and 51 (18 mg, 0.053 mmol, 1 equiv.). Both reagents were dissolved in $CH_2Cl_2$ (2 mL) and the solution was stirred at 25° C. The crude material was loaded onto a $SiO_2$ column (4 g) and eluted with hexanes/EtOAc (0% to 50%) to give 16 mg of the sulfamoylated derivative 53 ([M+Na]=796.4 m/z).

Step C

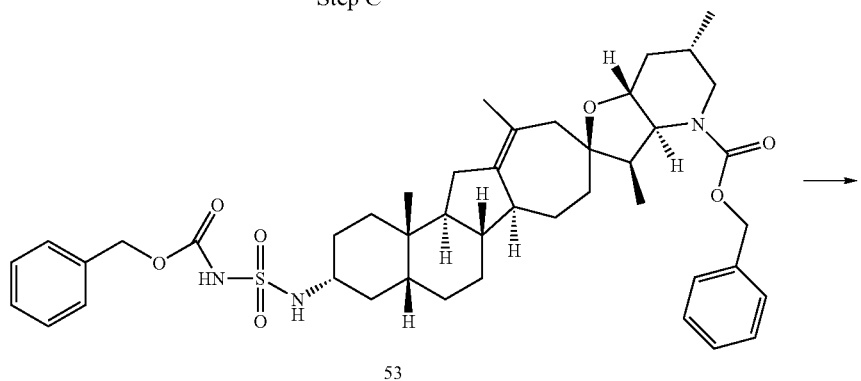

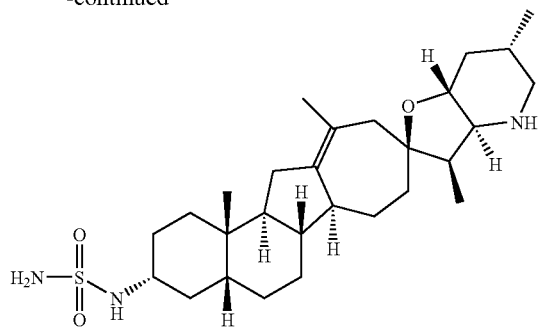

50

A round-bottom flask was charged with 53 (16 mg, 0.021 mmol, 1 equiv.) and 11 mg of 10% Pd/C (wet, Aldrich Degussa type E101). The material was suspended in 2-propanol (3 mL). The flask was sealed and purged three times with hydrogen and left overnight under 1 atm of hydrogen. The slurry was filtered through 0.2 micron Acrodisc, washed with 2-propanol, and the solvent was removed under vacuum. The residue was purification by $SiO_2$ column (1 g) eluting with $CH_2Cl_2$/MeOH (5% to 10%). The major product was lyophilized from t-BuOH/7% $H_2O$ to give 9 mg of sulfamide 50 ([M+H]=506.4 m/z).

Example 27

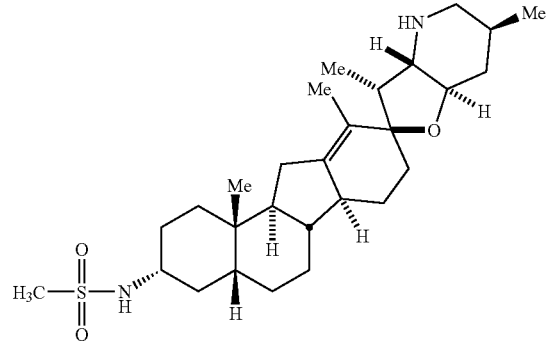

Step A

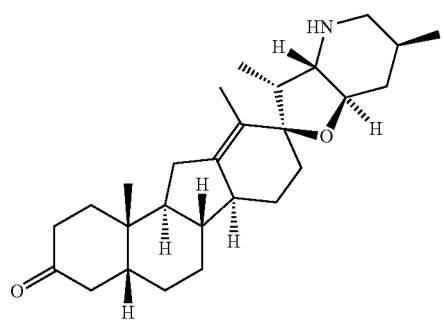

A round-bottom flask was charged with cyclopamine 4-en-3-one (3.5 g, 8.5 mmol, 1 equiv.) and pyridine (70 mL). The reactor was charged with Pd/C (10% Pd, 500 mg). The reaction was placed under 1 atmosphere of hydrogen. After 3.5 hrs, LCMS showed complete consumption of starting material. The catalyst was filtered off on an Acrodisk 0.2 micron filter and washed with toluene. The solvent was removed by azeotropic removal with toluene (2×10 mL). The desired material 56, 3.5 g ([M+H]=412.5 m/z) was used as it for the next step.

Step B

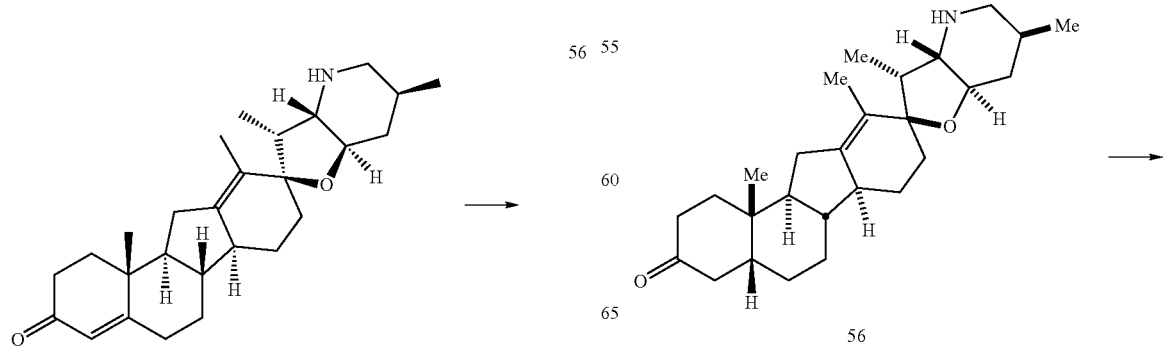

56

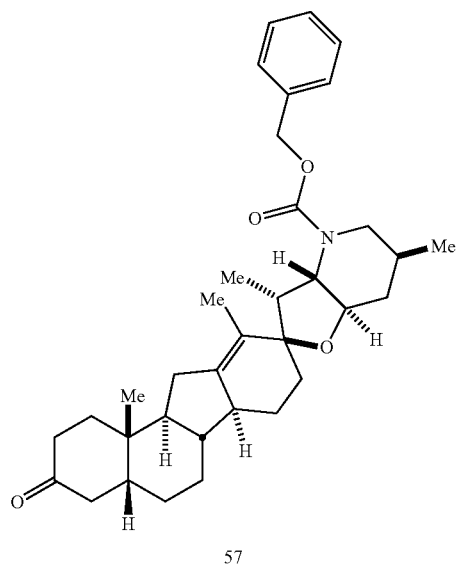

57

A round-bottom flask was charged with 56 (1.2 g, 2.8 mmol, 1 equiv.), CH$_2$Cl$_2$ (10 mL) and triethylamine (1.9 mL, 14.2 mmol, 5 equiv.). The cooled (0° C.) solution was treated with CBz-Cl (440 uL, 2.8 mmol, 1 equiv.). After 1 hr, LCMS showed complete consumption of starting material. The mixture was diluted with water. The layers were cut and the organic layer was washed twice with water. The organic layer was dried over sodium sulfate, filtered, and concentrated to dryness. The product was purified by column chromatography (SiO2, 40 g) eluting with hexane/EtOAc (0 to 20%) to give 57 (891 mg) ([M+Na]=468.4 m/z).

Step C

In a round-bottom flask, the ketone 57 was azeotroped a couple times with CH$_2$Cl$_2$ and dried under vacuum for 1 h. Under nitrogen, the ketone 2 (693 mg, 1.27 mmol, 1 equiv.) was dissolved in anhydrous THF (20 mL) and the solution was cooled to −78 C. A 1 M solution of K-selectride in THF (1.9 mL, 1.9 mmol, 1.5 equiv.) was added dropwise. After 1 h, the reaction was complete by TLC. The reaction was quenched by addition of 2.6 mL of 5 N NaOH followed by slow addition of 2.6 mL of 30% wt H$_2$O$_2$. The resulting mixture was allowed to stir overnight. The mixture was partitioned between water and EtOAc. The aqueous layer was back extracted with EtOAc. The combined organic were washed first with water (buffered with a small portion of ammonium chloride) then with brine. The organic were dried, filtered, and concentrated to a crude foam (840 mg) The crude material was dissolved in CH$_2$Cl$_2$, loaded on a SiO$_2$ column (40 g) and eluted with hexanes/EtOAc (0 to 50%) to give 58 (565 mg).

Step D

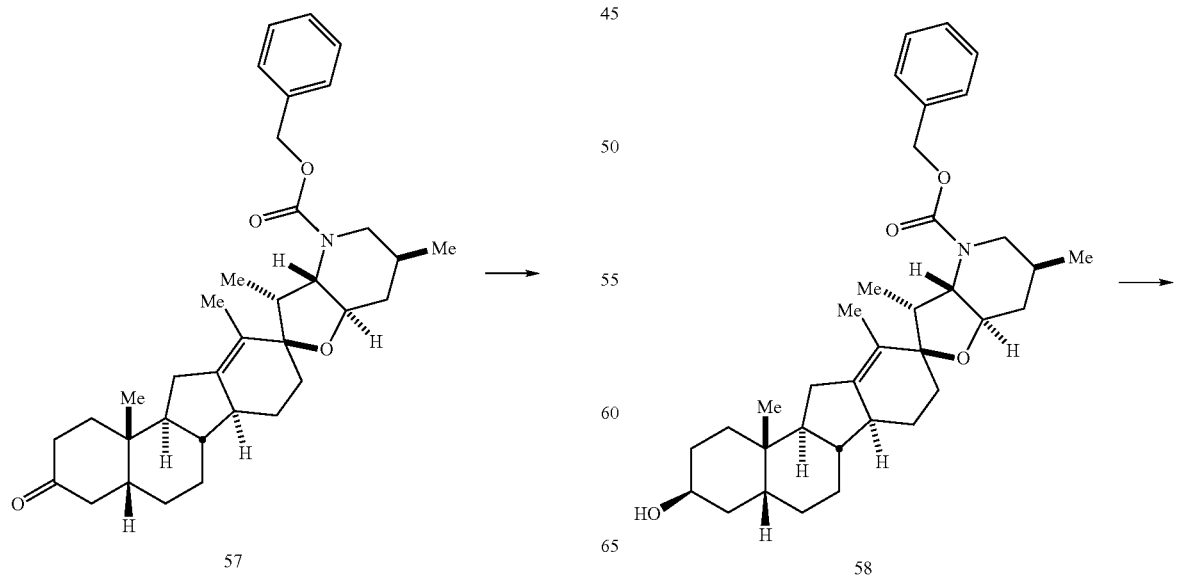

-continued

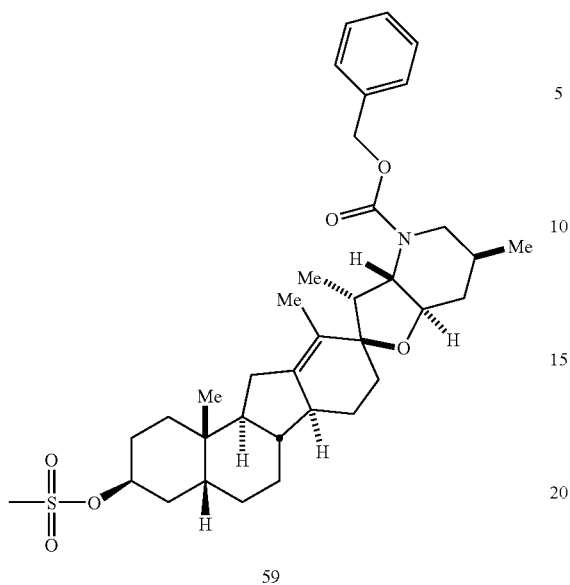

59

In a round-bottom flask under nitrogen, the alcohol 58 (530 mg, 0.98 mmol, 1 equiv.) was dissolved in 5 mL of anhydrous $CH_2Cl_2$ and triethylamine (800 uL, 5.81 mmol, 6 equiv.). The reaction mixture was cooled to 0° C. and Ms-Cl (112 uL, 1.45 mmol, 1.5 equiv) was added dropwise. The mixture was stirred at 0° C. for 30 min. TLC (hexane: EtOAC, 7:3) showed ~70% conversion. 70 uL of triethylamine (70 uL, 0.5 equiv.) and Ms-Cl (10 uL, 0.1 equiv) were charged to the reaction vessel. After 90 min, a solution of saturated bicarbonate was charged and the residue was extracted with $CH_2Cl_2$. The organic layer was washed with water, dried and concentrated to a off-white foam. The material was dissolved in $CH_2Cl_2$ and purified with SiO2 (40 g) eluting with hexanes/EtOAc (0% to 50%) to give 59 (430 mg).

-continued

60

In a round-bottom flask, the mesylate 59 (420 mg, 0.67 mmol, 1 equiv.) was dissolved in 2 mL of DMPU. The solution was treated with sodium azide (218 mg, 3.4 mmol, 5 equiv.) at 60° C. for 5 h. The mixture was cooled to 25° C., then poured into ice-water to generate a white solid. The compound was extracted with MTBE (3 times). The combined organic layers were washed with water (2×), then brine. The organic layers were dried over $Na_2SO_4$, filtered, and concentrated to a white foam (342 mg). The desired material 60 was used as is for the next step.

Step E

Step F

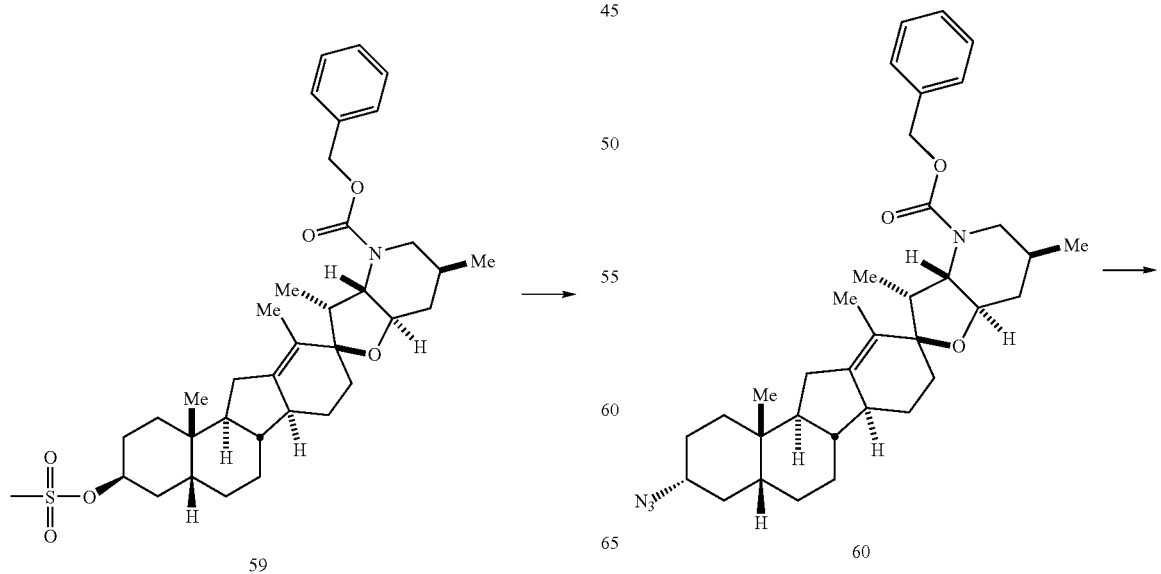

59        60

-continued

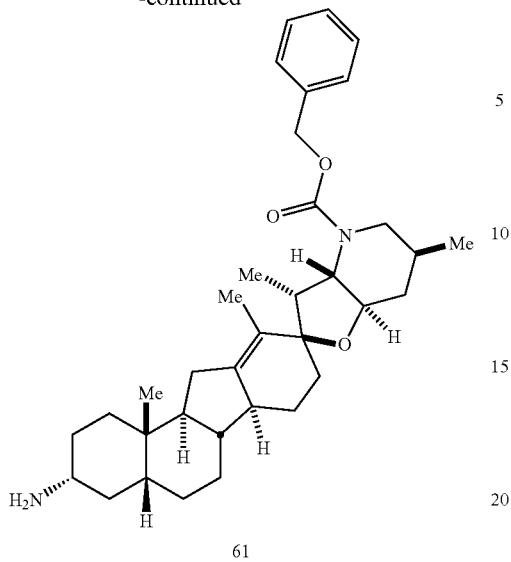

61

In a round-bottom flask equipped with a condenser, the azide 60 (336 mg, 0.58 mmol, 1 equiv.) was dissolved in 7 mL of THF and 140 uL of water and treated with triphenylphosphine (462 mg, 1.76 mmol, 3 equiv.). The mixture was heated to 70° C. overnight. TLC (hexane/EtOAc, 7:3) confirmed the reaction was complete. The reaction was concentrated to dryness. The crude material was dissolved in $CH_2Cl_2$, loaded onto 12 g of $SiO_2$ and eluted with $CH_2Cl_2$/MeOH (0 to 20%) to give the amine 61 (254 mg).

Step G

-continued

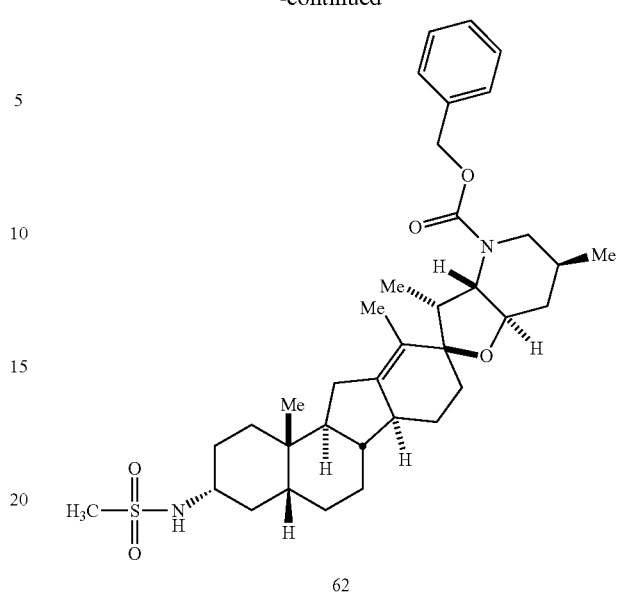

62

In a round-bottom flask under nitrogen, the amine 61 (248 mg, 0.45 mmol, 1 equiv.) was dissolved in 7 mL of anhydrous $CH_2Cl_2$ and N,N-diisopropylethylamine (237 uL, 0.91 mmol, 2 equiv.). The reaction mixture was cooled to 0° C. and Ms-Cl (70 uL, 1.45 mmol, 1.5 equiv) was added dropwise. The mixture was stirred at 0° C. for 2 h. TLC (hexane/EtOAc, 7:3) showed a little amount of amine. The mixture was charged with 10 uL of Ms-Cl (0.2 equiv.), and warmed to 25° C. for 1 h. The reaction mixture was diluted with $CH_2Cl_2$ then a saturated solution of $NaHCO_3$. The layers were cut. The aqueous layer was extracted with one portion of $CH_2Cl_2$. The combined organic layers were washed with water, dried over $Na_2SO_4$, filtered and concentrated to dryness. The crude (326 mg) was added to a $SiO_2$ column (12 g) and was eluted with hexanes/EtOAc (0 to 50%) to give the sulfonamide 62 (256 mg).

Step H

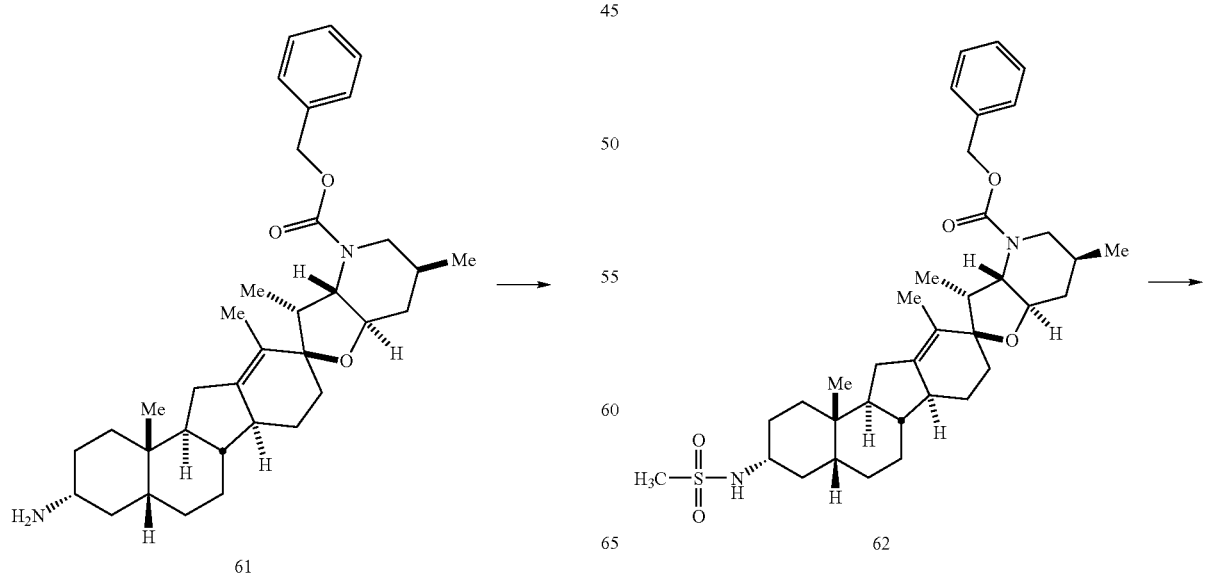

-continued

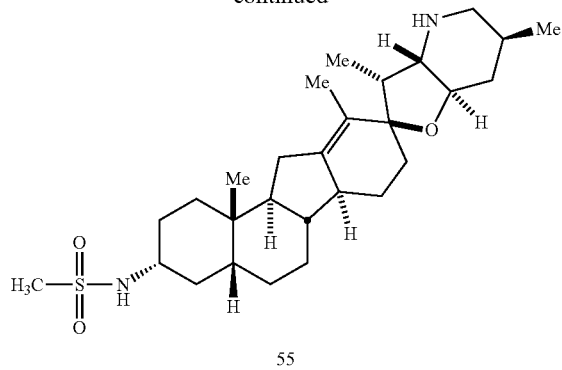

55

A round-bottom flask was charged with the sulfonamide 62 (250 mg, 0.4 mmol, 1 equiv.) and 50 mg of 10% Pd/C (wet, Aldrich Degussa type E101 lot 08331KC). The material was suspended in EtOAc (5 mL). The flask was sealed and purged three times with hydrogen and stirred under 1 atm of hydrogen. After 3 h some conversion was observed, but a lot of starting material remained. The slurry was filtered through 0.2 micron Acrodisc, washed with 2-propanol. The filtrate solution was re-subjected to the reaction condition by adding 54 mg of catalyst. The reaction was completed after 3 h. The slurry was filtered through 0.2 micron Acrodisc, washed with 2-propanol, and the solvent was concentrated to dryness. The crude material (200 mg) was loaded onto a $SiO_2$ column (12 g) and the compound was eluted using a gradient $CH_2Cl_2$/MeOH (0 to 10%) to give the free amine. The material was lyophilized from t-BuOH/7% $H_2O$ to give 175 mg of 55 as a white powder ([M+H]=491.3 m/z).

Example 28

Inhibition of the Hedgehog Pathway in Cell Culture

Hedgehog pathway specific cancer cell killing effects may be ascertained using the following assay. $C_3H10T1/2$ cells differentiate into osteoblasts when contacted with the sonic hedgehog peptide (Shh-N). Upon differentiation; these osteoblasts produce high levels of alkaline phosphatase (AP) which can be measured in an enzymatic assay (Nakamura, et al., *BBRC* (1997) 237:465). Compounds that block the differentiation of C3H10T1/2 into osteoblasts (a Shh dependent event) can therefore be identified by a reduction in AP production (van der Horst, et al., *Bone* (2003) 33:899). The assay details are described below. The results approximate ($EC_{50}$ for inhibition) of the differentiation assay is shown below in Table 1.

Assay Protocol
Cell Culture

Mouse embryonic mesoderm fibroblasts C3H10T1/2 cells (obtained from ATCC) were cultured in Basal MEM Media (Gibco/Invitrogen) supplemented with 10% heat inactivated FBS (Hyclone), 50 units/ml penicillin and 50 ug/ml streptomycin (Gibco/Invitrogen) at 37° C. with 5% CO2 in air atmosphere.

Alkaline Phosphatase Assay

C3H10T1/2 cells were plated in 96 wells with a density of $8 \times 10^3$ cells/well. Cells were grown to confluence (72 hrs). After sonic Hedgehog (250 ng/ml), and/or compound treatment, the cells were lysed in 110 µL of lysis buffer (50 mM Tris pH 7.4, 0.1% TritonX100), plates were sonicated and lysates spun through 0.2 µm PVDF plates (Corning). 40 µL of lysates was assayed for AP activity in alkaline buffer solution (Sigma) containing 1 mg/ml p-Nitrophenyl Phosphate. After incubating for 30 min at 37° C., the plates were read on an Envision plate reader at 405 nm. Total protein was quantified with a BCA protein assay kit from Pierce according to manufacturer's instructions. AP activity was normalized against total protein. Note that "A" indicates that the $IC_{50}$ is less than 20 nM, "B" indicates that the $IC_{50}$ is 20-100 nM, "C" indicates that the $IC_{50}$ is >100 nM.

TABLE 1

Approximate $EC_{50}$ for Inhibition

| Compound | Differentiation Assay $EC_{50}$ |
|---|---|
| 1 | A |
| 7 | C |
| 8 | C |
| 9 | C |
| 10 | C |
| 13 | A |
| 20 | A |
| 21 | B |
| 22 | A |
| 23 | A |
| 24 | A |
| 27 | B |
| 29 | B |
| 31 | B |
| 33 | C |
| 35 | A |
| 37 | A |
| 39 | B |
| 40 | A |
| 42 | A |
| 55 | A |

Example 29

Pancreatic Cancer Model

The activity of Compound 42 was further tested in a human pancreatic model: BXPC-3 cells were implanted subcutaneously into the flanks of the right legs of mice. On day 42 post-tumor implant, the mice were randomized into two groups to receive either Vehicle (30% HPBCD) or Compound 42. Compound 42 was administered orally at 40 mg/kg/day. After receiving 25 daily doses, Compound 42 statistically reduced tumor volume growth by 40% when compared to the vehicle control (p=0.0309). At the end of the study, the tumors were harvested 4 hours post the last dose to evaluate an on target response by q-RT-PCR analysis of the HH pathway genes. Analysis of human Gli-1 resulted in no modulation. Analysis of murine Gli-1 mRNA levels resulted in a robust down-regulation in the Compound treated group, when compared to the Vehicle treated group. Inhibition of the hedgehog pathway in mouse cells, but not human tumor cells, indicates that one effect of the hedgehog inhibitor is to affect a tumor-stroma interaction.

Example 30

Medulloblastoma Model

The activity of Compound 42 was also evaluated in a transgenic mouse model of medulloblastoma. Mice that are heterozygous for loss of function mutations in the tumor suppressors Patched1 (Ptch1) and Hypermethylated in Cancer (Hic1) develop spontaneous medulloblastoma. Similar to human medulloblastoma, these tumors demonstrate complete promoter hypermethylation of the remaining Hic1 allele, as well as loss of expression of the wild type Ptch1 allele. When passaged as subcutaneous allografts, these tumors grow aggressively and are Hedgehog pathway-dependent. This model was employed to evaluate the efficacy of orally administered Compound, and to correlate activity with drug exposure in plasma and tumors. Oral administration (PO) of a single dose of Compound 42 led to dose-dependent down-regulation of the HH pathway in subcutaneously implanted tumors, as measured by decreased Gli-1 mRNA expression 8 hours post dose administration.

Daily (QD) administration of the Compound PO led to a dose dependent inhibition of tumor growth, with frank tumor regression seen at higher doses. The approximate effective daily oral dose for 50% inhibition of tumor growth (ED50) is 4 mg/kg. When animals were treated QD for 21 days, long term survival was observed following cessation of treatment (>60 days), with little to no tumor re-growth. This demonstrates that the hedgehog inhibitor Compound 42 inhibits both the hedgehog pathway and tumor growth in a tumor dependent on the hedgehog pathway due to a genetic mutation.

Example 31

Lung Cancer Model

To test the activity of Compound 42 in a human SCLC tumor model, LX22 cells were implanted subcutaneously into the flank of the right leg. LX22 is primary xenograft model of SCLC derived from chemo-naive patients, which has been maintained by mouse to mouse passaging. This tumor responds to etoposide/carboplatin chemotherapy in way that closely resembles a clinical setting. LX22 regresses during chemotherapy treatment, goes through a period of remission, and then begins to recur. In the LX22 model, Compound single agent activity and its ability to modulate the chemoresistant recurrence was tested. On day 32 post tumor implant, mice were randomized into three dosing groups to receive Vehicle (30% HBPCD), Compound, or the chemotherapy combination of etoposide and carboplatin (E/P). Compound 42 was administered orally at a dose of 40 mg/kg/day, and after 16 consecutive doses there was no measurable difference between the treated and vehicle groups. Etoposide was administered i.v at 12 mg/kg on days 34, 35, 36, and 48, while Carboplatin was administered i.v. at 60 mg/kg on days 34, 41, and 48, post tumor implant. On day 50, the E/P treated mice were further randomized to receive either Vehicle (30% HPBCD) or Compound follow up treatment. The Compound was administered at the oral multi-dose MTD of 40 mg/kg/day, and after 35 consecutive doses there was a substantial delay in tumor recurrence in the treated group, compared to the vehicle group (p=0.0101).

Example 32

Multiple Myeloma

The ability of Compound 42 to inhibit the growth of multiple myeloma cells (MM) in vitro was tested, using human multiple myeloma cells lines (NCI-H929 and KMS12) and primary clinical bone marrow specimens derived from patients with MM. The cells were treated for 96 hours with Compound, washed, then plated in methylcellulose. Tumor colonies were quantified 10-21 days later as an indicator of cell growth potential following treatment. Treatment of cell lines or primary patient specimens resulted in decreased cell growth compared to an untreated control. Where the untreated control showed 100% growth of cells, each of the treated cell lines, as well as the clinical samples, showed less than about 25% growth.

Example 33

Acute Myeloid Leukemia and Myelodysplastic Syndrome

The ability of Compound 42 to inhibit the in vitro growth of human cell lines derived from patients with acute myeloid leukemia (AML, cell line U937) and myelodysplastic syndrome (MDS, cell line KG1 and KG1a) was studied. Each of the cell lines was treated for 72 hours with Compound 42 (1.0 uM) followed by plating in methylcellulose. Growth of these cell lines was inhibited by Compound 42, as summarized in the table below.

TABLE 2

Inhibition of cell growth in AML and MDS

| | Disease | | |
|---|---|---|---|
| | AML | MDS | |
| | Cell line | | |
| | U937 | KG1 | KG1a |
| % colony formation with Compound 42 (relative to vehicle control) | 43.4 | 25.1 | 34.6 |

Example 34

Non-Hodgkin's Lymphoma (NHL) and Hodgkin's Disease (HD)

The ability of Compound 42 to inhibit the in vitro growth of human cell lines derived from patients with non-Hodgkin's lymphoma (cell lines RL and Jeko-1) and Hodgkin's disease (cell line L428) was studied. Each of the cell lines was treated for 72 hours with Compound 42 (1.0 uM) followed by plating in methylcellulose. Growth of these cell lines was inhibited by Compound 42, as summarized in the table below.

TABLE 3

Inhibition of cell growth in HD and NHL

| | Disease | | |
|---|---|---|---|
| | HD | NHL | |
| | Cell line | | |
| | L428 | RL | Jeko-1 |
| % colony formation with Compound 42 (relative to vehicle control) | 21.4 | 14.3 | 27.4 |

Example 35

Pre-B Cell Acute Lymphocytic Leukemia

The activity of Compound 42 (1 uM) against three pre-B cell acute lymphocytic leukemia cell lines (REH, RS4-11, and Nalm-6) was studied, using a transient transfection assay in which a Gli-responsive luciferase reporter was transiently transfected into cells. Treatment with Compound 42 repressed luciferase activity compared to a vehicle treated control (Table 4). This demonstrates that Compound 42 is an effective antagonist of the hedgehog pathway.

TABLE 4

Repression of luciferase activity

| | Cell line | | |
|---|---|---|---|
| | REH | RS4-11 | Nalm-6 |
| Relative luc activity (vehicle alone) | 6.73 | 12.97 | 8.42 |
| Relative luc activity (+Compound) | 1.12 | 1.31 | 1.44 |

The effect of Compound 42 on the growth of two of these cell lines, treated in vitro for 72 hours, was also studied. Following treatment, cells were washed and plated in methylcellulose. There was little inhibition of colony formation, but subsequent replating of colonies demonstrated a significant inhibition of cell growth (Table 5).

TABLE 5

Inhibition of cell growth in ALL

| | Cell line | |
|---|---|---|
| | REH | RS4-11 |
| % colony formation with Compound (relative to vehicle control) - 1° plating | 63 | 71 |
| % colony formation with Compound (relative to vehicle control) - 2° plating | 9 | 11 |

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:
1. A method for antagonizing the hedgehog pathway in a mammal comprising administering to the mammal a compound of the formula:

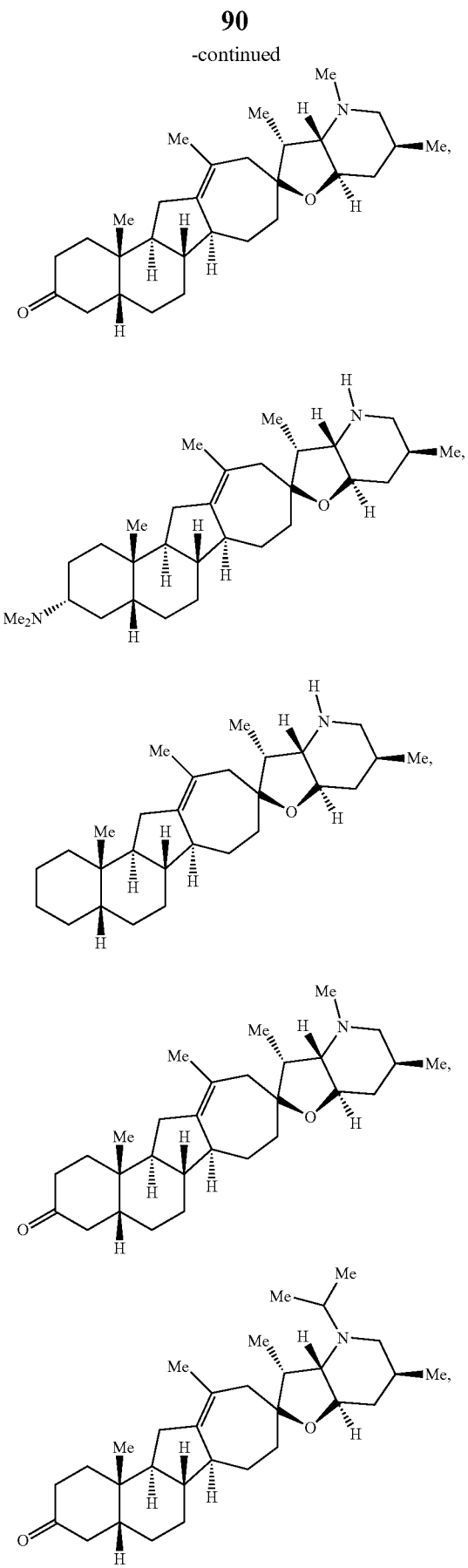

91
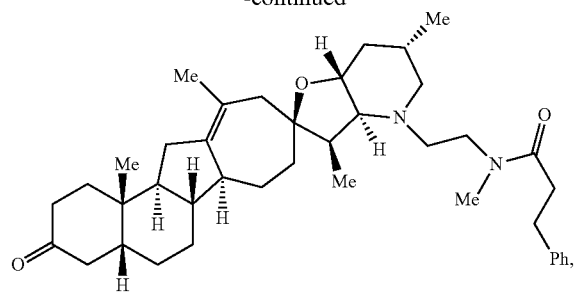
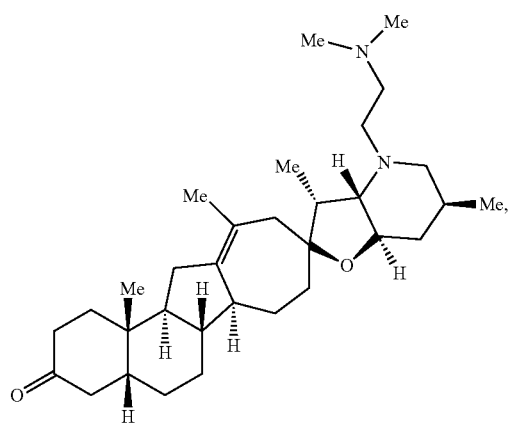
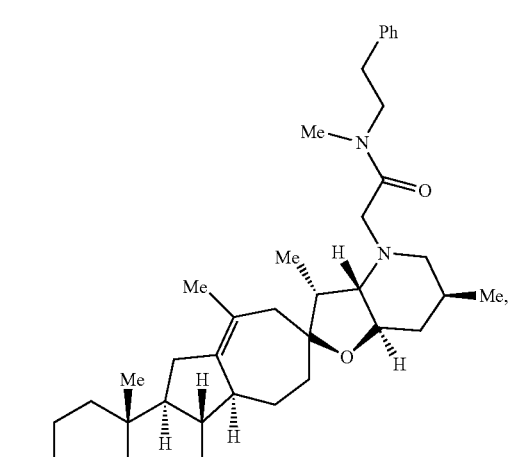
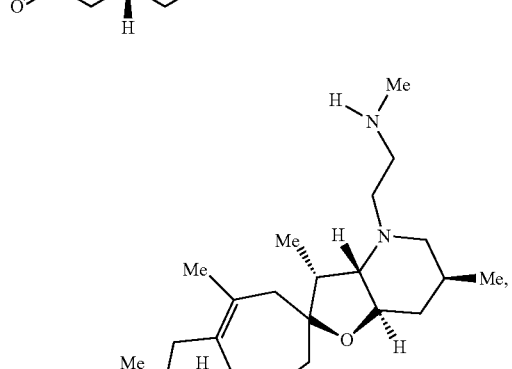
92
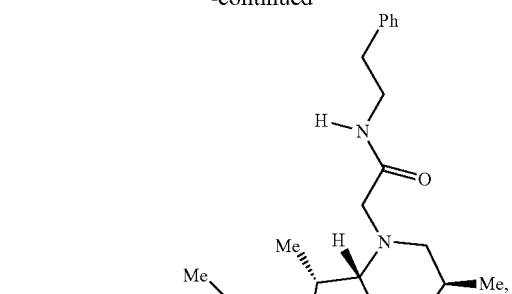
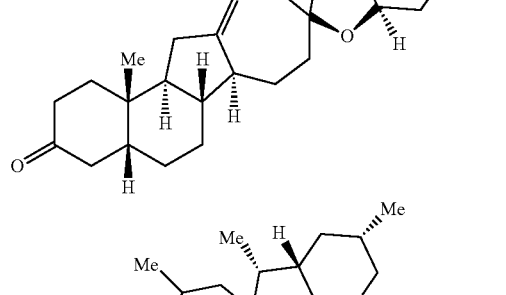
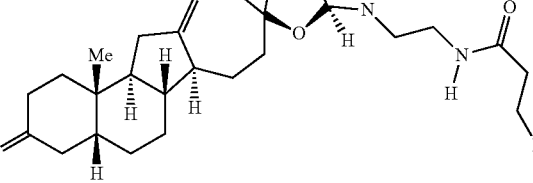
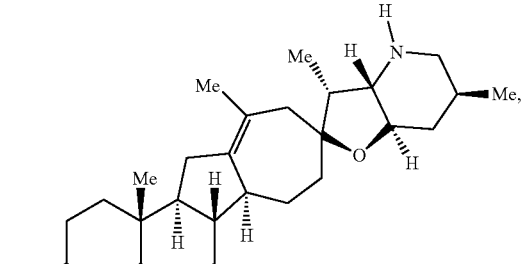
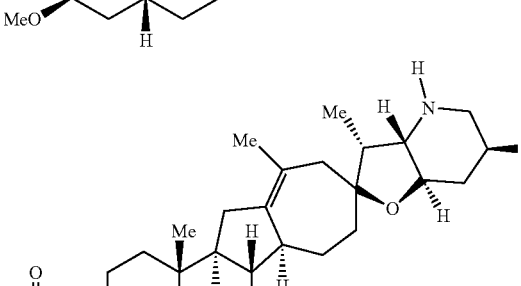
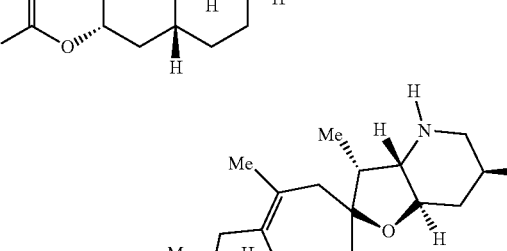

93
-continued
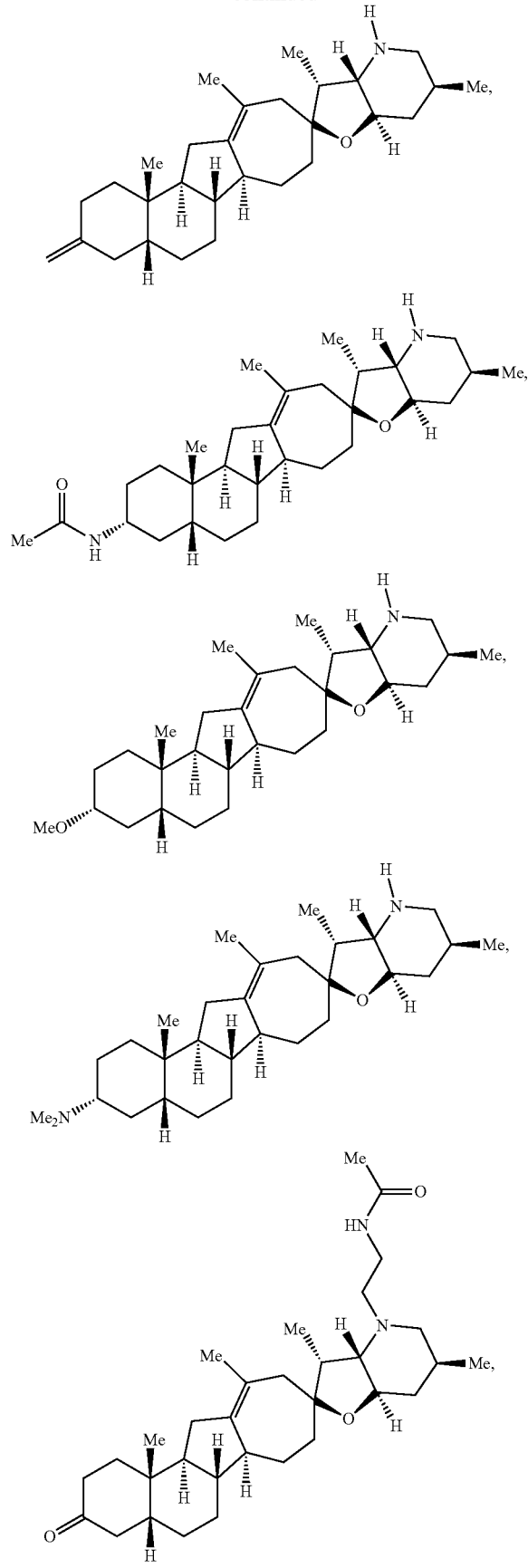
94
-continued
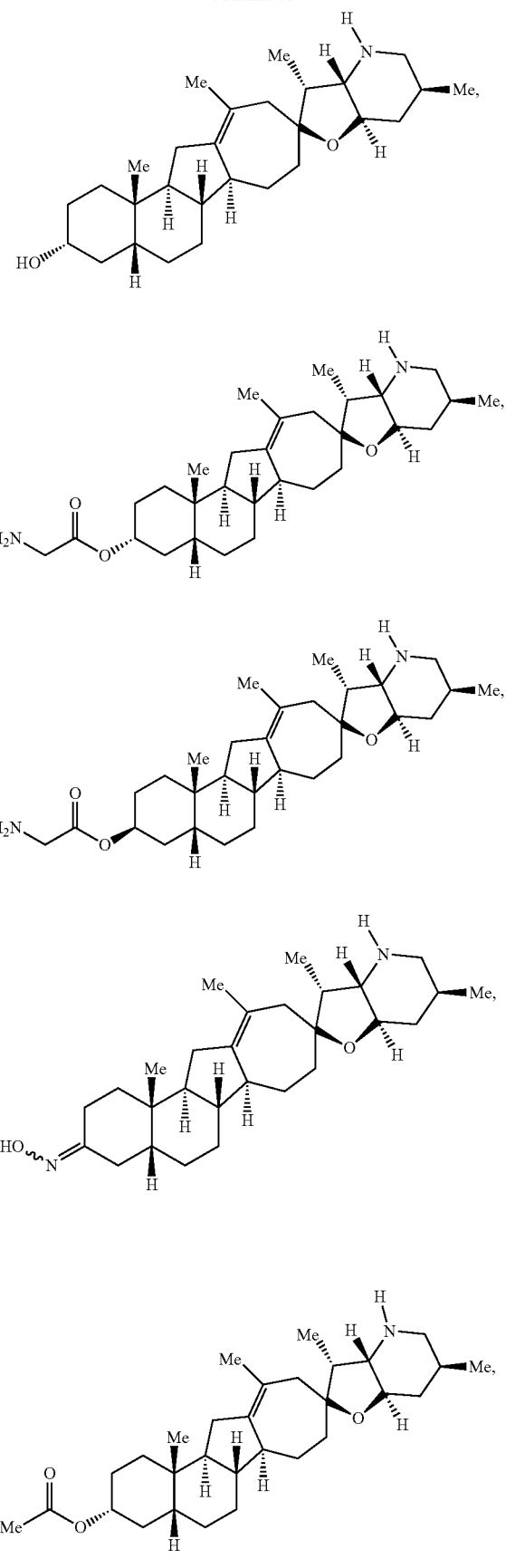

95
-continued
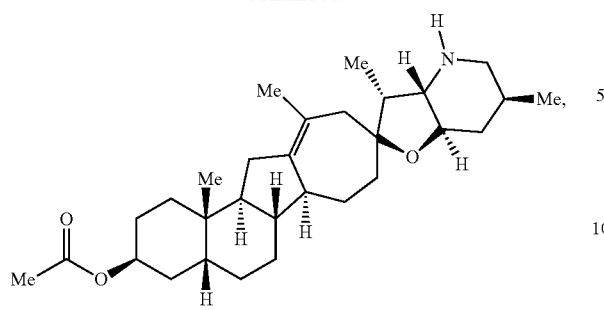
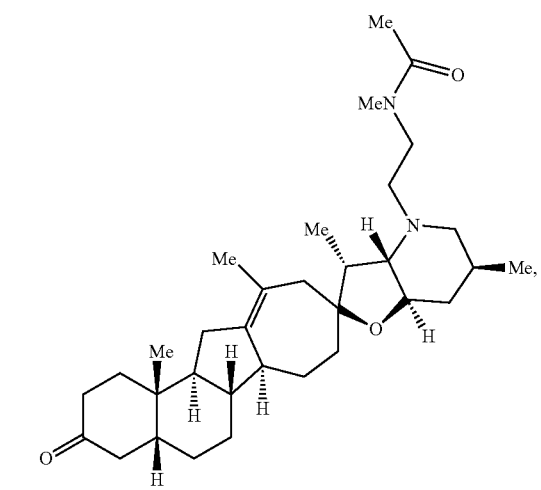
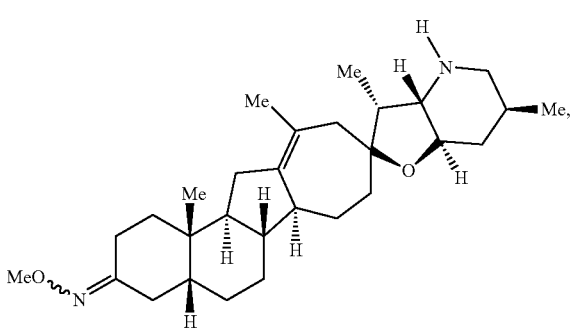
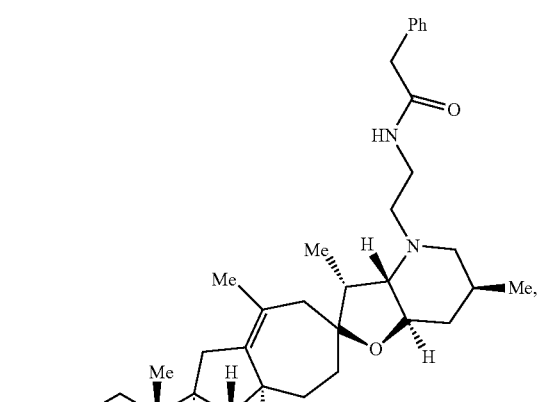
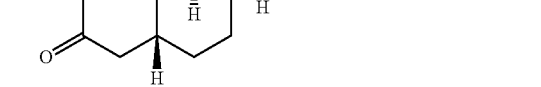
96
-continued
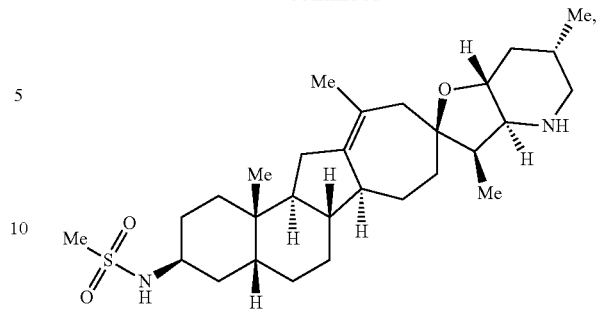
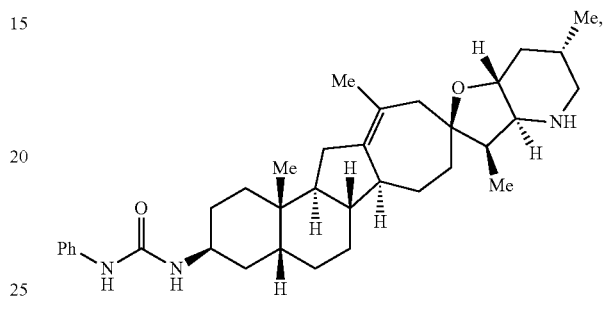
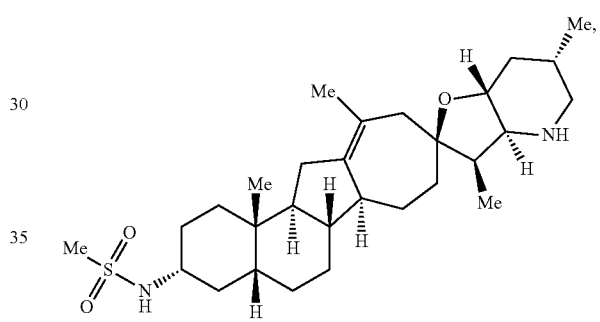
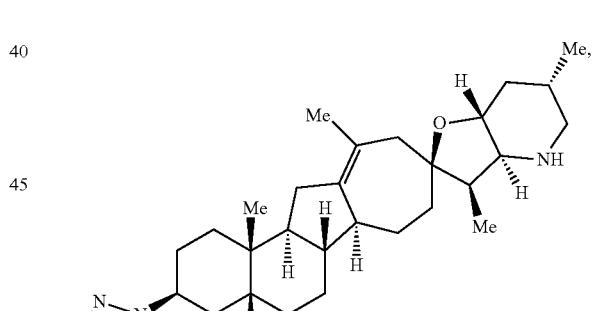
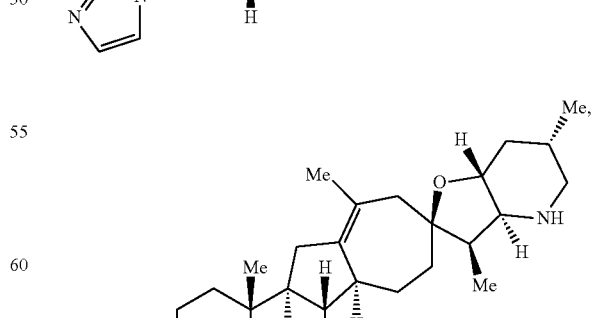
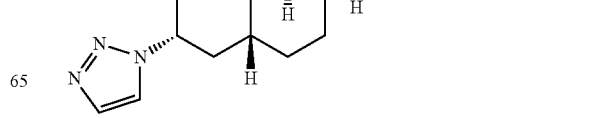

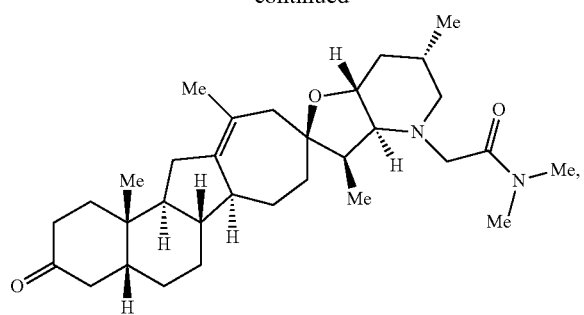
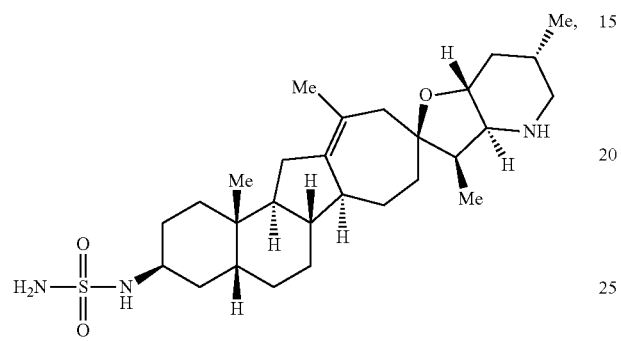
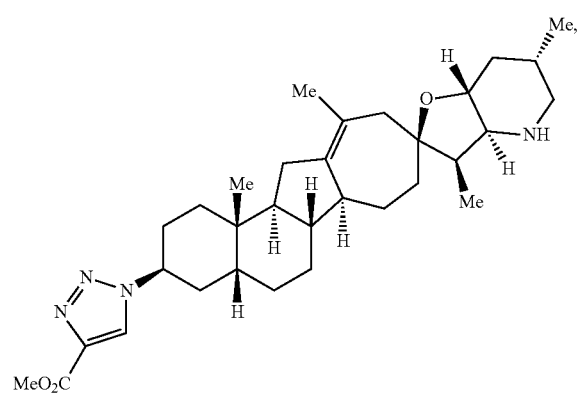
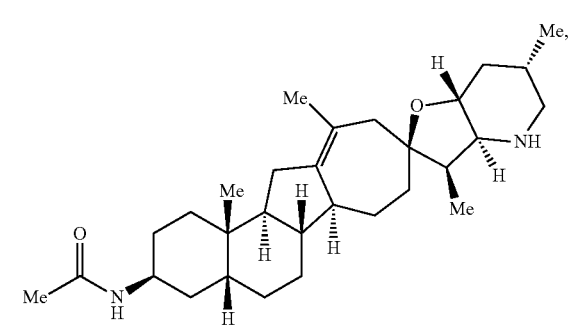
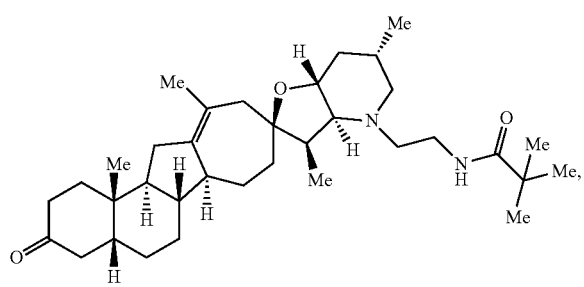
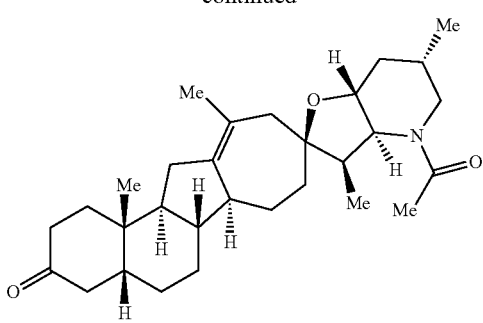
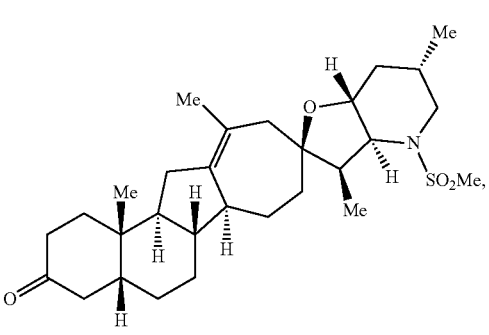
or a pharmaceutically acceptable salt thereof.
2. The method of claim 1, wherein the compound is:
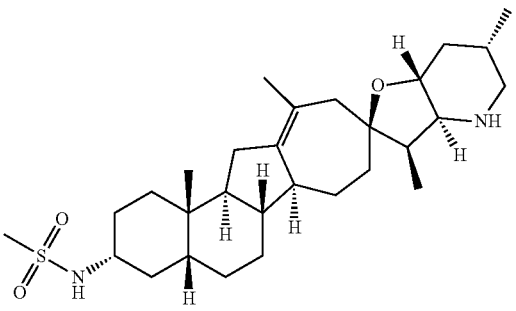
or a pharmaceutically acceptable salt thereof.
3. The method of claim 2, wherein the compound is a hydrochloride salt.
4. A method for treating cancer in a mammal comprising administering to the mammal a compound of formula:
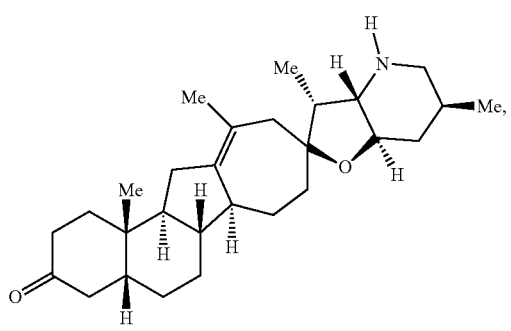

99
-continued
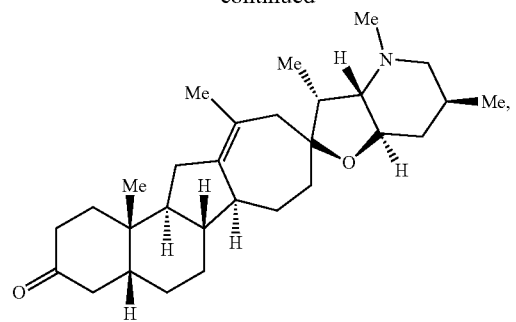
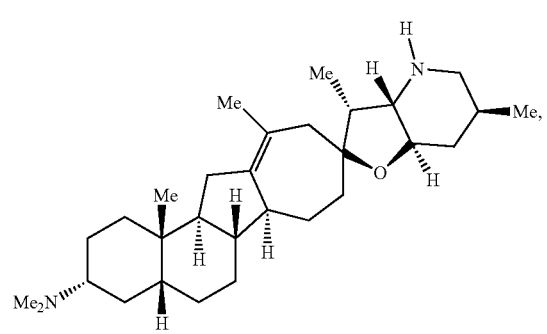
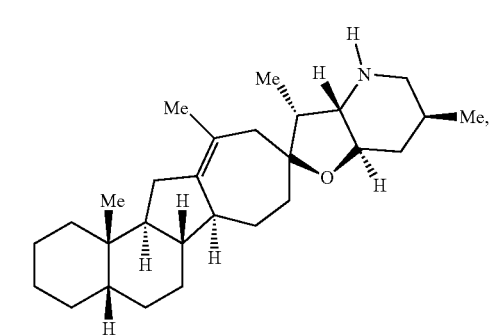
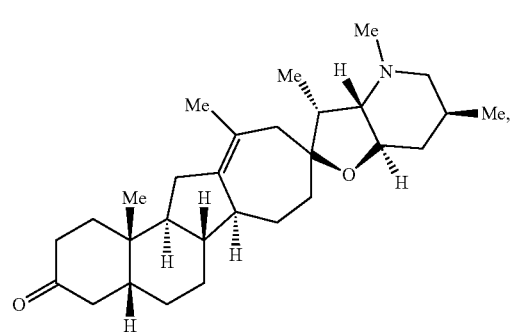
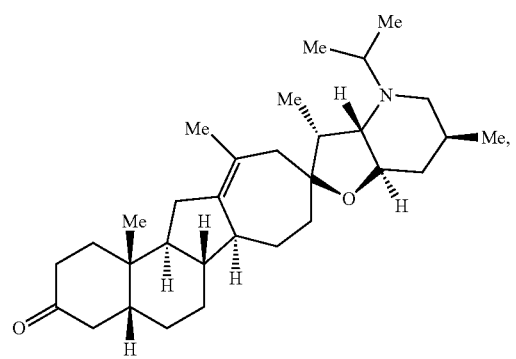
100
-continued
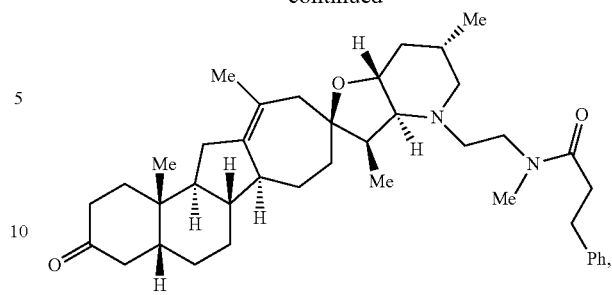
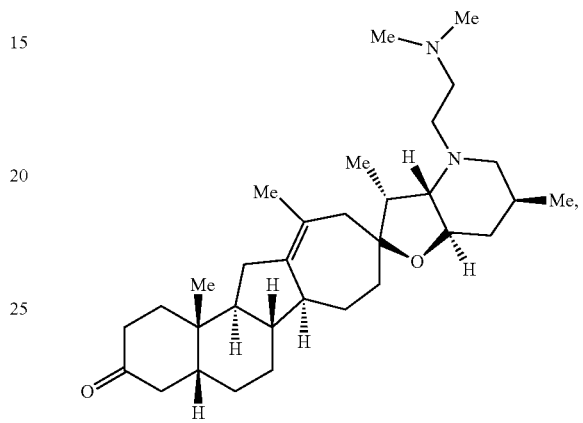
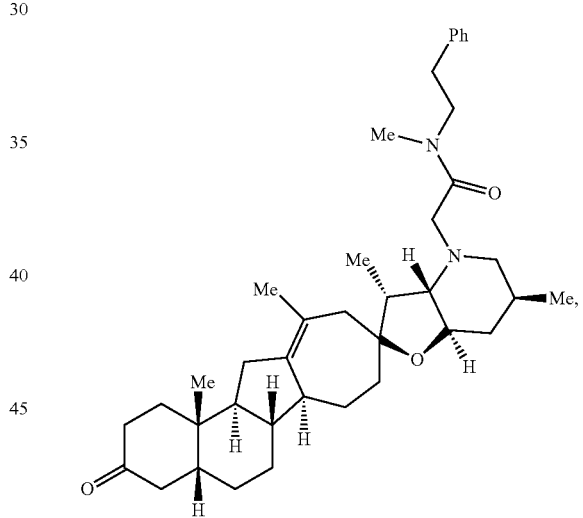
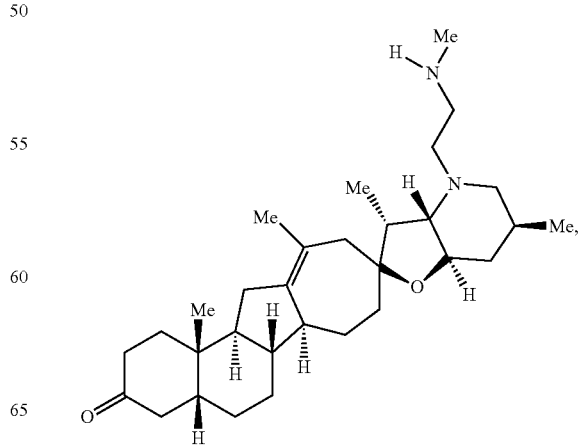

101
-continued
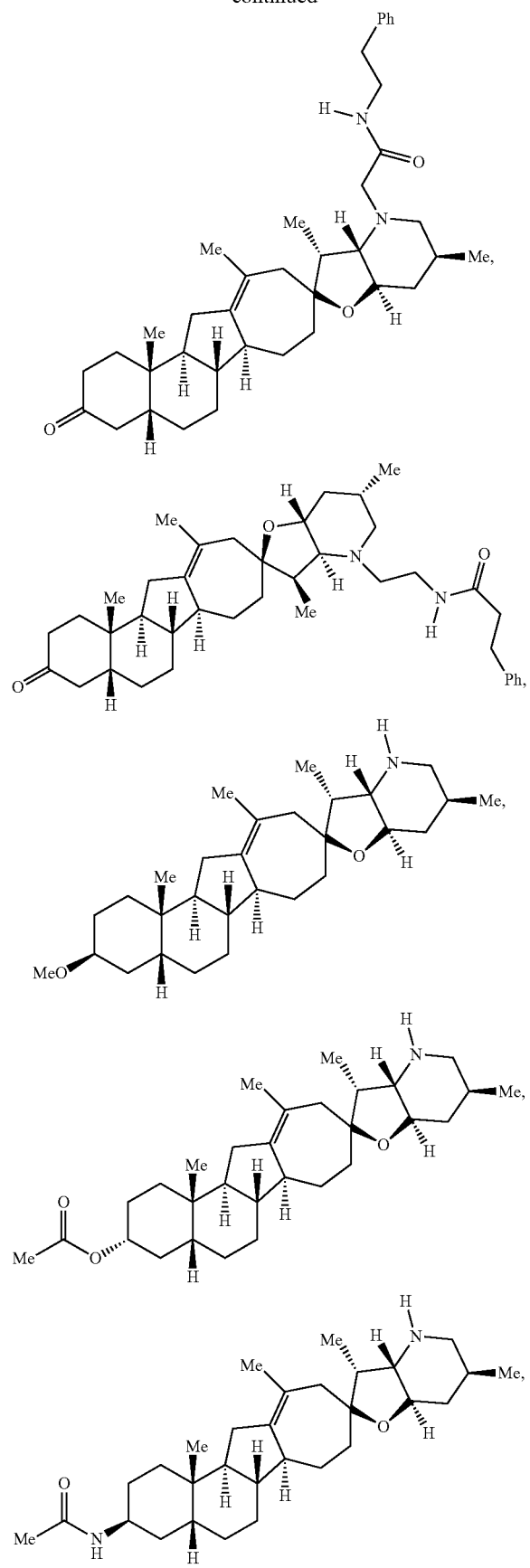
102
-continued
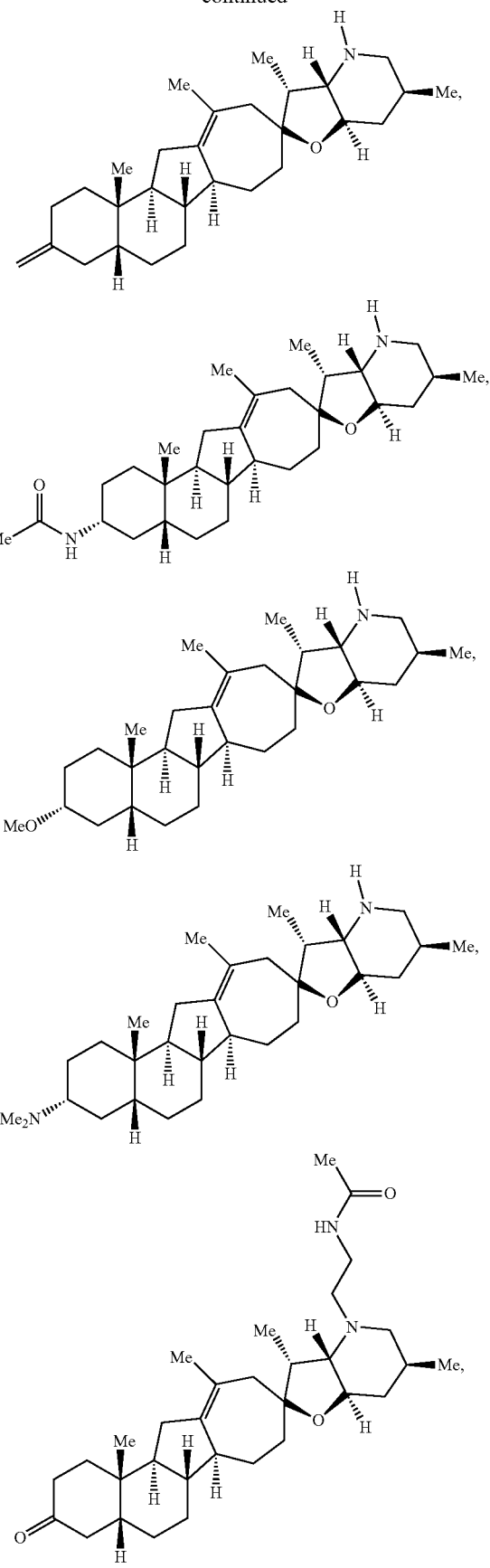

103
-continued
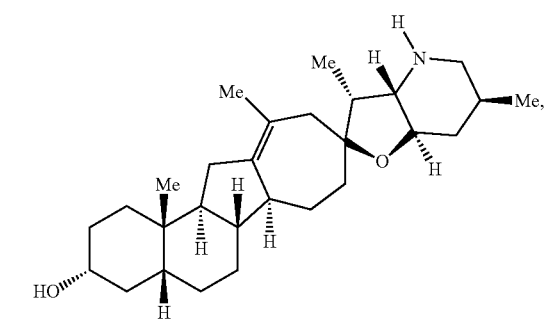
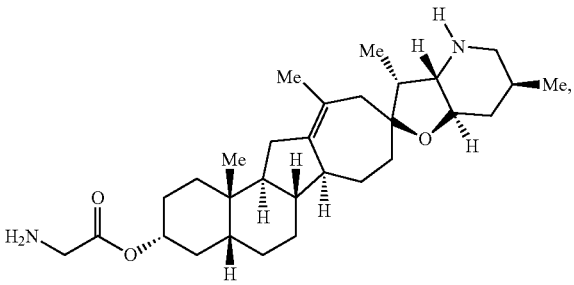
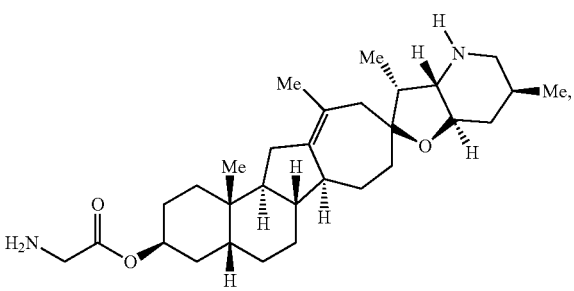
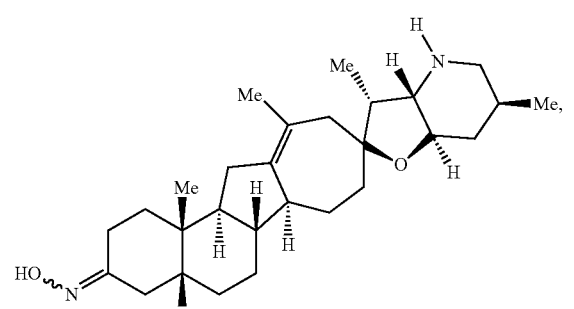
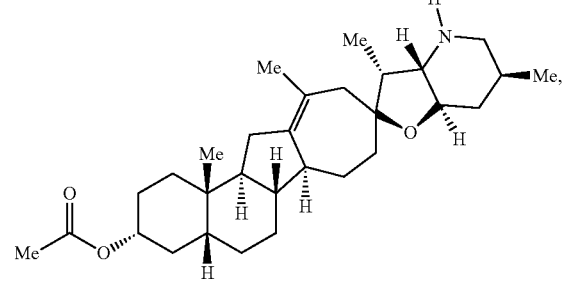
104
-continued
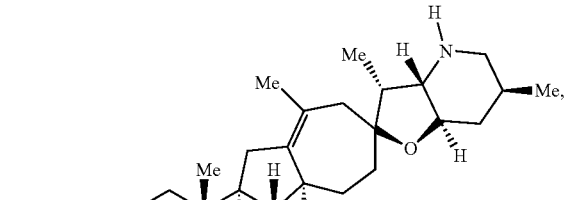
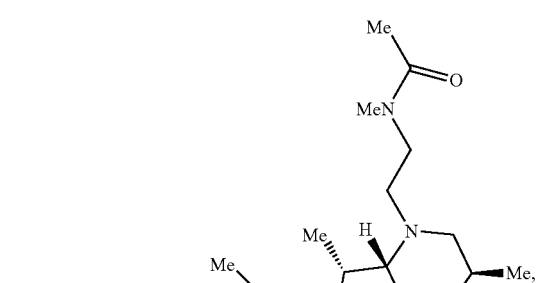
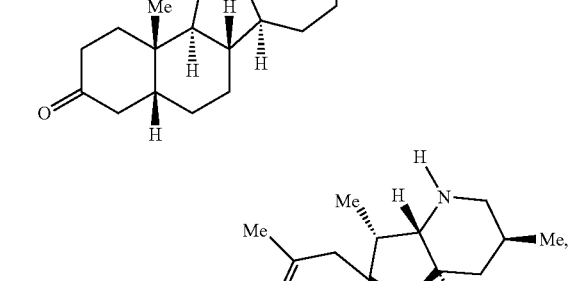
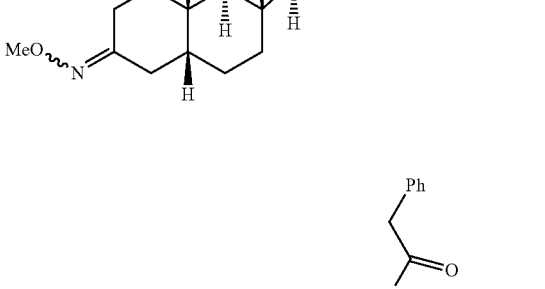
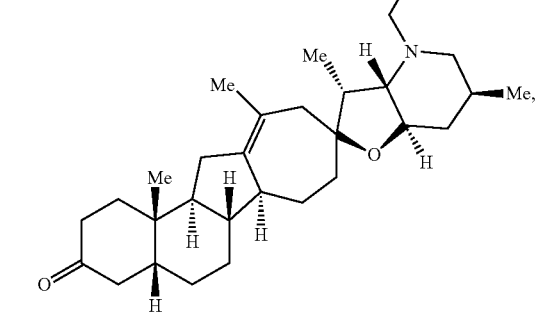

105
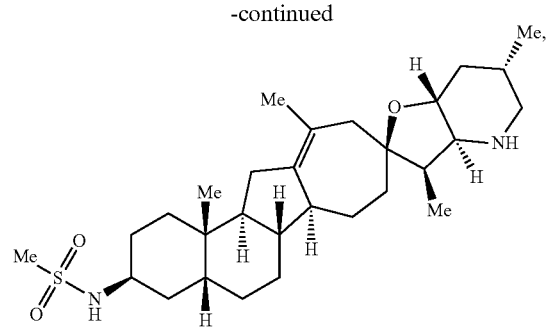
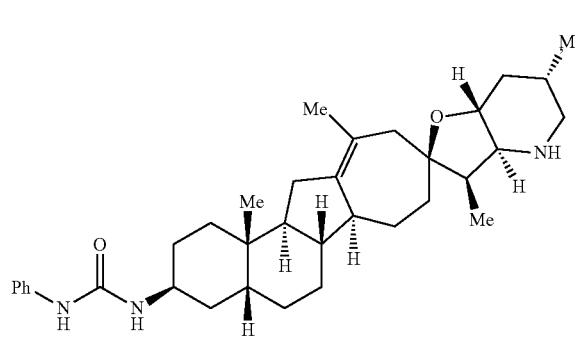
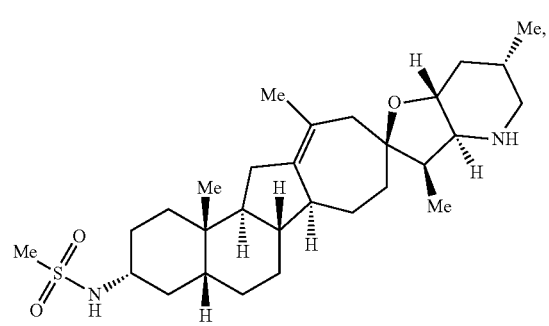
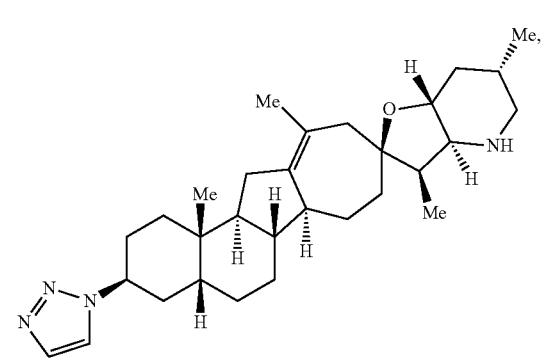
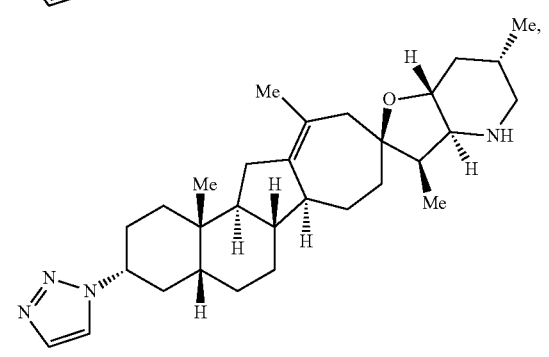
106
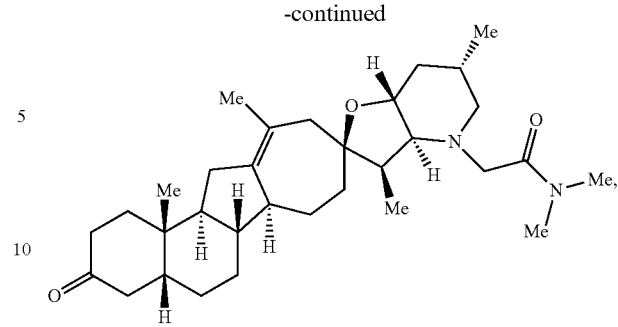
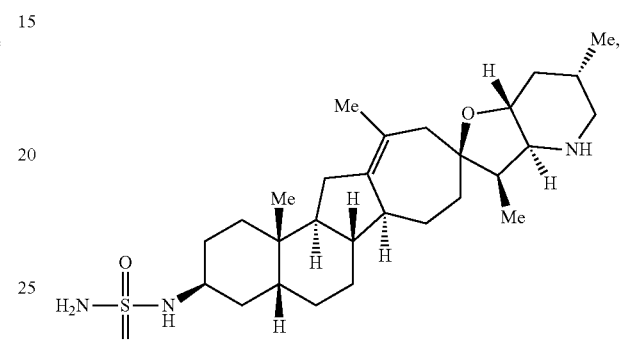
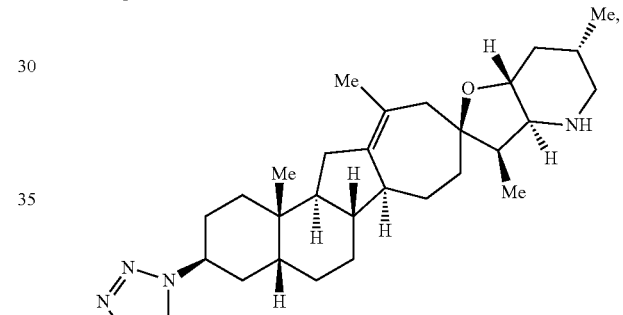
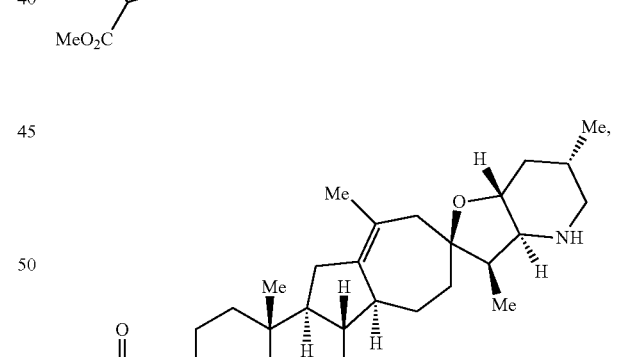
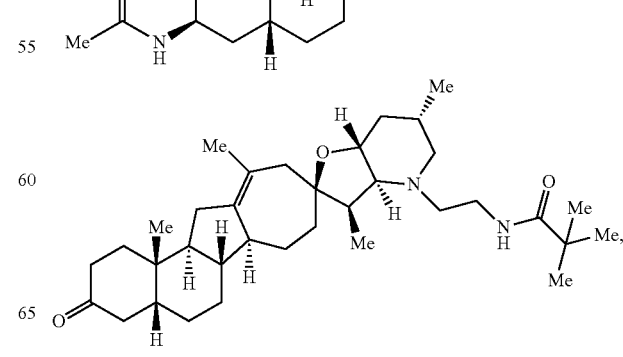

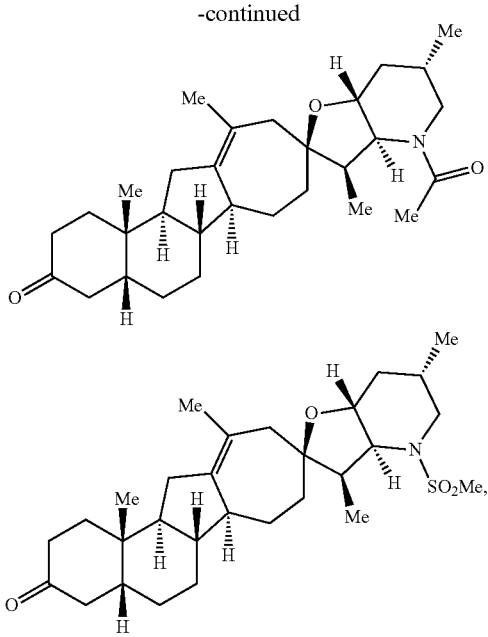

or a pharmaceutically acceptable salt thereof;
wherein said cancer is selected from the group consisting of basal cell carcinoma, glioma, breast cancer, chondrosarcoma, colon cancer, esophageal cancer, gastric cancer, gastrointestinal stromal tumor, hepatocellular cancer, lung cancer, medulloblastoma, melanoma, neuroectodermal tumors, osteogenic sarcoma, ovarian cancer, pancreatic cancer, prostate cancer, and testicular cancer.

5. The method of claim 4, wherein the cancer is basal cell carcinoma, pancreatic cancer, prostate cancer, osteogenic sarcoma, chondrosarcoma, gastric cancer, esophageal cancer, lung cancer, glioma, breast cancer, hepatocellular cancer, ovarian cancer, colon cancer or medulloblastoma.

6. The method of claim 4, wherein the cancer is pancreatic cancer.

7. The method of claim 4, wherein the cancer is chondrosarcoma.

8. The method of claim 4, wherein the cancer is lung cancer.

9. The method of claim 8, wherein the lung cancer is small cell lung cancer.

10. The method of claim 4, wherein the cancer is basal cell carcinoma.

11. The method of claim 4, wherein the cancer is medulloblastoma.

12. The method of claim 4, wherein the cancer is ovarian cancer.

13. The method of claim 4, wherein the cancer is osteogenic sarcoma.

14. The method of claim 4, wherein the compound is used in combination with one or more chemotherapeutic or other anti-cancer agent.

15. The method of claim 14, wherein the other anti-cancer agent is radiation.

16. The method of claim 4, wherein the compound is administered locally to a tumor.

17. The method of claim 4, wherein the compound is administered systemically.

18. The method of claim 4, wherein the mode of administration of said compound is inhalation, oral, intravenous, sublingual, ocular, transdermal, rectal, vaginal, topical, intramuscular, intraperitoneal, epidural, subcutaneous, buccal, or nasal.

19. The method claim 18, wherein the mode of administration is oral, intravenous, or topical.

20. The method of claim 4, wherein the compound is:

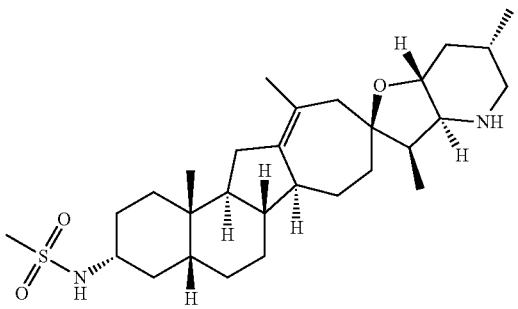

or a pharmaceutically acceptable salt thereof.

21. The method of claim 20, wherein the compound is a hydrochloride salt.

* * * * *